(12) United States Patent
Gumede

(10) Patent No.: US 11,548,860 B2
(45) Date of Patent: Jan. 10, 2023

(54) PHARMACOPHORES, COMPOUNDS AND METHODS HAVING APPLICATION IN THE TREATMENT OF CANCER THROUGH INHIBITION OF CYP17A1 AND CYP19A1

(71) Applicant: MANGOSUTHU UNIVERSITY OF TECHNOLOGY, Durban (ZA)

(72) Inventor: Njabulo Joyfull Gumede, Durban (ZA)

(73) Assignee: MANGOSUTHU UNIVERSITY OF TECHNOLOGY, Durban (ZA)

( * ) Notice: Subject to any disclaimer, the term of this patent is extended or adjusted under 35 U.S.C. 154(b) by 421 days.

(21) Appl. No.: 15/769,824

(22) PCT Filed: Oct. 22, 2016

(86) PCT No.: PCT/ZA2016/050041
§ 371 (c)(1),
(2) Date: Apr. 20, 2018

(87) PCT Pub. No.: WO2017/070718
PCT Pub. Date: Apr. 27, 2017

(65) Prior Publication Data
US 2020/0247764 A1 Aug. 6, 2020

(30) Foreign Application Priority Data
Oct. 22, 2015 (ZA) ................. 2015/07849

(51) Int. Cl.
| | | |
|---|---|---|
| *C07D 265/36* | (2006.01) |
| *C07D 413/12* | (2006.01) |
| *C07D 231/56* | (2006.01) |
| *C07C 311/29* | (2006.01) |
| *C07D 417/12* | (2006.01) |
| *C07D 405/14* | (2006.01) |
| *C07D 309/34* | (2006.01) |
| *C07C 233/43* | (2006.01) |
| *G16B 50/30* | (2019.01) |
| *G16B 50/10* | (2019.01) |
| *G16B 50/20* | (2019.01) |
| *C07C 237/22* | (2006.01) |
| *C07D 417/02* | (2006.01) |

(52) U.S. Cl.
CPC .......... *C07D 265/36* (2013.01); *C07C 233/43* (2013.01); *C07C 237/22* (2013.01); *C07C 311/29* (2013.01); *C07D 231/56* (2013.01); *C07D 309/34* (2013.01); *C07D 405/14* (2013.01); *C07D 413/12* (2013.01); *C07D 417/02* (2013.01); *C07D 417/12* (2013.01); *G16B 50/10* (2019.02); *G16B 50/20* (2019.02); *G16B 50/30* (2019.02)

(58) Field of Classification Search
CPC .. C07D 265/36; C07D 231/56; C07D 309/34; C07D 405/14; C07D 417/12; C07D 413/12; C07D 417/02; C07C 233/43; C07C 311/29; C07C 237/22; G16B 50/30; G16B 50/10; G16B 50/20; A61P 35/00
See application file for complete search history.

(56) References Cited

U.S. PATENT DOCUMENTS

2007/0054899 A1 3/2007 Park et al.

FOREIGN PATENT DOCUMENTS

EP 0574992 12/1993

OTHER PUBLICATIONS

CAS entry for 1445723-38-5 (Year: 2013).*
Akhtar et al., "Cytochrome b5 modulation of 17α hydroxylase and 17-20 lyase (CYP17) activities in steroidogenesis", Journal of Endocrinology, No. 187, 2005, Great Britain, pp. 267-274.
Bharatham et al., "Binding mode analyses and pharmacophore model developments for sulfonamide chalcone derivatives, a new class of α-glucosidase inhibitors", Journal of Molecular Graphics and Modelling, No. 26, 2008, Korea, pp. 1202-1212.
(Continued)

*Primary Examiner* — Kortney L. Klinkel
*Assistant Examiner* — Jason Deck
(74) *Attorney, Agent, or Firm* — Grossman, Tucker, Perreault & Pfleger, PLLC

(57) ABSTRACT

The invention provides compounds for use as medicaments, which act by inhibiting CYP17A1 and CYP19A1 enzymes. The compounds have particular application in the treatment of cancer especially prostate cancer and breast cancer. The compounds have the formula: [Chem. 1] wherein: R is independently selected from the group consisting of optionally substituted arylamide; optionally substituted alkylarylamide; optionally substituted aryl carboxamide; optionally substituted cyanopiperidine; optionally substituted oxopiperidine; optionally substituted N-(pyridin-3-yl); optionally substituted pyridin-3-yl; optionally substituted pyrazole-4-carboxamide; optionally substituted pyrimidin-4-ylcarboxamide; optionally substituted pyrimidin-4-ylcarboxamide; optionally substituted 1H-pyrrol-2-ylcarboxamide; optionally substituted morpholin carboxamide; optionally substituted 1H-indazol-3-ylcarboxamide; optionally substituted 5-cyanopiperidin-3-ylcarboxamide; optionally substituted quinolin-7-yl; optionally substituted pyrazin-2-ylcarboxamide; optionally substituted 1H-1,3-benzodiazole-6-carboxamide; and optionally substituted 3-oxo-3,4-dihydro-2H-1,4-benzoxazin-7-ylcarboxamide; Each R1, R2, R3, R4, R5 is independently selected from the group consisting of H; OH; a halogen atom; OCH$_3$; and NH$_2$; and X is independently selected from the group consisting of O, H and OH. Some of the compounds are claimed per se and the invention also encompasses pharmaceutically acceptable salts, solvates, hydrates, primary metabolites and prodrugs thereof.

8 Claims, 12 Drawing Sheets
(12 of 12 Drawing Sheet(s) Filed in Color)

(56) References Cited

OTHER PUBLICATIONS

Bheemanapalli et al., "Pharmacophore Based 3D-QSAR Study of Biphenyl Derivatives as Nonsteroidal Aromatase Inhibitors in JEG-3 Cell Lines", Medicinal Chemistry, vol. 9, No. 7, 2013, Bentham Science Publishers, pp. 974-984.
Bruno et al., "Synthesis and biological evaluations of putative metabolically stable analogs of VN/124-1 (TOK-001) Head to head anti-tumor efficacy evaluation of VN/124-1 (TOK-001) and abiraterone in LAPC-4 human prostate cancer xenograft model", Steroids, No. 76, 2011, Pennsylvania, 1268-1279.
Budha et al., "Pharmacokinetically-Guided Lead Optimization of Nitrofuranylamide Anti-Tuberculosis Agents", The AAPS Journal, vol. 10, No. 1, 2008, pp. 157-165.
Dai et al., "Syntheses and QSAR Studies of Benzylimidazole Derivatives and Benzylcarbazole as Potential Aromatase Inhibitors", Asian Journal of Chemistry, vol. 26, Issue 8, 2014, China,1 page.
Devore et al., "Structures of cytochrome P450 17A1 with prostate cancer drugs abiraterone and TOK-001", Nature, vol. 482, 2012, Kansas, pp. 116-120.
Dixon et al., "PHASE: a new engine for pharmacophore perception, 3D QSAR model development, and 3D database screening: 1. Methodology and preliminary results", Journal of Computer-Aided Molecular Design, 2006, vol. 20, Issue 10-11, pp. 647-671.
Easton et al., "Where are the prostate cancer genes?—A summary of eight genome wide searches", The Prostate, No. 57, 2003, United Kingdom, pp. 261-269.
Ferraldeschi et al., "Agents That Target Androgen Synthesis in Castration-Resistant Prostate Cancer", The Cancer Journal, vol. 19—Issue 1, 2013, United Kingdom, pp. 34-42.
Gianti et al., "Modeling Androgen Receptor Flexibility: A Binding Mode Hypothesis of CYP17 Inhibitors/Antiandrogens for Prostate Cancer Therapy", Journal of Chemical Information and Modeling, No. 52, 2012, Pennsylvania, pp. 2670-2683.
Haider et al., "Effects of novel 17α-hydroxylase/C17, 20-lyase (P450 17, CYP 17) inhibitors on androgen biosynthesis in vitro and in vivo", Journal of Steroid Biochemistry & Molecular Biology, No. 84, 2003, Germany, pp. 555-562.
Haider et al., "Molecular Modeling on Inhibitor Complexes and Active-Site Dynamics of Cytochrome P450 C17, a Target for Prostate Cancer Therapy", J. Mol. Biol. No. 400, 2010, United Kingdom, pp. 1078-1098.
Handratta et al., "Novel C-17-Heteroaryl Steroidal CYP17 Inhibitors/Antiandrogens: Synthesis, in Vitro Biological Activity, Pharmacokinetics, and Antitumor Activity in the LAPC4 Human Prostate Cancer Xenograft Model", J. Med. Chem., No. 48, 2005, Maryland, pp. 2972-2984.
Hu et al., "Replacement of Imidazolyl by Pyridyl in Biphenylmethylenes Results in Selective CYP17 and Dual CYP17/CYP11B1 Inhibitors for the Treatment of Prostate Cancer", J. Med. Chem. No. 53, 2010, Germany, pp. 5749-5758.
"Induced Fit Docking", Schroedinger Software Release 2015-2, Schroedinger Press, pp. 1-80.
Jagusch et al., "Synthesis, biological evaluation and molecular modelling studies of methyleneimidazole substituted biaryls as inhibitors of human 17a-hydroxylase-17,20-lyase (CYP17). Part I: Heterocyclic modifications of the core structure", Bioorganic & Medicinal Chemistry, No. 16, 2008, Germany, pp. 1992-2010.
Kaku et al., "Discovery of orteronel (TAK-700), a naphthylmethylimidazole derivative, as a highly selective 17,20-lyase inhibitor with potential utility in the treatment of prostate cancer", Bioorganic & Medicinal Chemistry, No. 19, 2011, Japan, pp. 6383-6399.
Kaku et al., "17,20-Lyase inhibitors. Part 3: Design, synthesis, and structure-activity relationships of biphenylylmethylimidazole derivatives as novel 17,20-lyase inhibitors", Bioorganic & Medicinal Chemistry, No. 19, 2011, Japan, pp. 2428-2442.

Kishore et al., "Pharmacophore-Based 3D-QSAR Studies of Aromatase Inhibitors", Asian Journal of Chemistry, vol. 25, Issue 18, 2013, pp. 10588-10594.
Lippolis et al., "A high-density tissue microarray from patients with clinically localized prostate cancer reveals ERG and TATI exclusivity in tumor cells", Prostate Cancer and Prostatic Disease No. 16, 2013, Sweden, pp. 145-150.
McConnel, "Physiologic basis of endocrine therapy for prostatic cancer", The Urologic Clinics of North America, 1991, vol. 18, 1 pg.
Mendieta et al., "Highly Potent and Selective Nonsteroidal Dual Inhibitors of CYP17/CYP11B2 for the Treatment of Prostate Cancer To Reduce Risks of Cardiovascular Diseases", J. Med. Chem. No. 56, 2013, pp. 6101-6107.
Miller, "Molecular Biology of Steroid Hormone Synthesis", Endocrine Reviews, vol. 9, Issue 3, 1988, California, pp. 295-318.
Nnane et al., "Inhibition of Androgen Synthesis in Human Testicular and Prostatic Microsomes and in Male Rats by Novel Steroidal Compounds", Endocrinology, vol. 140, No. 6, 1999, Maryland, pp. 2891-2897.
Park et al., "Discovery of novel a-glucosidase inhibitors based on the virtual screening with the homology-modeled protein structure", Bioorganic & Medicinal Chemistry, No. 16, 2008, Korea, pp. 284-292.
Rafferty et al., "Highly-selective 4-(1,2,3-triazole)-based P450c17a 17,20-lyase inhibitors", Bioorganic & Medicinal Chemistry Letters, No. 24, 2014, North Carolina, pp. 2444 2447.
Roy et al., "Classical and 3D-QSAR studies of cytochrome 17 inhibitor imidazolesubstituted biphenyls", Journal Molecular Simulation, vol. 36, Issue 4, 2010, 2pgs.
Salvador et al., "Steroidal 5α-reductase and 17α-hydroxylase/17,20-lyase (CYP17) inhibitorsuseful in the treatment of prostatic diseases", Journal of Steroid Biochemistry & Molecular Biology, vol. 137, 2013, Portugal, pp. 199-222.
Schaefer et al., "Distinct ERG rearrangement prevalence in prostate cancer: higher frequency in young age and in low PSA prostate cancer", Prostate Cancer and Prostatic Disease, vol. 16, 2013, Austria, pp. 132-138.
Sherman et al., "Novel Procedure for Modeling Ligand/Receptor Induced Fit Effects", J. Med. Chem. vol., 49, 2006, New York, pp. 534-553.
Sherman et al., "Use of an Induced Fit Receptor Structure in Virtual Screening", Chem Biol Drug Des, vol. 67, 2006, New York, pp. 83-84.
CAS Registry No. 1445723-38-5; STN entry date: Jul. 19, 2013; Chemical name: Benzamide, 2-chloro-N-[3-[[(6-chloro-3,4-dihydro-3-oxo-2H-1,4-benzoxazin-7-yl)amino ]methyl]phenyl]-, 1 pg.
CAS Registry No. 1797677-20-3; STN entry date: Jul. 10, 2015; Chemical name: 2H-I , 4-Benzoxazin-3( 4H)-one, 7-[[[3-(3-pyridinyl)phenyl]methyl]amino ]-, 1 pg.
CAS Registry No. 1832317-56-2; STN entry date: Dec. 19, 2015; Chemical name: Benzamide, 2-chloro-N-[3-[[(3,4-dihydro-3-oxo-2H-I,4-benzoxazin-7-yl)amino ]methyl]phenyl]-, 1 pg.
Vasaitis et al., "CYP17 inhibitors for prostate cancer therapy", Journal of Steroid Biochemistry & Molecular Biology vol. 125, 2011, Pennsylvania, pp. 23-31.
Yap et al., "Targeting CYP17: established and novel approaches in prostate cancer", Current Opinion in Pharmacology, vol. 8, 2008, United Kingdom, pp. 449-457.
Yin et al., "CYP17 inhibitors—abiraterone, C17,20-lyase inhibitors and multi-targeting agents", Nature Reviews Urology, vol. 11, 2014, Germany, pp. 32-42.
Yin et al., "Recent Progress in Pharmaceutical Therapies for Castration-Resistant Prostate Cancer", Int. J. Mol. Sci., vol. 14, 2013, Germany, pp. 13958-13978.
Zhu et al., "Targeting the Adrenal Gland in Castration-Resistant Prostate Cancer: A Case for Orteronel, a Selective CYP-17 17,20-Lyase Inhibitor", Curr Oncol Rep, vol. 15, 2013, New York, pp. 105-112.
International Search Report from corresponding PCT Appln. No. PCT/ZA2016/050041, dated Mar. 28, 2017.
Written Opinion from corresponding PCT Appln. No. PCT/ZA2016/050041, dated Mar. 28, 2017.

(56) References Cited

OTHER PUBLICATIONS

International Search Report from related PCT Appln. No. PCT/ZA2016/050042, dated Jun. 29, 2017.
Written Opinion from related PCT Appln. No. PCT/ZA2016/050042, dated Jun. 29, 2017.
CAS Registry No. 561018-92-6; STN entry date: Aug. 5, 2003; Chemical Name: 1 H-Pyrrole-3-carboxylic acid, 2,4-dimethyl-5-[2-[( 4-methyl-2-oxo-2H-1-benzopyran-7-yl)oxy ]acetyl]-, ethyl ester, 1 pg.
CAS Registry No. 745802-54-4; STN entry date: Sep. 16, 2004; Chemical Name: 2H-Pyran-3-carboxamide, N-( 4-ethylphenyl)-5-(2-hydroxy-5-methoxybenzoyl)-2-immo-, 1 pg.
CAS Registry No. 782459-47-6; STN entry date: Nov. 17, 2004; Chemical Name: Ethanone, 1-( 4-acetyl-3,5-dimethyl- IH-pyrrol-2-yl)-2-[[ 4-[2-( I-methylethyl)phenyl]-5-(3-pyridinyl)-4H-I,2,4-triazol-3-yl]thio ]-, 1 pg.
CAS Registry No. 785704-47-4; STN entry date: Nov. 21, 2004; Chemical Name: Acetamide, 2-[( 4,5-dihydro-5-oxo-4-propyl- IH-1,2,4-triazol-3-yl)thio ]N-[(3,4-dimethoxyphenyl)methyl]-, 1 pg.
CAS Registry No. 871263-93-3; STN entry date: Jan. 5, 2006; Chemical Name: 4(3H)-Pyrimidinone, 2-[[2-[2,5-dimethyl-I -(5-methyl-3-isoxazolyl)-1 Hpyrrol-3-yl]-2-oxoethyl]thio ]-6-propyl-, 1 pg.
CAS Registry No. 878972-36-2; STN entry date: Apr. 2, 2006; Chemical Name: 6-Quinoxalinecarboxamide, l-ethyl-N-[(3-fluoro-4-methoxyphenyl)methyl]-1,2,3,4-tetrahydro-N-methy 1-2,3-dioxo-, 1 pg.
CAS Registry No. 1010572-83-4; STN entry date: Mar. 28, 2008; Chemical Name: 5-Thiazoleacetamide, 2-[[2-( IH-indol-3-yl)-2-oxo- I-phenylethyl]thio ]-4-methyl-, 1 pg.
CAS Registry No. 1013310-47-8; STN entry date: Apr. 10, 2008; Chemical Name: 1 H-Indazole-3-carboxylic acid, I-methyl-2-oxo-2-[4-[(I-oxobutyl)amino ]phenyl]ethyl ester, 1 pg.
CAS Registry No. 1090431-17-6; STN entry date: Dec. 26, 2008; Chemical Name: Acetamide, N-[ (2-chlorophenyl)methyl]-2-[[ 4-(2-furanylmethyl)-5-( 1 H-indol-3-yl)-4 H-1,2,4-triazol-3-yl]thio ]-, 1 pg.
CAS Registry No. 1241067-91-3; STN entry date: Sep. 15, 2010; Chemical Name: Benzoic acid, 2-amino-3-methyl-, 2-[4-( aminosulfonyl)phenoxy ]ethyl ester, 1 pg.
CAS Registry No. 1252049-79-8; STN entry date: Nov. 9 201 O; Chemical Name: Benzeneacetamide, a-[[3-[(2-methoxy-1-oxopropyl)amino ]phenyl]amino ]-, 1pg.

\* cited by examiner

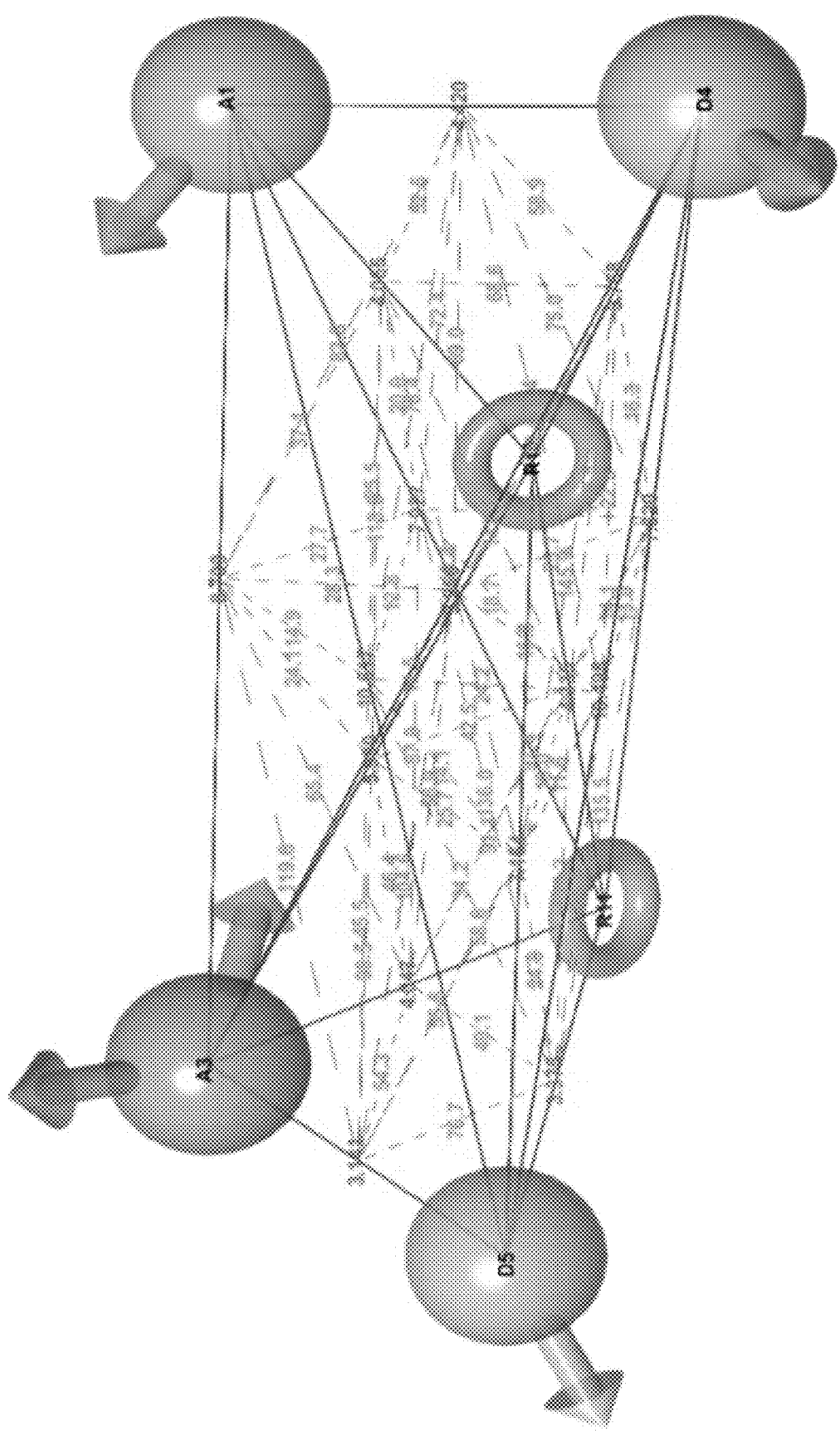
[Fig. 1]

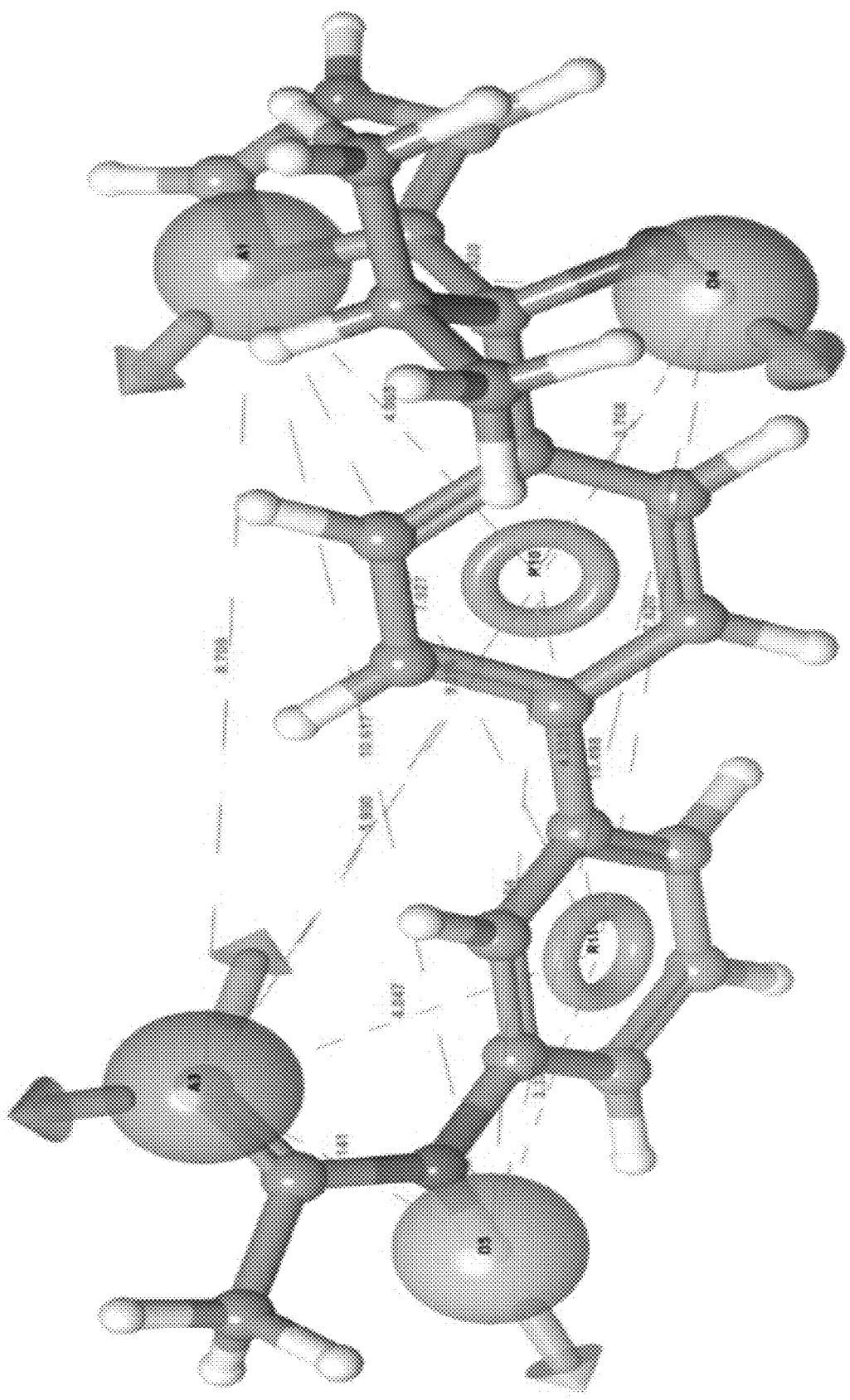
[Fig. 2]

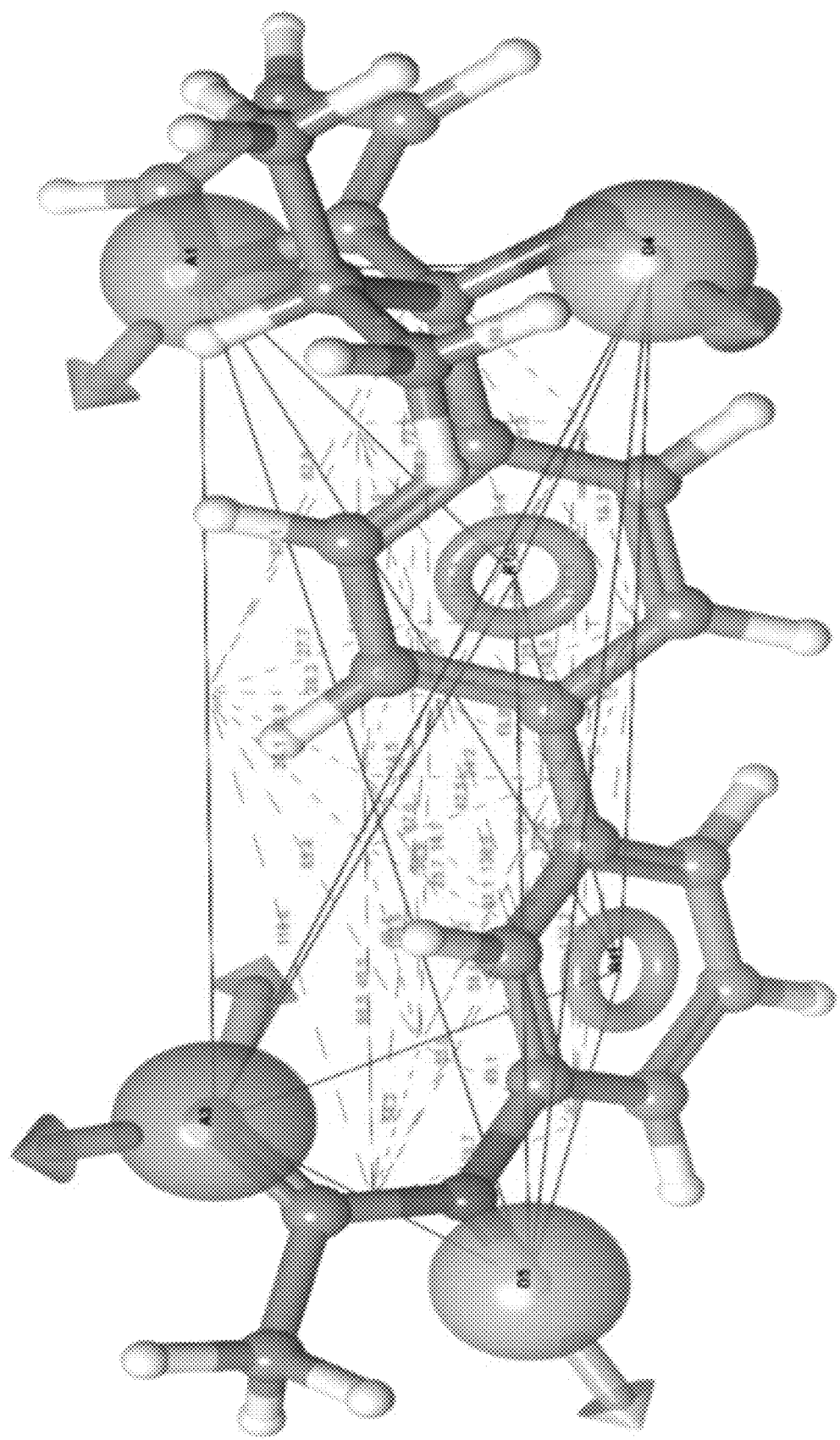
[Fig. 3]

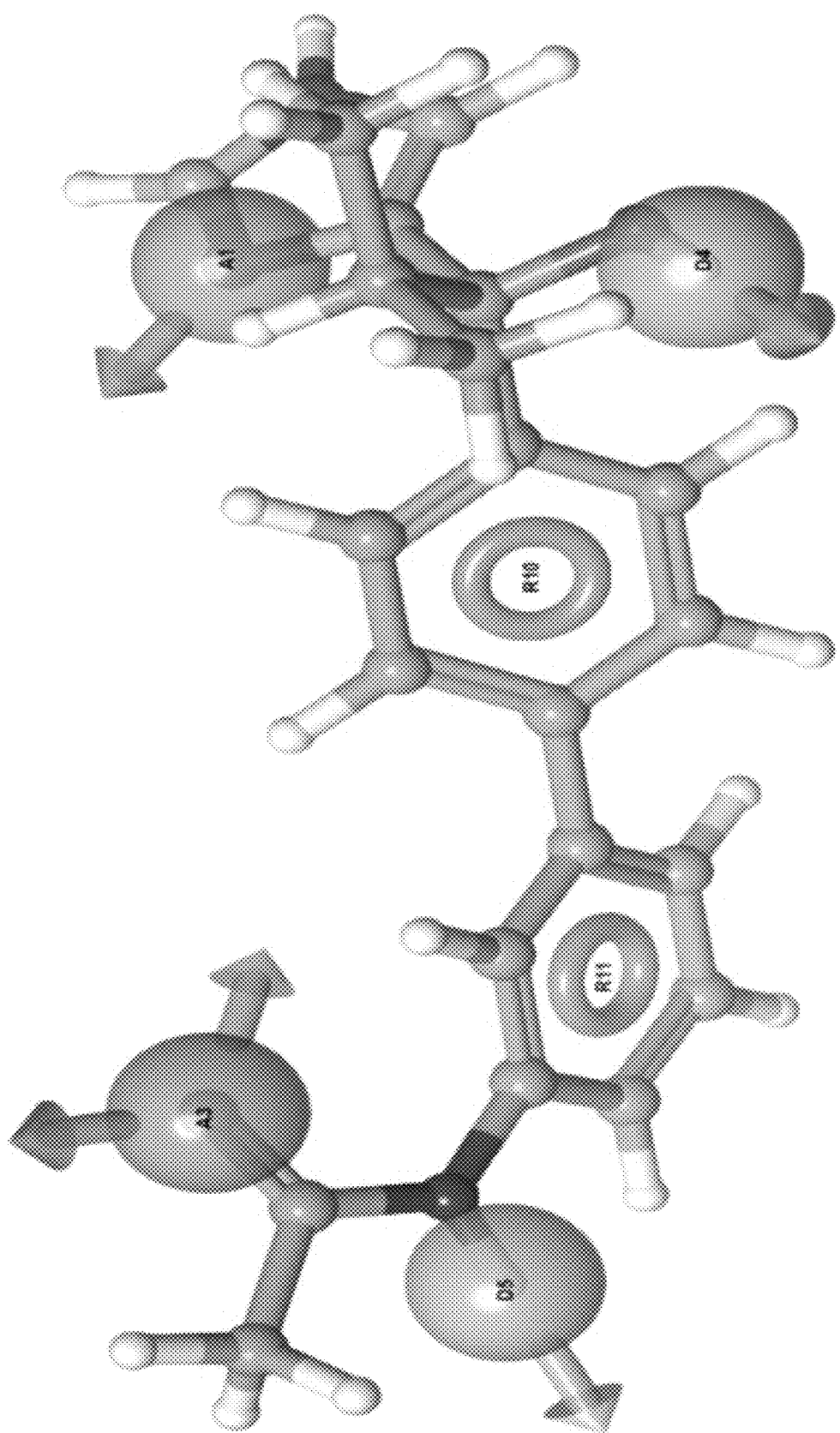
[Fig. 4]

[Fig. 5.1]
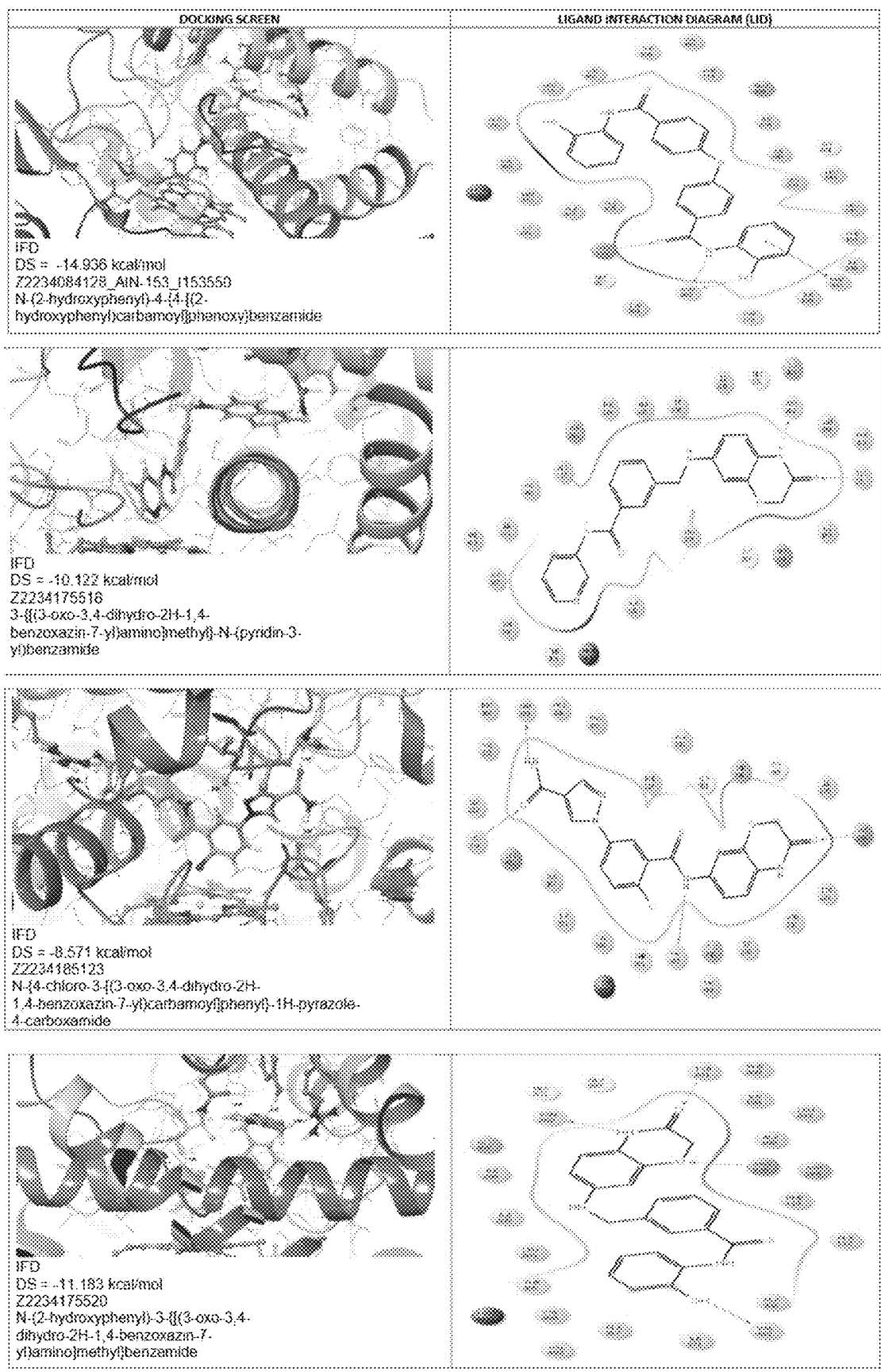

[Fig. 5.2]
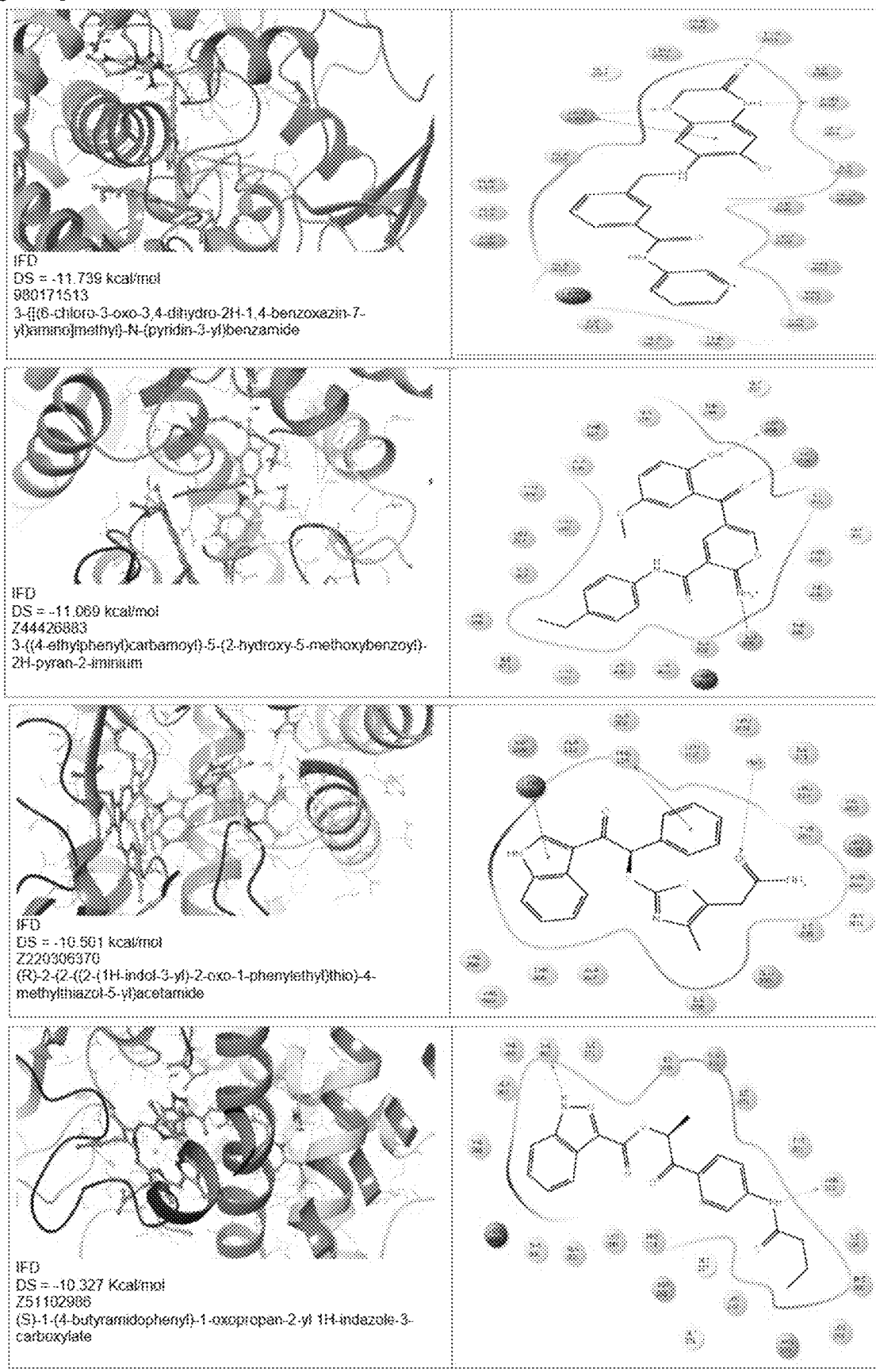

[Fig. 5.3]
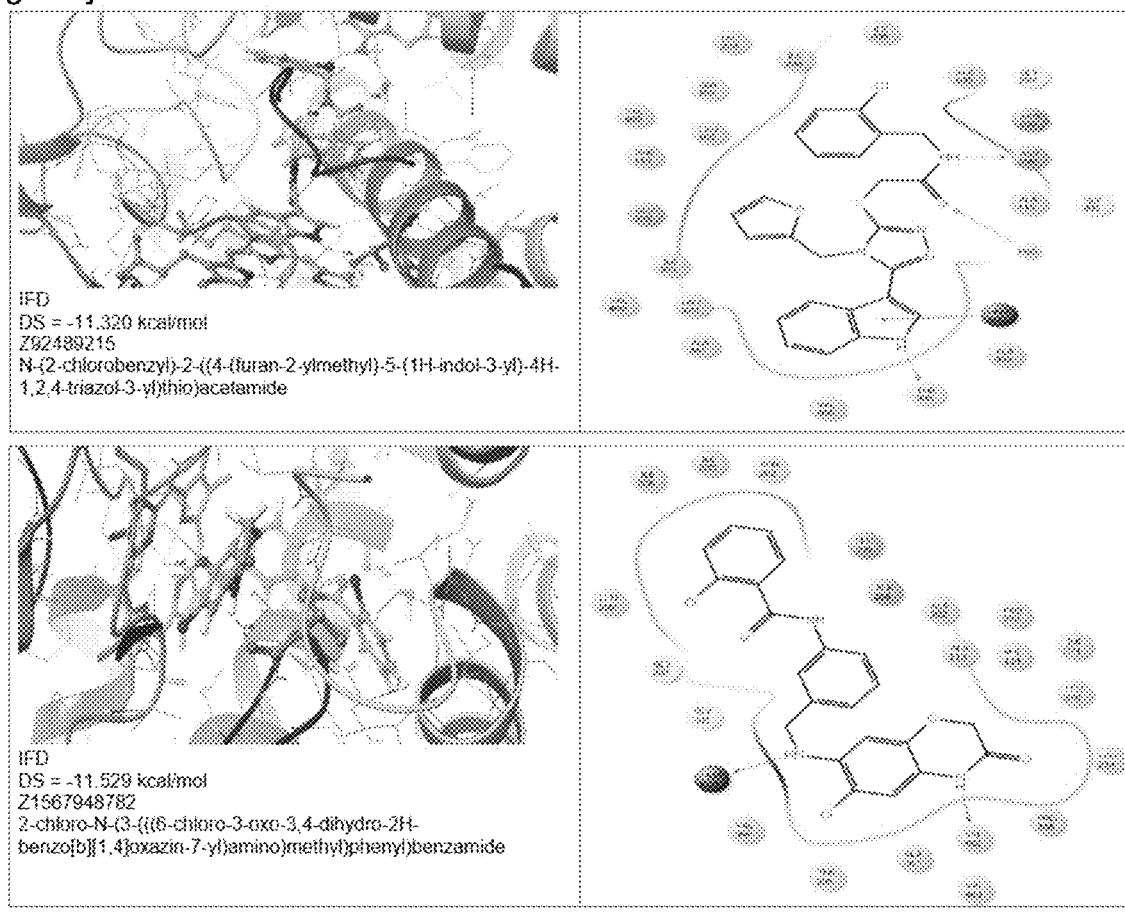

[Fig. 6.1]
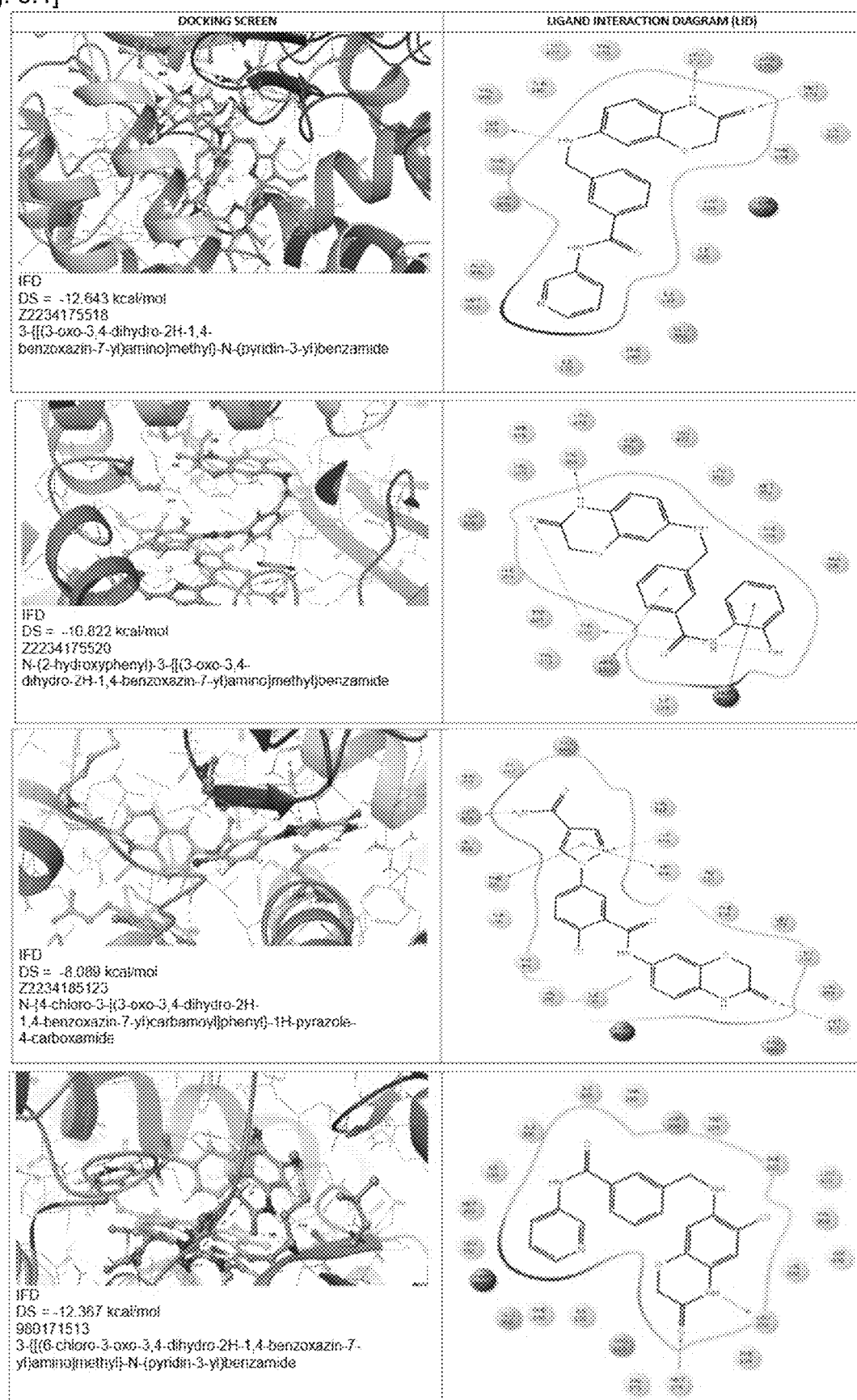

[Fig. 6.2]
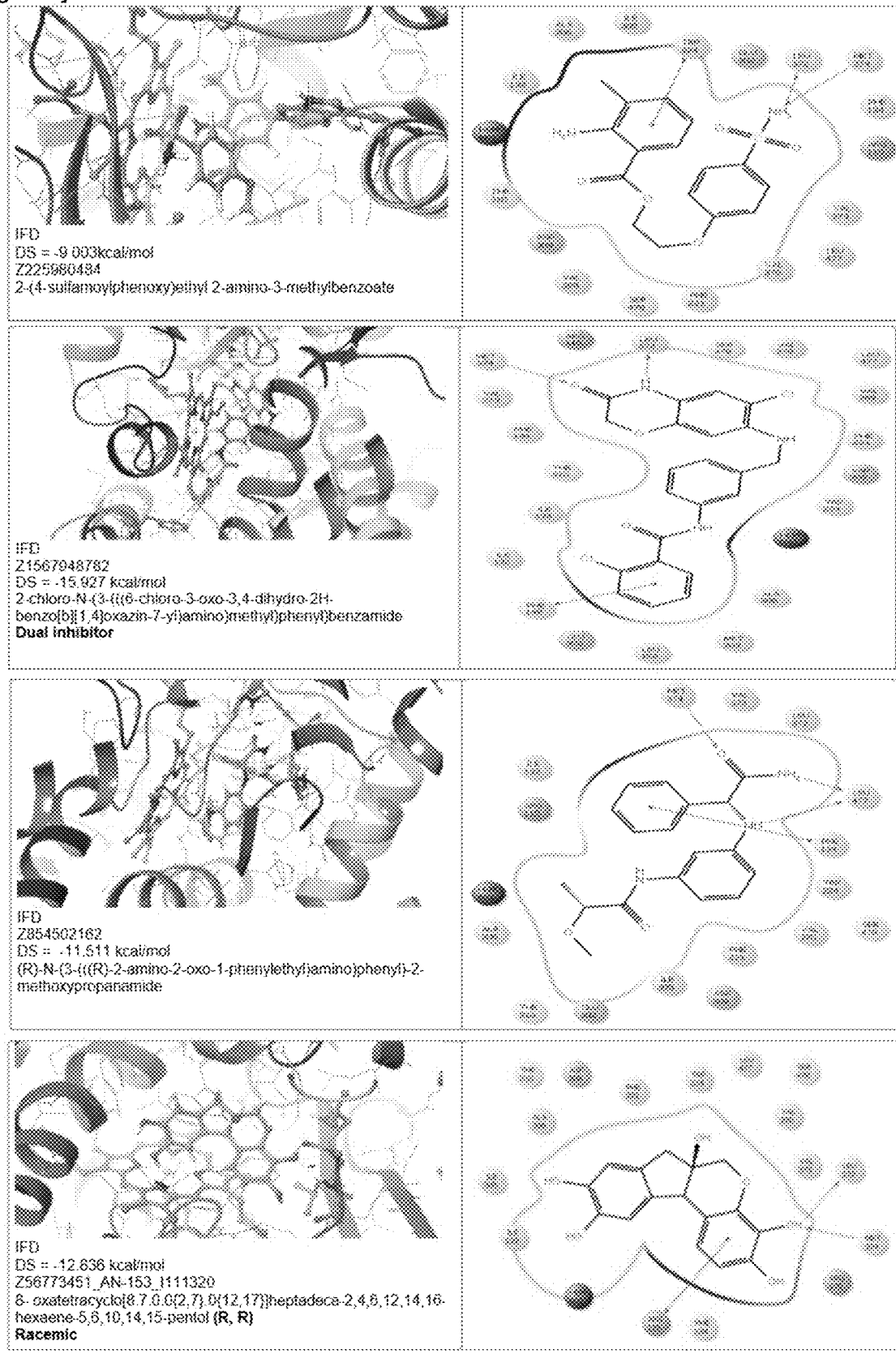

[Fig. 6.3]
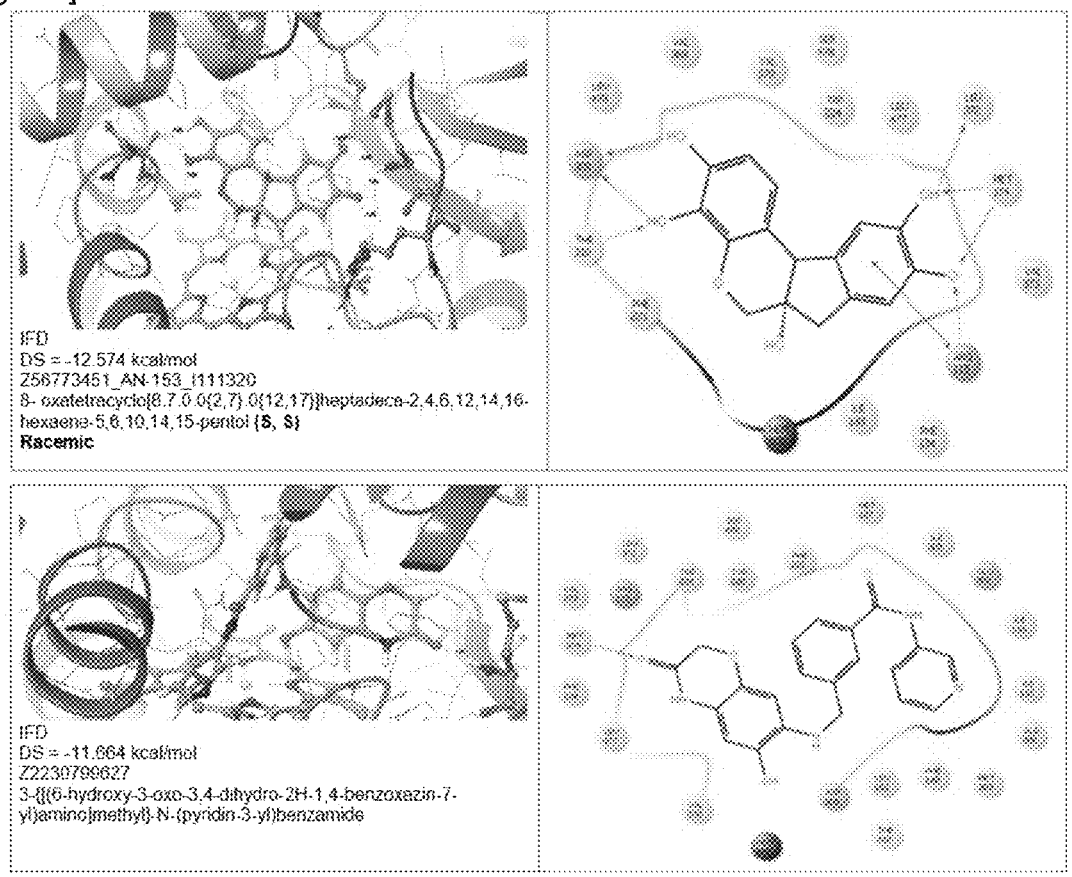
[Fig. 7]
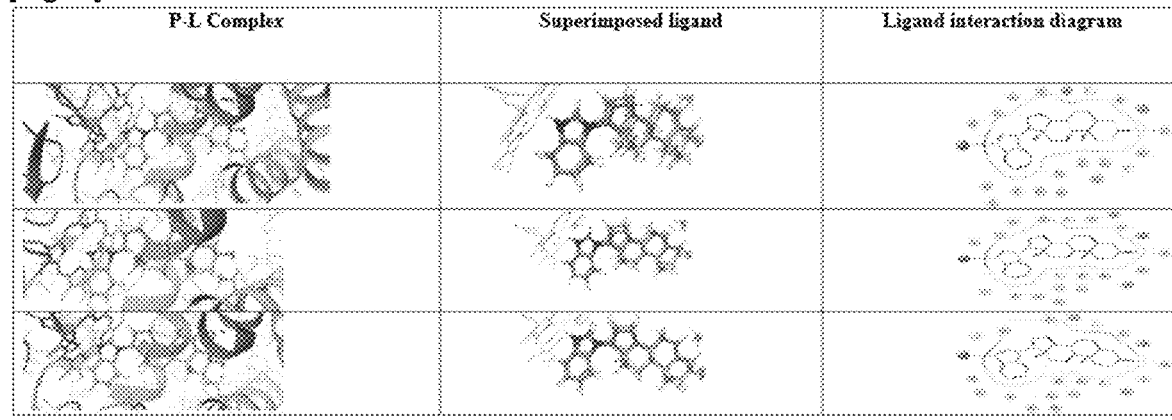

[Fig. 8]
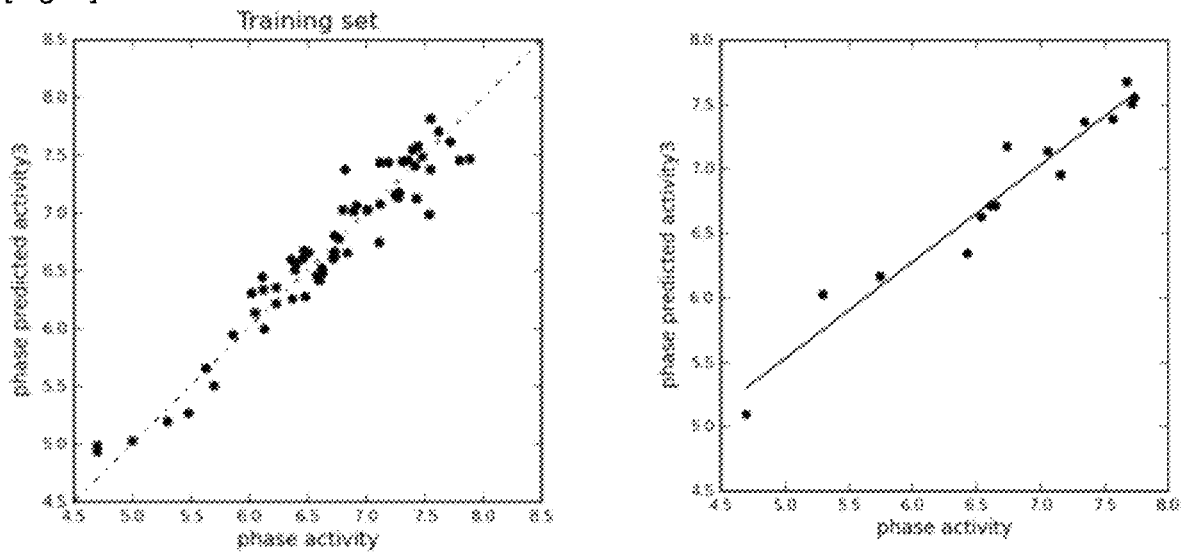
[Fig. 9.1]
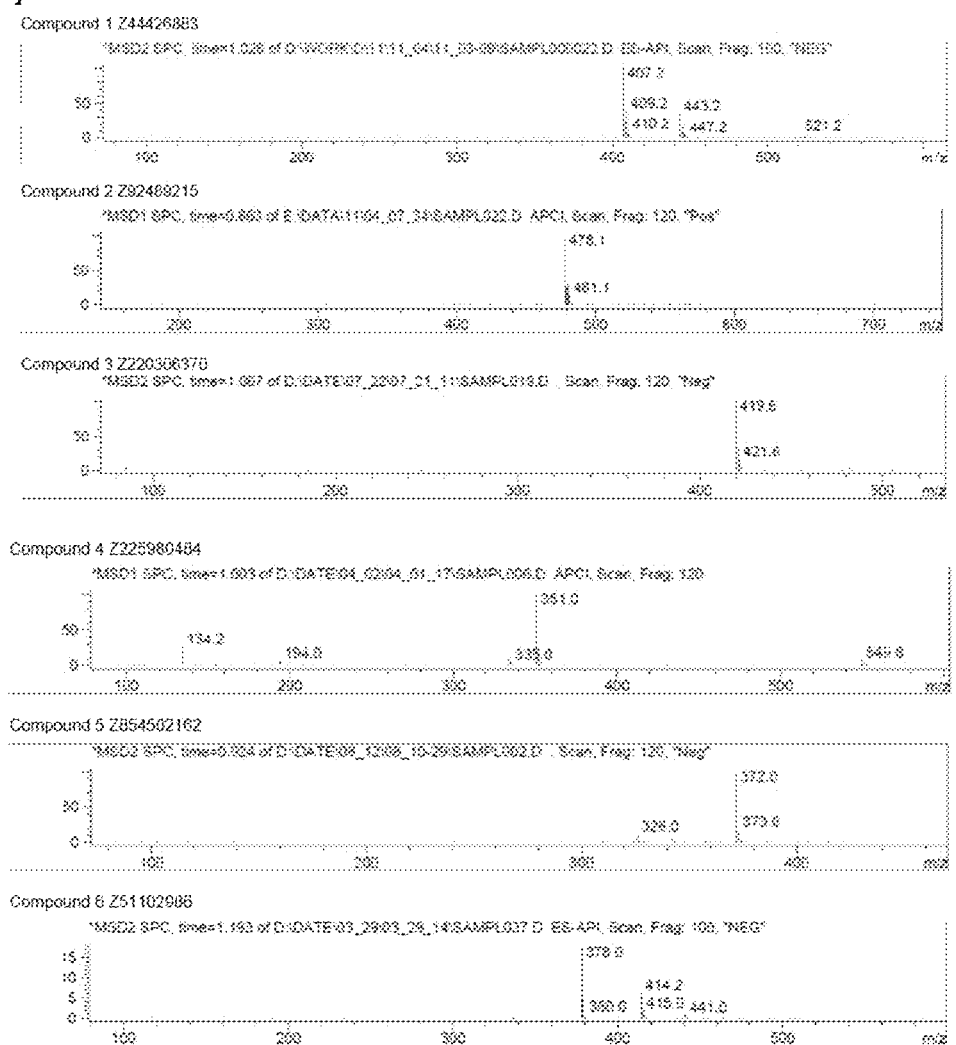

[Fig. 9.2]
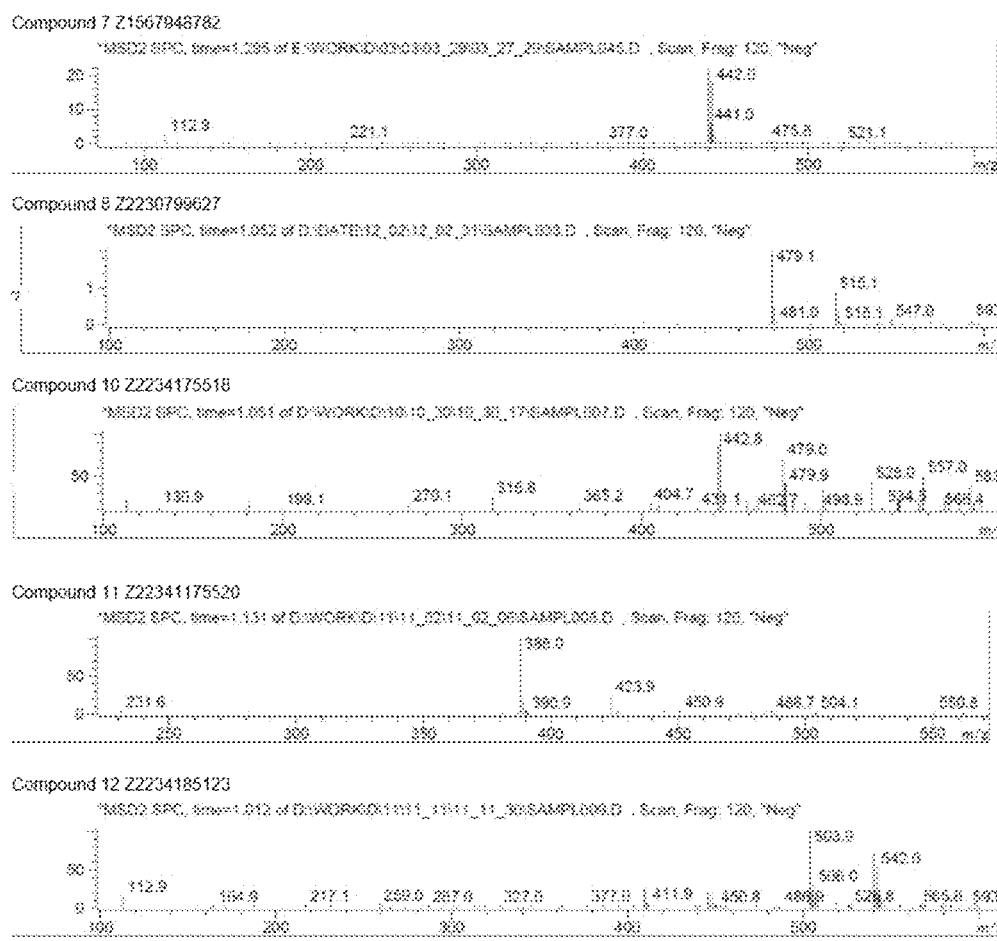

PHARMACOPHORES, COMPOUNDS AND METHODS HAVING APPLICATION IN THE TREATMENT OF CANCER THROUGH INHIBITION OF CYP17A1 AND CYP19A1

TECHNICAL FIELD

THIS INVENTION concerns the inhibition of key enzymes which catalyze the biosynthesis of androgens. It concerns, inter alia, the design, identification and biological activities of potent and selective non-steroidal inhibitors of CYP17A1 and CYP19A1 enzymes. CYP17A1 and CYP19A1 are important enzymes for steroid hormone biosynthesis and inhibition of these enzymes is used to treat androgen-dependent cancers such as prostate cancer and breast cancer.

For purposes of this invention, 3D-QSAR pharmacophore models were developed using a training set of active compounds. Flexible docking techniques were also used. The pharmacophore models which were developed are one aspect of this invention. The invention also provides various compounds which exhibited inhibitory activity against the enzymes in question. These compounds provide a shortlist which may be further refined for use in compositions and methods of inhibiting cell proliferation of cancers, and methods of preventing or treating cancer. The invention also provides a process of using pharmacophores to screen for compounds that exhibit inhibitory activity against the enzymes in question.

Definitions

"CYP17A1": Unless the context indicates otherwise, this term is used in this specification to refer to the CYP17A1 enzyme rather than to its encoding gene (Cytochrome P450, family 17, subfamily A, polypeptide 1). Thus, the term CYP17A1 refers to Cytochrome P450 17A1, otherwise known as steroid 17-alpha-monooxygenase, 17α-hydroxylase, 17, 20-lyase and/or 17, 20-desmolase.

"CYP19A1": Unless the context indicates otherwise, this term is used in this specification to refer to the CYP19A1 enzyme (otherwise known as aromatase) rather than to its encoding gene (Cytochrome P450, family 19, subfamily A, polypeptide 1).

"Dual Inhibitor" means an inhibitor of both CYP17A1 and CYP19A1.

"3D-QSAR" means 3-Dimensional Quantitative Structure-Activity Relationships.

"Comprises/comprising" when used in this specification is taken to specify the presence of stated features, integers, steps or components but does not preclude the presence or addition of one or more other features, integers, steps or components or groups thereof.

Reference Numbers and Letters for Compounds: The claims appended to this description are to be considered as an integral part of the present disclosure. Reference numbers and letters shown in the claims (e.g. "[Compound 1; Z44426883]") serve to facilitate the correlation of integers of the claims with compounds described in the specification, but are not intended to restrict in any way the language of the claims unless the contrary is clearly apparent from the context.

R Groups

Where a number of options are defined for R and no attachment points are described or illustrated for those options, then unless the contrary is clearly apparent from the context these options shall be considered to be attached in the same manner as shown in the examples herein described (in particular Compounds 7, 8, 10, 11, 12, 13 and 12.8 to 12.28).

BACKGROUND

Most prostate and breast cancers are hormone dependent. The dependence of prostate cancer (PC) on androgen signaling has been recognized for many decades, yet PC remains a leading cause of male death in the Western world.

As prostate cancer cells proliferate in response to androgen steroids, CYP17A1 inhibition is a strategy to prevent androgen synthesis and treat lethal metastatic castration-resistant prostate cancer (CRPC).

The CYP17A1 and CYP19A1 enzymes have similar catalytic cycles. They catalyze the biosynthesis of steroid hormones. Non-steroidal and steroidal therapeutic strategies are known. Known CYP17A1 inhibitors acting along the androgen-synthesis pathway include Ketoconazole, Abiraterone, Galeterone (TOK-001 or VN/124-1) and Orteronel (TAK-700).

The CYP17A1 enzyme catalyzes two major routes involved in steroid biosynthesis viz. 17α-hydroxylase and 17,20-lyase activities. In the first step, the substrates progesterone and pregnenolone are hydroxylated in the 17α-position of the substrates to form 17α-hydroxyprogesterone and 17α-hydroxypregnenolone, respectively. In the second step, the 17,20-lyase activities break the C17-C20 bonds of 17α-hydroxyprogesterone to yield dehydroepiandrosterone (DHEA). The main advantage of CYP17A1 inhibitors is that they hinder androgen biosynthesis in the testicles and adrenals as well as the formation of intracellular androgens in cancer cells.

The CYP19A1 enzyme catalyzes a three-step A-ring aromatization of androstenedione to give estrone. CYP19A1 also catalyzes oxidation of testosterone to estradiol. The first step is formation of 19-hydroxytestosterone, which in turn is oxidized to 19-oxotestosterone and then to estradiol, similar to androstenedione catabolism to estrone.

Another steroid substrate which undergoes a CYP19A1-catalyzed three-step aromatization is 16alpha-hydroxyandrostenedione. The final product of that oxidation is 16alpha-hydroxyestrone.

There is substantial evidence that breast cancer (BC) tissue contains all the enzymes responsible for the local biosynthesis of estrogens from circulating precursors, and it is well established that increased exposure to local estrogens is an important risk factor in the genesis and growth of breast cancer. CYP19A1 inhibition can therefore serve as a strategy for treating breast cancer.

Apart from CYP17A1 and CYP19A1, the group of CYP450 enzymes involved in steroid biosynthesis also includes the following: CYP11A1 involved in cholesterol side chain cleavage, CYP21 involved in steroid-21-hydroxylase activities, CYP11B1 involved in steroid-11-beta-hydroxylase activities, and CYP11B2 involved in aldosterone-synthase activities. However, inhibition of CYP11A1 and CYP21 is not suitable as a drug target since the former affects the biosynthesis of all steroid hormones while the latter is involved in the biosynthesis of gluco- and mineralocorticoids.

The known steroid inhibitor Abiraterone acetate inhibits CYP17A1 and has been shown to improve overall survival in CRPC. However, Abiraterone is a 'promiscuous' drug that interacts with a number of targets, leading to adverse effects and toxicities. It is not well absorbed and its pharmacokinetics are not optimal.

Other drugs have also been developed with similar inhibitory properties. For an overview of the state of the art in this field reference may be made to citations PTL1 to PTL5 and NPL1 to NPL7 as set out at the foot of this patent specification.

Despite recent advances made in this field, new therapeutic strategies are urgently needed and the development of new CYP17A1 and CYP19A1 inhibitors is required as an additional line of defense. Multi-targeting strategies to affect androgen synthesis and signaling at different points would also be advantageous; thus there is a need for dual inhibitors (i.e. compounds which can inhibit the activity of two or more enzymes, for example compounds capable of inhibiting both CYP17A1 and CYP19A1).

SUMMARY OF INVENTION

This invention entailed the development of pharmacophores from which compounds useful for the inhibition of CYP17A1 and CYP19A1 were identified and synthesized.

The pharmacophore may comprise features selected from the group consisting of:

benzoxazin, phenoxybenzamides, carboxamides, benzoyl-carbamoyl, methylthiazoles, phenylmethyl-thiothiazoles, butyramidophenyl, sulfamoylphenoxy, phenylmethoxypropanamides, and oxatetra cycloheptadeca hexaene.

The pharmacophore model may comprise a hypothesis AADDRR.860 having a configuration as shown in FIGS. 1 to 3 of the accompanying drawings, wherein:

A represents hydrogen bond acceptors;
D represents hydrogen bond donors; and
R represents aromatic rings.

According to further aspect of the invention there is provided the use of said pharmacophore model AADDRR.860 as a 3D-QSAR pharmacophore model to search for similarity in terms of pharmacophore features of new chemical entities (NCEs) and/or for screening and identification of candidate compounds to be used for CYP17A1 and CYP 19A1 inhibition.

The following Table 1 tabulates statistical data for said pharmacophore model AADDRR.860:

TABLE 1

| Statistical data for a 3D-QSAR pharmacophore model: | | | | | | | | | |
|---|---|---|---|---|---|---|---|---|---|
| No. | Hypothesis ID | # PLS Factors | SD | $R^2$ | F | P | Stability | RMSE | $Q^2$ | Pearson-R |
| 12 | AADDRR.860 | 1 | 0.4551 | 0.6178 | 98.6 | 2.328e−014 | 0.9263 | 0.4356 | 0.7538 | 0.9104 |
| | | 2 | 0.2955 | 0.8415 | 159.3 | 1.002e−024 | 0.6890 | 0.4034 | 0.7888 | 0.9189 |
| | | 3 | 0.2080 | 0.9228 | 234.9 | 9.29e−033 | 0.6389 | 0.2841 | 0.9400 | 0.9720 |

Various aspects of the invention are discussed under two main headings, firstly those aspects relating to the pharmacophores and secondly those aspects relating to the compounds which have been identified and their application as medicaments.

Pharmacophores

According to a first aspect of the invention there is provided a pharmacophore for use in the design, screening and identification of inhibitors of CYP17A1 and CYP19A1 enzymes, said pharmacophore having the following spatial arrangement of atoms within a molecule:

two hydrogen bond acceptors (referred to herein as A1 & A3);
two hydrogen bond donors (referred to herein as D4 & D5); and
two aromatic rings (referred to herein as R10 & R11);
wherein the distances between the centres of:
(A1) and (A3) is 8.71±0.05 Å;
(A1) and (D4) is 4.42±0.05 Å;
(D4) and (R10) is 3.77±0.05 Å;
(D4) and (A3) is 9.30±0.05 Å;
(D4) and (R11) is 7.62±0.05 Å;
(D4) and (D5) is 10.41±0.05 Å;
(R10) and (A3) is 5.99±0.05 Å;
(R10) and (R11) is 4.34±0.05 Å;
(R10) and (A1) is 4.06±0.05 Å;
(R10) and (D5) is 7.16±0.05 Å;
(R11) and (D5) is 3.38±0.05 Å;
(R11) and (A3) is 4.05±0.05 Å;
(R11) and (A1) is 7.93±0.05 Å;
(D5) and (A3) is 3.14±0.05 Å; and
(D5) and (A1) is 10.62±0.05 Å.

The pharmacophore may include a heterocyclic compound having at least one fused biaryl and/or tetraaryl group.

The preferred 3D-QSAR pharmacophore model was AADDRR.860 with $R^2$ 0.9228 and $Q^2$ 0.9400 after outlier removal of 22 structures using a leave-n-out-cross validation method.

The preferred pharmacophore model was mapped onto a reference ligand N-{4'-[1-Hydroxy-1-(1H-imidazol-4-yl)-2-methylpropyl][1,1'-biphenyl]-3-yl}acetamide (Compound 7 in Table 4 below; 17[12] in Table 4A) with a fitness score of 3.0 which fits the model. This alignment symbolizes a good match of features present in the reference ligand to the pharmacophore model.

Accordingly, in a further aspect of the invention there is provided the use of N-{4'-[1-Hydroxy-1-(1H-imidazol-4-yl)-2-methylpropyl][1,1'-biphenyl]-3-yl}acetamide in a training set as a reference ligand in a method of designing, screening and identifying inhibitors of an enzyme selected from the group consisting of CYP17A1 and CYP19A1.

In certain embodiments this invention provides a method for designing, screening and identifying candidate compounds for CYP17A1 inhibition, said method comprising the following steps:

(a) providing a database of candidate compounds comprising drug-like molecules;
(b) generating 3D descriptors for said candidate compounds;
(c) predetermining a set of filtering criteria and comparing said generated descriptors against said filtering criteria thereby to select and to reject candidate compounds within said database that, respectively, satisfy or do not satisfy said criteria;
(d) providing a pharmacophore model as described herein and fitting said selected compounds against said model, thereby to identify compounds exhibiting a fit which satisfies a best-fit threshold; and (e) predicting the activity value of said compounds satisfying said best-fit threshold.

According to a further aspect of the invention there is provided a process for design, screening and identification of candidate compounds for inhibition of CYP17A1 and/or CYP19A1, which includes the following steps:
(a) compiling a training set and a test set, each such set comprising compounds of known CYP17A1 inhibition (the training set may comprise of approximately 105 such compounds);
(b) generating a dataset of 3D conformers for each of the compounds in said training set;
(c) correlating each of the compounds of said training set with an observed pIC50 value of CYP17A1 inhibition;
(d) generating from said dataset of conformers in step (b) a set of pharmacophore hypotheses;
(e) calculating the CYP17A1 inhibitory activity of each conformer generated in step (b) by establishing an alignment cost of the pharmacophore hypothesis in respect of a reference ligand with a fitness score ranging from 2.5 to 3.0 inclusive (preferably approximately 3.0) in the training and test datasets;
(f) finding the fitness score of at least one of said candidate compounds to be screened, with reference to the pharmacophore of the present invention;
(g) calculating the regression coefficient for each pharmacophore hypothesis in the training and test sets; and
(h) choosing a best fit model with $R^2$ (ranging from 0.92-0.99) & $Q^2$ (ranging from 0.90-0.99) for both the training and test sets, respectively.

The root-mean-square deviation (RMSD) for any compound (ligand) in the training and test data sets from said reference ligand may advantageously be set at 1.50 Å.

According to yet a further aspect of the invention there is provided a process for design, screening and identification of inhibitors of CYP17A1, said process including the steps of:
(a) compiling a dataset of chemically diverse active ligands known to have pIC50>7.00 (preferably those known to have a pIC50>7.54, i.e. an IC50>29 nM) in respect of CYP17A1;
(b) generating a set of three-dimensional structures for possible tautomerization/ionization states (typically at approximately pH 7.4), stereoisomers and conformers ("conformations") of said active ligands in said dataset and compiling a conformation dataset comprising said conformations;
(c) establishing pharmacophore sites by identifying pharmacophore features in each said conformation and mapping them to specific locations in said conformations, said features including features selected from the group consisting of hydrogen bond acceptors (A), hydrogen bond donors (D), negatively charged groups (N), positively charged groups (P), hydrophobic groups (H) and aromatic rings (R);
(d) finding a plurality of pharmacophore hypotheses by performing a search for common pharmacophores corresponding to said conformation dataset; said search spanning pharmacophore variants presenting with said pharmacophore sites;
(e) scoring said plurality of pharmacophore hypotheses by assessing relative conformational energies of conformations within the conformation dataset, such that said conformations fit said hypotheses with a fitness score in a range from 2.5 to 3.5 (preferably=approx. 3.0), thereby to select a reference ligand from the conformation dataset;
(f) building a QSAR pharmacophore model; this step typically involving, for each compound to be mapped onto a pharmacophore, conversion of said compound into a three-dimensional configuration and storing all of its conformations with energies in appropriate computational software, which may then be operated to perform calculations which compare the three-dimensional conformers of the compound being mapped and the pharmacophore with experimental activities;
(g) randomly or quasi-randomly selecting a plurality of structures to comprise a training set and a test set in order to validate said model, the selection process involving (i) selecting a random or quasi-random fraction of the ligands for the training set by specifying a percentage of the structures to be included in the training set and randomly or quasi-randomly selecting said specified percentage of structures from the existing data set and assigning them to the training set; and (ii) assigning the remainder of the structures in the existing data set to the test set.
(h) preparing a 3D structural database containing all-atom 3D structures of drug-like molecules with molecular properties that are consistent with criteria suitable for potential drug-like molecules, said database being searchable for matches to said QSAR pharmacophore model;
(i) generating tautomers and/or ionization states for said 3D structures and removing high energy tautomerization and/or ionization states from said 3D structural database;
(j) searching for matches to said QSAR pharmacophore model within said 3D structural database by screening said database, thereby to generate a matching set of hits;
(k) selecting low-energy conformers of said hits by geometry optimization and performing conformational searches of said low-energy conformers;
(l) using output files of hits from said geometry optimization and conformational searches as a source of ligands as inputs ("input ligands");
(m) preparing enzymes from a database of x-ray crystal structures;
(n) carrying out Virtual Screening to perform rigid receptor-flexible ligand docking to drug-like molecules from said 3D structural database as a filtering criteria for selecting a subset of said drug-like molecules with docking scores employed as a quantitative measure of the affinity of the drug-like molecules to said prepared enzymes; and
(o) carrying out Induced Fit Docking (IFD) in respect to said subset of drug-like molecules, and compiling a dataset of said molecules which exhibit a fit under said IFD to serve as a dataset of potential CYP17A1 and/or CYP19A1 inhibitors.

The process may involve the following subsidiary steps:
(a) advantageously, the number of site points may be chosen to be 6, preferably matching 4 of the active groups of the most active structures in the dataset (and matches for the hypothesis may be established by matching all of said 6 site points in the hypothesis).
(b) the available parameters for pharmacophore features may be set as follows: A=2, D=2, H=2 and R=3.
(c) the hypothesis selected for use in the search may be AADDRR.860.
(d) the reference ligand may comprise N-{4'-[1-Hydroxy-1-(1H-imidazol-4-yl)-2-methylpropyl][1,1'-biphenyl]-

3-yl}acetamide (Compound 7 in Table 4; 17[12] in Table 4A), which is part of the training set and can also be seen in FIGS. 2 to 4.

(e) the step of selecting low energy conformers may be based on relative potential energy threshold of less than 0.5 kcal/mol.

(f) the step of preparing enzymes from x-ray crystal structures may involve selection of an oxidation state of +3 for Fe of porphyrin.

(g) the Virtual Screening step may comprise High Throughput Virtual Screening Workflow (HTVSW).

Compounds

In a further aspect, the invention provides compounds as tabulated in the following Tables 2 & 2A, for use as medicaments. Several of the compounds are inhibitors of CYP17A1 and/or CYP19A1 and accordingly have application in the treatment of cancer, typically (i) prostate cancer and/or (ii) breast cancer. Some of the compounds are also understood to be novel and inventive per se.

TABLE 2

Inhibitors of CYP17A1 and/or CYP19A1 for use in the treatment of Prostate Cancer and Breast Cancer:

| # | Compound ID & Inhibition Activity | IUPAC Name & Molecular Formula | DS CYP17A1 (kcal/mol) | DS CYP19A1 (kcal/mol) | CYP17A1 $IC_{50}$ (μM) | CYP19A1 $IC_{50}$ (μM) | CYP1A2 $IC_{50}$ (μM) | CYP2C9 $IC_{50}$ (μM) | CYP2C19 $IC_{50}$ (μM) | CYP2D6 $IC_{50}$ (μM) | CYP3A4 $IC_{50}$ (μM) |
|---|---|---|---|---|---|---|---|---|---|---|---|
| 1 | Z44426883 CYP17A1 inhibition only | N-(4-ethylphenyl)-5-(2-hydroxy-5-methoxybenzoyl)-2-imino-2H-pyran-3-carboxamide $C_{22}H_{21}N_2O_5^+$ | −10.046 | | >50 | | 27.9 | 6.1 | 14.9 | 36.3 | 14.6 |

Structural Formula:

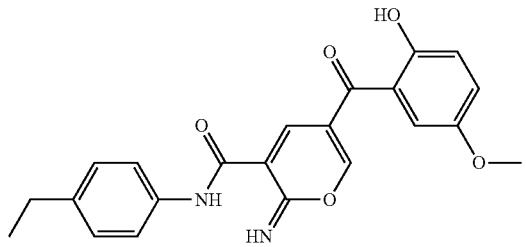 [SMILES: CCc1ccc(NC(=O)c2cc(C(=O)c3cc(OC)ccc3O)coc2=N)cc1]

| 2 | Z92489215 CYP17A1 inhibition only | N-[(2-chlorophenyl)methyl]-2-({4-[(furan-2-yl)methyl]-5-(1H-indol-3-yl)-4H-1,2,4-triazol-3-yl}sulfanyl)acetamide $C_{24}H_{20}ClN_5O_2S$ | −11.32 | | >50 | | 4.5 | 1.8 | 3.5 | 8.1 | 1.1 |

Structural Formula:

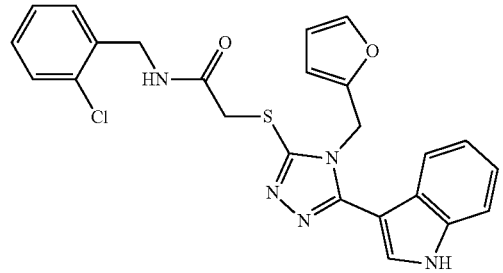 [SMILES: O=C(CSc1nnc(-c2c[nH]c3ccccc23)n1Cc1ccco1)NCc1ccccc1Cl]

TABLE 2-continued

Inhibitors of CYP17A1 and/or CYP19A1 for use in the treatment of Prostate Cancer and Breast Cancer:

| # | Compound ID & Inhibition Activity | IUPAC Name & Molecular Formula | DS CYP17A1 (kcal/mol) | DS CYP19A1 (kcal/mol) | CYP17A1 $IC_{50}$ (μM) | CYP19A1 $IC_{50}$ (μM) | CYP1A2 $IC_{50}$ (μM) | CYP2C9 $IC_{50}$ (μM) | CYP2C19 $IC_{50}$ (μM) | CYP2D6 $IC_{50}$ (μM) | CYP3A4 $IC_{50}$ (μM) |
|---|---|---|---|---|---|---|---|---|---|---|---|
| 3 | Z220306370 CYP17A1 inhibition only | 2-(2-{[2-(1H-indol-3-yl)-2-oxo-1-phenylethyl]sulfanyl}-4-methyl-1,3-thiazol-5-yl)acetamide $C_{22}H_{19}ClN_3O_2S_2$ | −10.509 | | >34.1 | | 12.6 | 1.5 | 8.3 | 15.0 | 2.7 |
| 4 | Z225980484 CYP19A1 inhibition only | 2-(4-sulfamoylphenoxy)ethyl 2-amino-3-methylbenzoate $C_{16}H_{18}N_2O_5S$ | | −9.003 | | 43.5 | nd* | 16.0 | 1.5 | | 3.3 |
| 5 | Z854502162 CYP19A1 inhibition only | N-(3-{[carbamoyl(phenyl)methyl]amino}phenyl)-2-methoxypropanamide $C_{18}H_{21}N_3O_3$ | | −11.511 | | >50 | >50 | >50 | >50 | >50 | >50 |

Structural Formula (Compound 3):

2-(2-{[2-(1H-indol-3-yl)-2-oxo-1-phenylethyl]sulfanyl}-4-methyl-1,3-thiazol-5-yl)acetamide Structural Formula (Compound 4):

Structural Formula (Compound 5):

TABLE 2-continued

Inhibitors of CYP17A1 and/or CYP19A1 for use in the treatment of Prostate Cancer and Breast Cancer:

| # | Compound ID & Inhibition Activity | IUPAC Name & Molecular Formula | DS CYP17A1 (kcal/mol) | DS CYP19A1 (kcal/mol) | CYP17A1 IC$_{50}$ (µM) | CYP19A1 IC$_{50}$ (µM) | CYP1A2 IC$_{50}$ (µM) | CYP2C9 IC$_{50}$ (µM) | CYP2C19 IC$_{50}$ (µM) | CYP2D6 IC$_{50}$ (µM) | CYP3A4 IC$_{50}$ (µM) |
|---|---|---|---|---|---|---|---|---|---|---|---|
| 6 | Z51102986 CYP17A1 inhibition only | 1-(4-butanamidophenyl)-1-oxopropan-2-yl-1H-indazole-3-carboxylate $C_{21}H_{21}N_3O_4$ | −10.939 | | >50 | | >50 | 2.5 | 41.2 | >50 | >50 |
| Structural Formula: | | | | | | | | | | | |
| 7 | Z1567948782 DUAL INHIBITOR | 2-chloro-N-(3-{[(6-chloro-3-oxo-3,4-dihydro-2H-1,4-benzoxazin-7-yl)amino]methyl}phenyl)benzamide $C_{22}H_{17}Cl_2N_3O_3$ | −11.529 | −15.927 | >50 | >25 | >50 | nd* | >50 | >50 | 0.7 |
| Structural Formula: | | | | | | | | | | | |

2-chloro-N-(3-{[(6-chloro-3-oxo-3,4-dihydro-2H-1,4-benzoxazin-7-yl)amino]methyl}phenyl)benzamide

| 8 | Z2230799627 CYP19A1 inhibition only | 3-{[(6-hydroxy-3-oxo-3,4-dihydro-2H-1,4-benzoxazin-7-yl)amino]methyl}-N-(pyridin-3-yl)benzamide $C_{21}H_{18}N_4O_4$ | −11.664 | | | 5.9 | 2.7 | 7.9 | 44.6 | >50 | 2.8 |
| Structural Formula: | | | | | | | | | | | |

TABLE 2-continued

Inhibitors of CYP17A1 and/or CYP19A1 for use in the treatment of Prostate Cancer and Breast Cancer:

| # | Compound ID & Inhibition Activity | IUPAC Name & Molecular Formula | DS CYP17A1 (kcal/mol) | DS CYP19A1 (kcal/mol) | CYP17A1 $IC_{50}$ (μM) | CYP19A1 $IC_{50}$ (μM) | CYP1A2 $IC_{50}$ (μM) | CYP2C9 $IC_{50}$ (μM) | CYP2C19 $IC_{50}$ (μM) | CYP2D6 $IC_{50}$ (μM) | CYP3A4 $IC_{50}$ (μM) |
|---|---|---|---|---|---|---|---|---|---|---|---|
| 9 | Z2234084128 CYP17A1 inhibition only | N-(2-hydroxyphenyl)-4-{3-[(2-hydroxyphenyl)carbamoyl]phenoxyl}benzamide $C_{26}H_{20}N_2O_5$ | −14.936 | | >50 | | >50 | >50 | >50 | >50 | >50 |
| Structural Formula: | | | | | | | | | | | |
| 10 | Z2234175518 DUAL INHIBITOR | 3-{[(3-oxo-3,4-dihydro-2H-1,4-benzoxazin-7-yl)amino]methyl}-N-(pyridin-3-yl)benzamide $C_{21}H_{18}N_4O_3$ | −10.122 | −12.643 | >50 | 5.7 | 2.1 | >50 | >50 | >50 | 6.6 |
| Structural Formula: | | | | | | | | | | | |
| 11 | Z2234175520 CYP19A1 inhibition only | N-(2-hydroxyphenyl)-3-{[(3-oxo-3,4-dihydro-2H-1,4-benzoxazin-7-yl)amino]methyl}benzamide $C_{22}H_{19}N_3O_4$ | −11.183 | −10.822 | | 8.6 | 26.9 | 4.0 | 7.6 | 2.7 | 8.3 |
| Structural Formula: | | | | | | | | | | | |

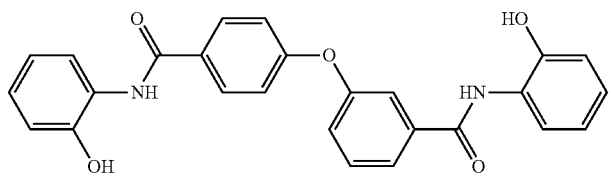 [SMILES: O=C(Nc1ccccc1O)c1ccc(Oc2cccc(C(=O)Nc3ccccc3O)c2)cc1]

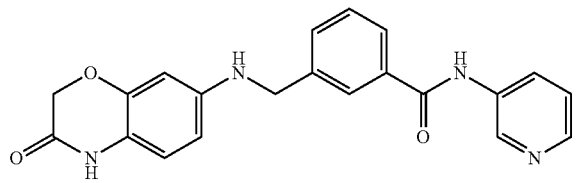 [SMILES: O=C1COc2cc(NCc3cccc(C(=O)Nc4cccnc4)c3)ccc2N1]

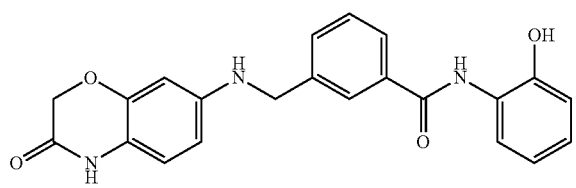 [SMILES: O=C1COc2cc(NCc3cccc(C(=O)Nc4ccccc4O)c3)ccc2N1]

TABLE 2-continued

Inhibitors of CYP17A1 and/or CYP19A1 for use in the treatment of Prostate Cancer and Breast Cancer:

| # | Compound ID & Inhibition Activity | IUPAC Name & Molecular Formula | DS CYP17A1 (kcal/mol) | DS CYP19A1 (kcal/mol) | CYP17A1 IC$_{50}$ (μM) | CYP19A1 IC$_{50}$ (μM) | CYP1A2 IC$_{50}$ (μM) | CYP2C9 IC$_{50}$ (μM) | CYP2C19 IC$_{50}$ (μM) | CYP2D6 IC$_{50}$ (μM) | CYP3A4 IC$_{50}$ (μM) |
|---|---|---|---|---|---|---|---|---|---|---|---|
| 12 | Z2234185123 DUAL INHIBITOR | N-{4-chloro-3-[(3-oxo-3,4-dihydro-2H-1,4-benzoxazin-7-yl)carbamoyl]phenyl}-1H-pyrazole-4-carboxamide C$_{19}$H$_{14}$ClN$_5$O$_4$ | −8.571 | −8.089 | >50 | 0.06 | >50 | 22.5 | >50 | >50 | 18.3 |
| Structural Formula: | | | | | | | | | | | |
| 13 | Z518027752 (previously named 980171513) DUAL INHIBITOR | 3-{[(6-chloro-3-oxo-3,4-dihydro-2H-1,4-benzoxazin-7-yl)amino]methyl}-N-(pyridin-3-yl)benzamide C$_{21}$H$_{17}$ClN$_4$O$_3$ | −11.739 | −12.367 | >50 | 14.5 | 0.6 | nd* | >50 | >50 | 1.1 |
| Structural Formula: | | | | | | | | | | | |

(Key: The acronym "DS" means Docking Score and relates to binding energies.)

It will be noted that five (5) of the compounds in Table 2 are CYP17A1 inhibitors only, four (4) are CYP19A1 inhibitors only, and four (4) are Dual Inhibitors, i.e. inhibitors of both CYP17A1 and CYP19A1. The Dual Inhibitors are Compounds 7, 10, 12, 13.

Thus, in a further aspect, this invention provides Dual Inhibitors, being compounds for direct inhibition of both the CYP17A1 and the CYP19A1 enzymes, said compounds being selected from the group consisting of Compounds 7, 10, 12, 13 in Table 2 (Column "#").

In a further aspect this invention provides compounds for direct inhibition of CYP17A1, said compounds being selected from the group consisting of Compounds 1, 2, 3, 6, 7, 9, 10, 12, 13 as tabulated in Table 2 (Column "#").

In yet a further aspect, this invention provides compounds for direct inhibition of CYP19A1, said compounds being selected from the group consisting of compounds 4, 5, 7, 8, 10, 11, 12, 13 as tabulated in Table 2 (Column "#").

It will be appreciated that pharmaceutically preferred molecules will be those which have favourable binding affinities together with low IC$_{50}$ values for inhibition of the target enzymes (CYP17A1 or CYP19A1). Advantageously they should also show high IC$_{50}$ values for inhibition of enzymes which are required for metabolism.

As can be seen from Table 2, structures 7, 8, 10, 11, 12, 13 showed the lowest IC$_{50}$ values against CYP19A1 (sub-micromolar inhibitory potency levels).

Structures 1, 2, 3, 6, 7, 9, 10 showed an inhibitory potency of CYP17A1 at micromolar levels.

The compounds in Table 2 were also tested for inhibition of metabolic enzymes CYP1A2, CYP2C9, CYP2C19, CYP2D6, and CYP3A4. The resulting IC$_{50}$ values are tabulated in Table 2. Structures 1, 2, 3, 4, 11 and 13 inhibit various CYP450 isoforms and therefore cannot be co-administered with the inhibitors of these isoforms, to prevent drug-drug interactions.

Toxicity studies conducted on the molecules in Table 2 revealed that structures 5, 6, 7, 8, 9, 10 and 12 have excellent safety profiles, and structures 1, 2, 3, 4, 11 and 13 have reasonably good safety profiles.

Structures 1, 2, 3, 4, 5, 6 and 9 have different chemical scaffolds. Structures 7 to 13 share a common chemical scaffold (Compounds 8 to 13 being derivatives of parent compound 7).

In addition to the compounds in Table 2, a series of further derivatives of the Compound 12 were developed as shown in the following Table 2A.

TABLE 2A

Derivatives of Compound Z2234185123 (Compound 12 in Table 2) as additional Inhibitors of CYP17A1 and/or CYP19A1 for use in the treatment of Prostate Cancer and Breast Cancer:

| # | Compound ID | IUPAC Name & Structural Formula |
|---|---|---|
| 12.1 | Z106939358 | 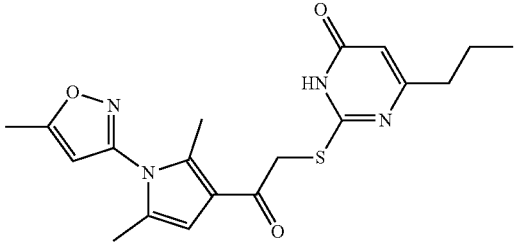<br>2-({2-[2,5-dimethyl-1-(5-methyl-1,2-oxazol-3-yl)-1H-pyrrol-3-yl]-2-oxoethyl}sulfanyl)-6-propyl-3,4-dihydropyrimidin-4-one |
| 12.2 | Z18477425 | 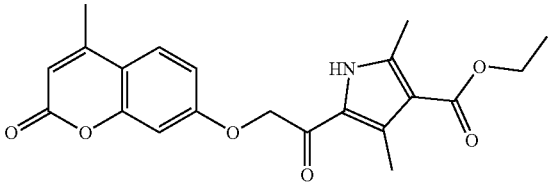<br>ethyl 2,4-dimethyl-5-{2-[(4-methyl-2-oxo-2H-chromen-7-yl)oxy]acetyl}-1H-pyrrole-3-carboxylate |
| 12.3 | Z18624177 | 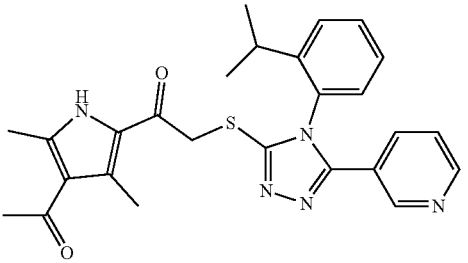<br>1-(4-acetyl-3,5-dimethyl-1H-pyrrol-2-yl)-2-({4-[2-(propan-2-yl)phenyl]-5-(pyridin-3-yl)-4H-1,2,4-triazol-3-yl}sulfanyl)ethan-1-one |
| 12.4 | Z18716406 | 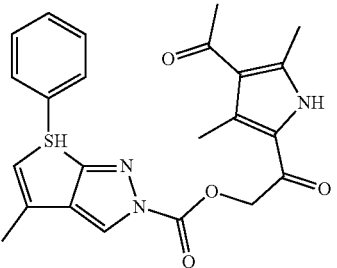<br>2-(4-acetyl-3,5-dimethyl-1H-pyrrol-2-yl)-2-oxoethyl 3-methyl-1-phenyl-1H-thieno[2,3-c]pyrazole-5-carboxylate |

TABLE 2A-continued

Derivatives of Compound Z2234185123 (Compound 12 in Table 2) as additional Inhibitors of CYP17A1 and/or CYP19A1 for use in the treatment of Prostate Cancer and Breast Cancer:

| # | Compound ID | IUPAC Name & Structural Formula |
|---|---|---|
| 12.5 | Z57017139 | 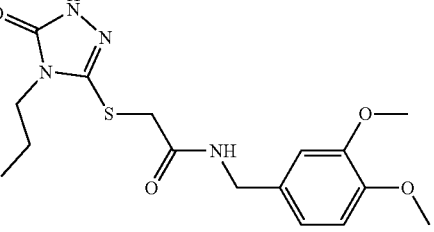<br>N-[(3,4-dimethoxyphenyl)methyl]-2-[(5-oxo-4-propyl-4,5-dihydro-1H-1,2,4-triazol-3-yl)sulfanyl]acetamide |
| 12.6 | Z67738761 | 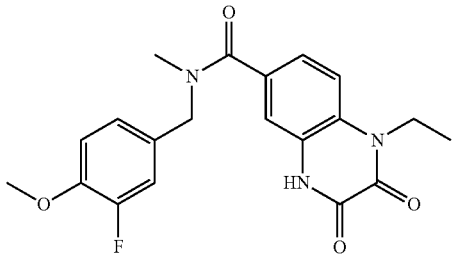<br>1-ethyl-N-[(3-fluoro-4-methoxyphenyl)methyl]-N-methyl-2,3-dioxo-1,2,3,4-tetrahydroquinoxaline-6-carboxamide |
| 12.7 | Z827252794 | 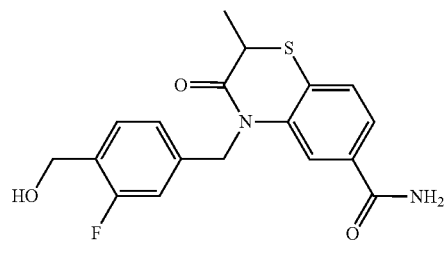<br>N-{[3-fluoro-4-(hydroxymethyl)phenyl]methyl}-2-methyl-3-oxo-3,4-dihydro-2H-1,4-benzothiazine-6-carboxamide |
| 12.8 | Z2670000119 | 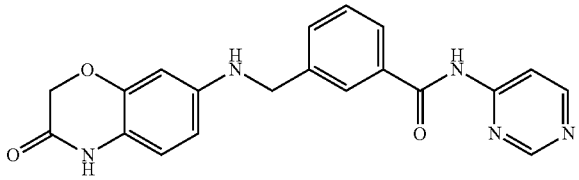<br>3-{[(3-oxo-3,4-dihydro-2H-1,4-benzoxazin-7-yl)amino]methyl}-N-(pyrimidin-4-yl)benzamide |
| 12.9 | Z2670000121 | 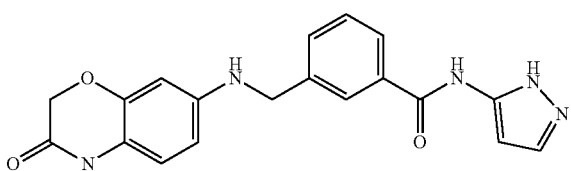<br>3-{[(3-oxo-3,4-dihydro-2H-1,4-benzoxazin-7-yl)amino]methyl}-N-(1H-pyrazol-5-yl)benzamide |

TABLE 2A-continued

Derivatives of Compound Z2234185123 (Compound 12 in Table 2) as
additional Inhibitors of CYP17A1 and/or CYP19A1 for use in the treatment of
Prostate Cancer and Breast Cancer:

| # | Compound ID | IUPAC Name & Structural Formula |
|---|---|---|

12.10  Z2670000123

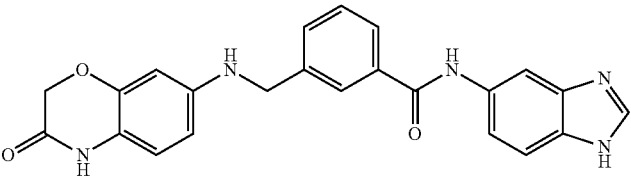

N-(1H-1,3-benzodiazol-5-yl)-3-{[(3-oxo-3,4-dihydro-2H-1,4-benzoxazin-7-yl)amino]methyl}benzamide 12.11  Z2670000126

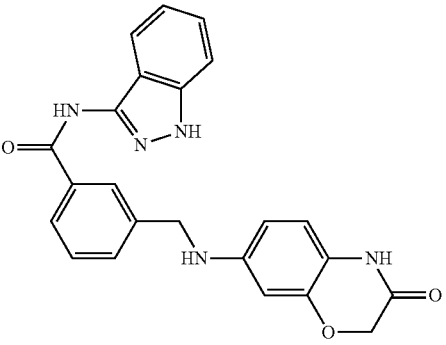

N-(1H-indazol-3-yl)-3-{[(3-oxo-3,4-dihydro-2H-1,4-benzoxazin-7-yl)amino]methyl}benzamide 12.12  Z2670000128

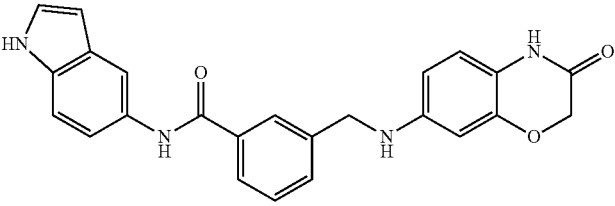

N-(1H-indol-5-yl)-3-{[(3-oxo-3,4-dihydro-2H-1,4-benzoxazin-7-yl)amino]methyl}benzamide 12.13  Z2670000131

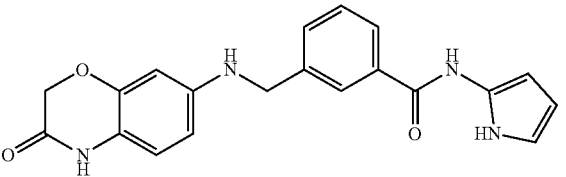

3-{[(3-oxo-3,4-dihydro-2H-1,4-benzoxazin-7-yl)amino]methyl}-N-(1H-pyrrol-2-yl)benzamide 12.14  Z2670000141

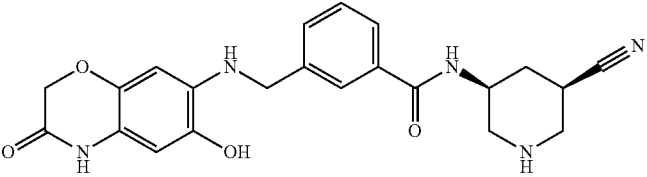

N-[(3S,5R)-5-cyanopiperidin-3-yl]-3-{[(6-hydroxy-3-oxo-3,4-dihydro-2H-1,4-benzoxazin-7-yl)amino]methyl}benzamide TABLE 2A-continued Derivatives of Compound Z2234185123 (Compound 12 in Table 2) as additional Inhibitors of CYP17A1 and/or CYP19A1 for use in the treatment of Prostate Cancer and Breast Cancer:

| # | Compound ID | IUPAC Name & Structural Formula |
|---|---|---|
| 12.15 | Z2670000145 | 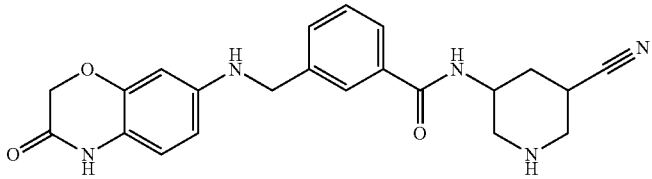 N-(5-cyanopiperidin-3-yl)-3-{[(3-oxo-3)4-dihydro-2H-1,4-benzoxazin-7-yl)amino]methyl}benzamide |
| 12.16 | Z2670000147 | 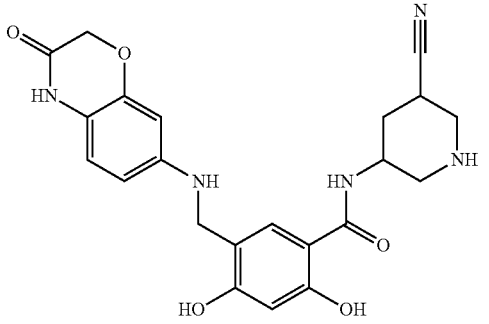 N-(5-cyanopiperidin-3-yl)-2,4-dihydroxy-5-{[(3-oxo-3,4-dihydro-2H-1,4-benzoxazin-7-yl)amino]methyl}benzamide |
| 12.17 | Z2670000133 | 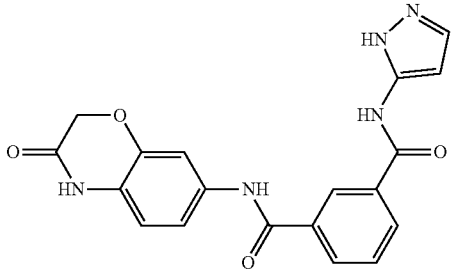 N1-(3-oxo-3,4-dihydro-2H-1,4-benzoxazin-7-yl)-N3-(1H-pyrazol-5-yl)benzene-1,3-dicarboxamide |
| 12.18 | Z2670000134 | 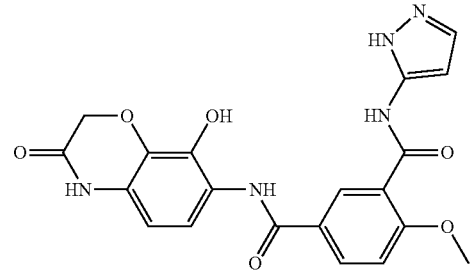 N1-(8-hydroxy-3-oxo-3,4-dihydro-2H-1,4-benzoxazin-7-yl)-4-methoxy-N3-(1H-pyrazol-5-yl)benzene-1,3-dicarboxamide |

TABLE 2A-continued

Derivatives of Compound Z2234185123 (Compound 12 in Table 2) as
additional Inhibitors of CYP17A1 and/or CYP19A1 for use in the treatment of
Prostate Cancer and Breast Cancer:

| # | Compound ID | IUPAC Name & Structural Formula |
|---|---|---|

12.19  Z2670000137

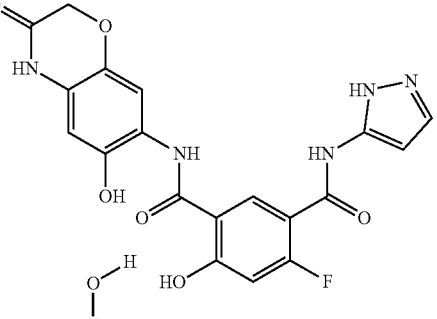

4-fluoro-6-hydroxy-N1-(6-hydroxy-3-oxo-3,4-dihydro-2H-
1,4-benzoxazin-7-yl)-N3-(1H-pyrazol-5-yl)benzene-1,3-
dicarboxamide hydrate 12.20  Z2670000139

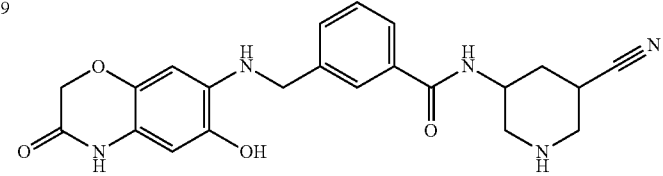

N-(5-cyanopiperidin-3-yl)-3-{[(6-hydroxy-3-oxo-3,4-dihydro-2H-1,4-benzoxazin-7-
yl)amino]methyl}benzamide 12.21  Z2670000151

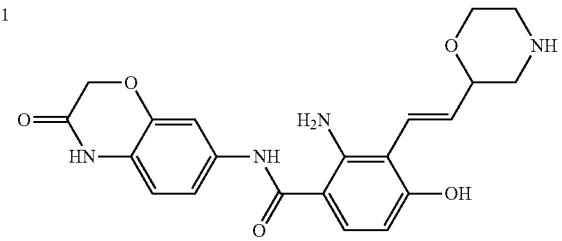

2-amino-4-hydroxy-3-[2-(morpholin-2-yl)ethenyl]-N-(3-oxo-3,4-
dihydro-2H-1,4-benzoxazin-7-yl)benzamide 12.22  Z2670000158

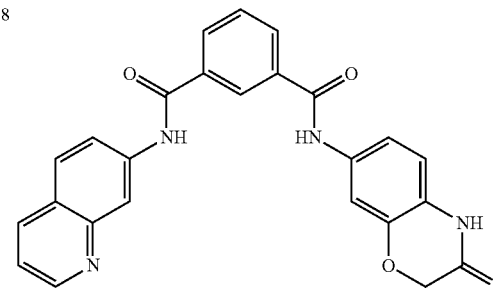

N1-(3-oxo-3,4-dihydro-2H-1,4-benzoxazin-7-yl)-N3-(quinolin-7-
yl)benzene-1,3-dicarboxamide TABLE 2A-continued Derivatives of Compound Z2234185123 (Compound 12 in Table 2) as
additional Inhibitors of CYP17A1 and/or CYP19A1 for use in the treatment of
Prostate Cancer and Breast Cancer:

| # | Compound ID | IUPAC Name & Structural Formula |
|---|---|---|
| 12.23 | Z2670000160 | 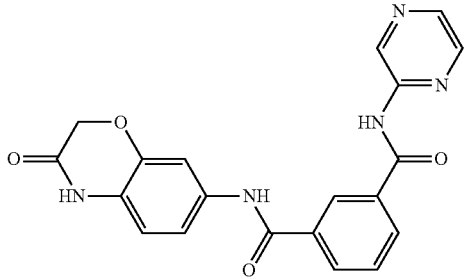 N1-(3-oxo-3,4-dihydro-2H-1,4-benzoxazin-7-yl)-N3-(pyrazin-2-yl)benzene-1,3-dicarboxamide |
| 12.24 | Z2670000163 | 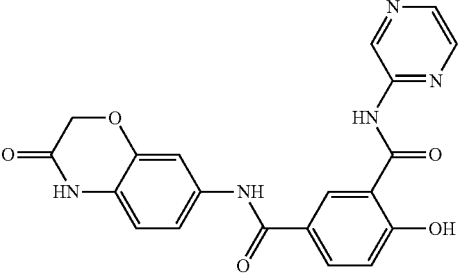 4-hydroxy-N1-(3-oxo-3,4-dihydro-2H-1,4-benzoxazin-7-yl)-N3-(pyrazin-2-yl)benzene-1,3- dicarboxamide |
| 12.25 | Z2670000382 | 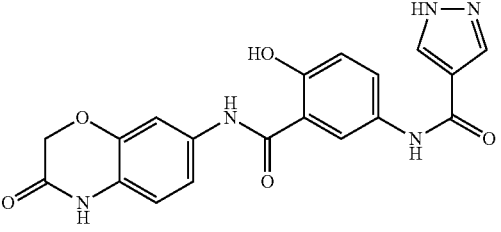 [SMILES: O=C1COc2cc(NC(=O)c3cc(NC(=O)c4cn[nH]c4)ccc3Cl)ccc2N1] N-{4-hydroxy-3-[(3-oxo-3,4-dihydro-2H-1,4-benzoxazin-7-yl)carbamoyl]phenyl}-1H-pyrazole-4-carboxamide |
| 12.26 | Z2670000388 | 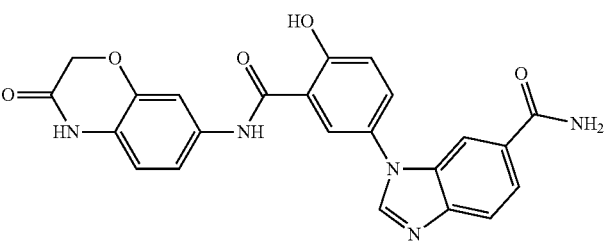 N-{4-hydroxy-3-[(3-oxo-3,4-dihydro-2H-1,4-benzoxazin-7-yl)carbamoyl]phenyl}-1H-1,3-benzodiazole-6-carboxamide |

TABLE 2A-continued

Derivatives of Compound Z2234185123 (Compound 12 in Table 2) as additional Inhibitors of CYP17A1 and/or CYP19A1 for use in the treatment of Prostate Cancer and Breast Cancer:

| # | Compound ID | IUPAC Name & Structural Formula |
|---|---|---|
| 12.27 | Z2670000392 | 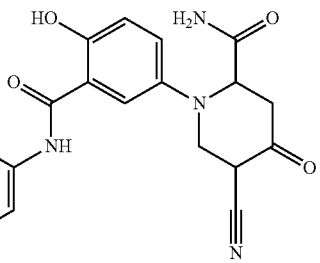 5-cyano-N-{4-hydroxy-3-[(3-oxo-3,4-dihydro-2H-1,4-benzoxazin-7-yl)carbamoyl]phenyl}-4-oxopiperidine-2-carboxamide |
| 12.28 | Z2670000395 | 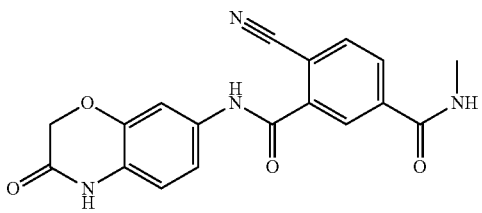 4-cyano-N1-methyl-N3-(3-oxo-3,4-dihydro-2H-1,4-benzoxazin-7-yl)benzene-1,3-dicarboxamide |

TABLE 2B

Further properties of Inhibitors of CYP17A1 and/or CYP19A1 (Compounds from Table 2):

| # | Compound | Formula weight | Monoisotopic weight | Stereochemistry | Soluble in DMSO |
|---|---|---|---|---|---|
| 1 | Z44426883 | 393.41 | 394.1 | | Yes |
| 2 | Z92489215 | 477.967 | 478.1 | | Yes |
| 3 | Z220306370 | 421.531 | 422.0 | Racemic mixture | Yes |
| 4 | Z225980484 | 350.389 | 351.0 | | Yes |
| 5 | Z854502162 | 327.382 | 328.2 | | Yes |
| 6 | Z51102986 | 379.415 | 380.2 | Racemic mixture | Yes |
| 7 | Z1567948782 | 442.301 | 442.0 | | Yes |
| 8 | Z2230799627 | 390.398 | 389.1 | | Yes |
| 9 | Z2234084128 | 440.454 | 441.1 | | Yes |
| 10 | Z2234175518 | 374.3926 | 375.1 | | Yes |
| 11 | Z2234175520 | 389.404 | 390.1 | | Yes |
| 12 | Z2234185123 | 411.7986 | 411.9 | | Yes |
| 13 | Z518027752 (previously named 980171513) | 408.8377 | 409.2 | | Yes |

From a consideration of Tables 2 & 2A above, it will be seen that a further aspect of the invention provides compounds for use as medicaments, each said compound having the formula:

[Chem. 1]

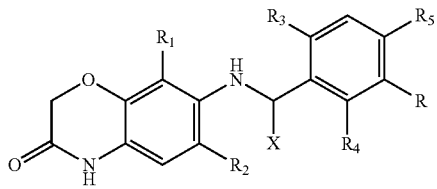

wherein:

R is independently selected from the group consisting of optionally substituted arylamide; optionally substituted alkylarylamide; optionally substituted aryl carboxamide; optionally substituted cyanopiperidine; optionally substituted oxopiperidine; optionally substituted pyridin-3-yl; optionally substituted pyrazole-4-carboxamide; optionally substituted pyrimidin-4-ylcarboxamide; optionally substituted pyrimidin-4-ylcarboxamide; optionally substituted 1H-pyrrol-2-ylcarboxamide; optionally substituted morpholin carboxamide; optionally substituted 1H-indazol-3-ylcarboxamide; optionally substituted 5-cyanopiperidin-3-ylcarboxamide; optionally substituted quinolin-7-yl; optionally substituted pyrazin-2-ylcarboxamide; optionally substituted 1H-1,3-benzodiazole-6-carboxamide; optionally substituted 3-oxo-3,4-dihydro-2H-1,4-benzoxazin-7-ylcarboxamide;

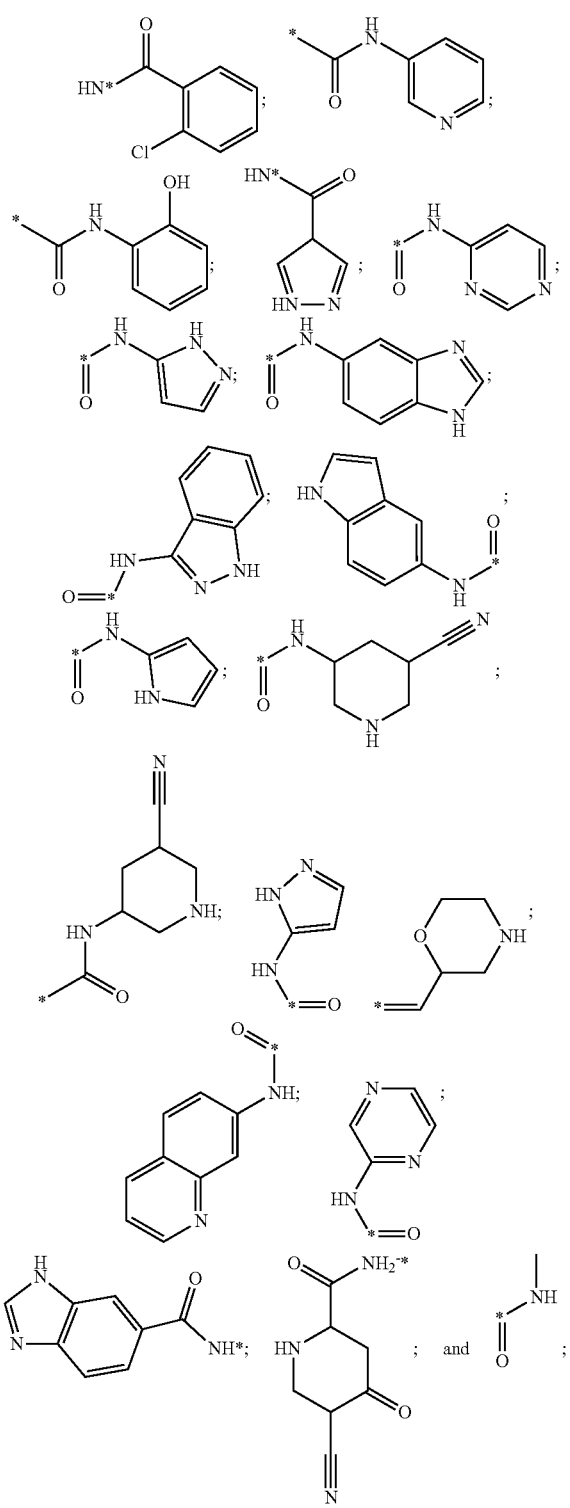

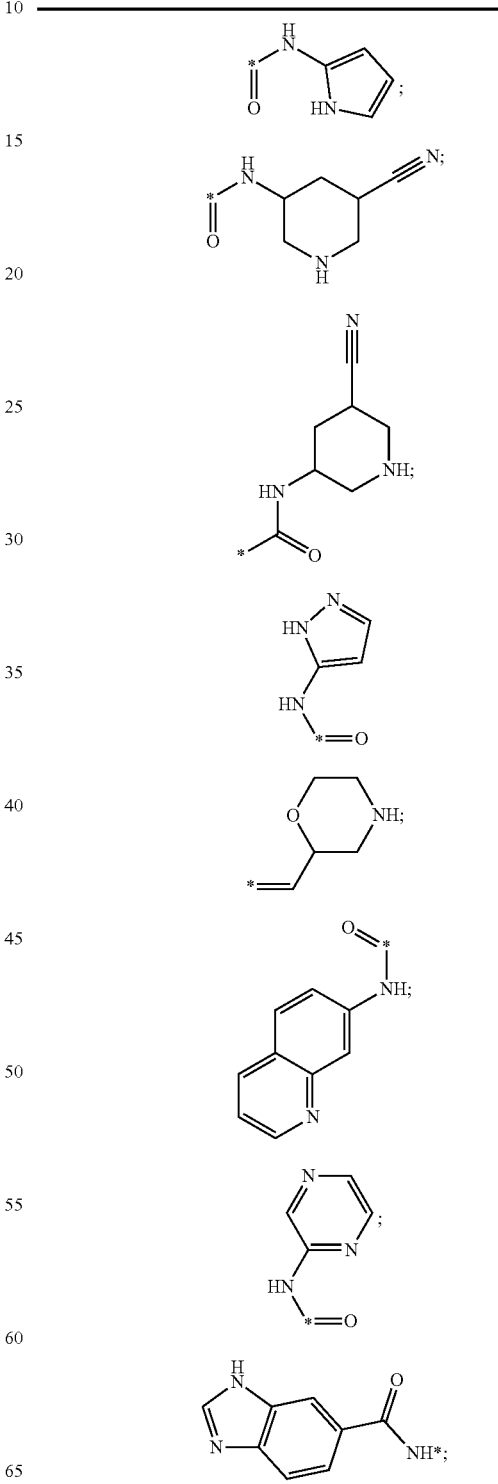

where the point of attachment to Chem. 1 is indicated by an asterisk (*) in each case;

Each R1, R2, R3, R4, R5 is independently selected from the group consisting of H; OH; a halogen atom; OCH$_3$; and NH$_2$; and X is independently selected from the group consisting of H; OH and =O;

and pharmaceutically acceptable enantiomers, diastereomers; tautomers, salts, solvates, hydrates, primary metabolites and prodrugs thereof.

R may be independently selected from the group consisting of:

TABLE R

R Groups for Formula Chem. 1:

TABLE R-continued

R Groups for Formula Chem. 1:

![structures showing a piperidine carboxamide with ketone and cyano substituents, and an NH-C(=O) group with attachment point marked by asterisk]

where the point of attachment to Chem. 1 is indicated by an asterisk (*) in each case.

The compounds for use as medicaments may be selected from those disclosed in Tables 2 & 2A above.

The compounds of Tables 2 & 2A, and/or as defined by the formula Chem. 1, along with their enantiomers, diastereomers, tautomers, salts, solvates, hydrates, primary metabolites and/or prodrugs may be applied for use in the treatment of cancer, especially cancer mediated by CYP17A1 enzyme and/or CYP19A1 enzyme, for example prostate cancer and breast cancer mediated by CYP17A1 enzyme and/or CYP19A1 enzyme.

The invention also provides the use of said compounds, enantiomers, diastereomers, tautomers, salts, solvates, hydrates, primary metabolites and/or prodrugs in the manufacture of a medicament for the treatment of cancer, especially cancer mediated by CYP17A1 enzyme and/or CYP19A1 enzyme, for example prostate cancer and breast cancer mediated by CYP17A1 enzyme and/or CYP19A1 enzyme.

In a further aspect, the invention provides a method for the treatment of cancer mediated by CYP17A1 enzyme and/or CYP19A1 enzyme, comprising a step of administering to a human in need thereof a therapeutically effective amount of a compound disclosed in Tables 2 & 2A, and/or as defined by the formula Chem. 1; or a pharmaceutically acceptable enantiomer, diastereomer, tautomer, salt, solvate, hydrate, primary metabolite or prodrug thereof; or a pharmaceutically acceptable composition containing any of these entities. This method may further comprise a step of testing a human to determine whether said human has cancer mediated by CYP17A1 enzyme and/or CYP19A1 enzyme, prior to said administering step.

In a further aspect of the invention there is provided a method for the treatment of cancer, comprising a step of administering to a patient who has been identified as having cancer a compound disclosed in Tables 2 & 2A, and/or as defined by the formula Chem. 1; or a pharmaceutically acceptable salt, solvate, hydrate, primary metabolite or prodrug thereof; or a pharmaceutically acceptable composition containing any of these entities. This method may further comprise a step of testing patients to identify a patient having cancer.

In yet a further aspect of the invention there is provided a method for the treatment of cancer mediated by CYP17A1 enzyme and/or CYP19A1 enzyme, said method comprising the steps of selecting a patient who has such cancer, and administering to said selected patient a therapeutically effective amount of a compound disclosed in Tables 2 & 2A, and/or as defined by the formula Chem. 1; or a pharmaceutically acceptable enantiomer, diastereomer, tautomer, salt, solvate, hydrate, primary metabolite or prodrug thereof; or a pharmaceutically acceptable composition containing any of these entities. This method may further comprise a step of testing a patient to determine whether the patient has cancer mediated by CYP17A1 enzyme and/or CYP19A1 enzyme.

The cancer may be prostate cancer or breast cancer mediated by CYP17A1 enzyme and/or CYP19A1 enzyme.

According to a further aspect of the invention there is provided a method of inhibiting androgen activity in a subject in need thereof, comprising administering to said subject a therapeutically effective amount of a compound disclosed in Tables 2 & 2A, and/or as defined by the formula Chem. 1; or a pharmaceutically acceptable enantiomer, diastereomer, tautomer, salt, solvate, hydrate, primary metabolite or prodrug thereof; or a pharmaceutically acceptable composition containing either entity.

In yet a further aspect of the invention there is provided a so-called Dual Inhibitor, being a compound for direct inhibition of both the CYP17A1 enzyme and the CYP19A1 enzyme, selected from the group consisting of the following Table 2 compounds: [Compound 7; Z1567948782]; [Compound 10; Z2234175518]; [Compound 12; Z2234185123]; [Compound 13; Z518027752]; and pharmaceutically acceptable enantiomers, diastereomers, tautomers, salts, solvates, hydrates, primary metabolites and prodrugs thereof.

A further aspect of the invention provides compounds for direct inhibition of CYP17A1 enzyme, said compounds being selected from the group consisting of the following Table 2 compounds: [Compound 1; Z44426883]; [Compound 2; Z92489215]; [Compound 3; Z220306370]; [Compound 6; Z51102986]; [Compound 7; Z1567948782]; [Compound 9; Z2234084128]; [Compound 10; Z2234175518]; [Compound 12; Z2234185123]; [Compound 13; Z518027752]; and pharmaceutically acceptable enantiomers, diastereomers, tautomers, salts, solvates, hydrates, primary metabolites and prodrugs thereof.

A further aspect of the invention provides compounds for direct inhibition of CYP19A1 enzyme, said compounds being selected from the group consisting of the following Table 2 compounds: [Compound 4; Z225980484]; [Compound 5; Z854502162]; [Compound 7; Z1567948782]; [Compound 8; Z2230799627]; [Compound 10; Z2234175518]; [Compound 11; Z2234175520]; [Compound 12; Z2234185123]; [Compound 13; Z518027752]; and pharmaceutically acceptable enantiomers, diastereomers, tautomers, salts, solvates, hydrates, primary metabolites and prodrugs thereof.

As stated, some of the compounds identified using the pharmacophore models are understood to be novel and inventive per se.

Therefore, compounds are provided having the formula:

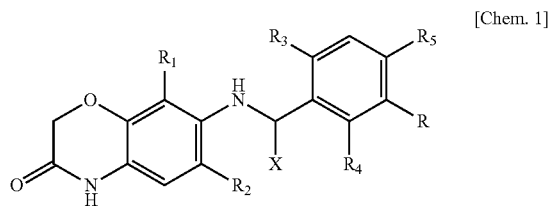

[Chem. 1]

wherein:
R is independently selected from the group consisting of optionally substituted arylamide; optionally substituted alkylarylamide; optionally substituted aryl carboxamide; optionally substituted cyanopiperidine; optionally substituted oxopiperidine; optionally substituted pyridin-3-yl; optionally substituted pyrazole-4-carboxamide; optionally substituted pyrimidin-4-ylcarboxamide; optionally substituted pyrimidin-4-ylcarboxamide; optionally substituted 1H-pyrrol-2-ylcarboxamide; optionally substituted morpholin carboxamide; optionally substituted 1H-indazol-3-ylcarboxamide; optionally substituted 5-cyanopiperidin-3-ylcarboxamide; optionally substituted quinolin-7-yl; optionally substituted pyrazin-2-ylcarboxamide; optionally substituted 1H-1,3-benzodiazole-6-carboxamide; and optionally substituted 3-oxo-3,4-dihydro-2H-1,4-benzoxazin-7-ylcarboxamide;

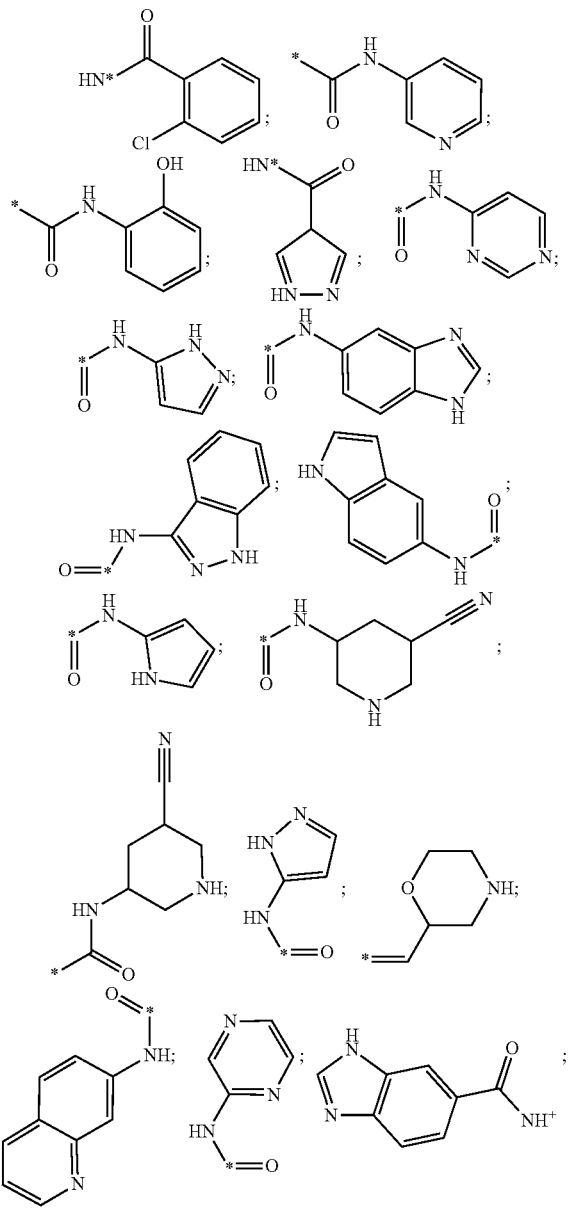
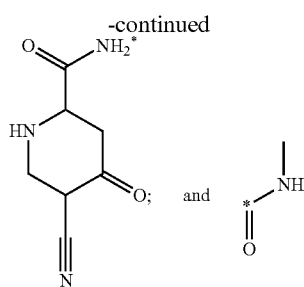

where the point of attachment to Chem. 1 is indicated by an asterisk (*) in each case;

Each R1, R2, R3, R4, R5 is independently selected from the group consisting of H; OH; a halogen atom; $OCH_3$; and $NH_2$; and X is independently selected from the group consisting of H; OH and =O;

provided that said compound is not selected from the group consisting of:
- 2-chloro-N-(3-{[(6-chloro-3-oxo-3,4-dihydro-2H-1,4-benzoxazin-7-yl)amino]methyl}phenyl)benzamide (Molecular Formula: $C_{22}H_{17}Cl_2N_3O_3$) [Compound 7; Z1567948782; CAS Registry number: 1445723-38-5;
- 7-[[[3-(3-pyridinyl)phenyl]methyl]amino]-2H-1,4-benzoxazin-3(4H)-one [CAS Registry No.: 1797677-20-3]; or
- 2-chloro-N-[3-[[(3,4-dihydro-3-oxo-2H-1,4-benzoxazin-7-yl)amino]methyl]phenyl]benzamide [CAS Registry No.: 1832317-56-2].

Enantiomers, diastereomers, tautomers, salts, solvates, hydrates, primary metabolites and prodrugs of the defined compounds are also encompassed.

The compounds according to this aspect of the invention may be selected from the group consisting of:
(from Table 2): [Compound 8; Z2230799627]; [Compound 10; Z2234175518]; [Compound 11; Z2234175520]; [Compound 12; Z2234185123]; and [Compound 13; Z518027752]; and (from Table 2A): [Compound 12.8; Z2670000119]; [Compound 12.9; Z2670000121]; [Compound 12.10; Z2670000123]; [Compound 12.11; Z2670000126]; [Compound 12.12; Z2670000128]; [Compound 12.13; Z2670000131]; [Compound 12.14; Z2670000141]; [Compound 12.15; Z2670000145]; [Compound 12.16; Z2670000147]; [Compound 12.17; Z2670000133]; [Compound 12.18; Z2670000134]; [Compound 12.19; Z2670000137]; [Compound 12.20; Z2670000139]; [Compound 12.21; Z2670000151]; [Compound 12.22; Z2670000158]; [Compound 12.23; Z2670000160]; [Compound 12.24; Z2670000163]; [Compound 12.25; Z2670000382]; [Compound 12.26; Z2670000388]; [Compound 12.27; Z2670000392]; and [Compound 12.28; Z2670000395].

The invention also provides compounds selected from the group consisting of:
- 2-(4-sulfamoylphenoxy) ethyl 2-amino-3-methylbenzoate (Molecular Formula: $C_{16}H_{18}N_2O_5S$) [Compound 4; Z225980484]; and
- N-(3-{[carbamoyl(phenyl)methyl]amino}phenyl)-2-methoxypropanamide (Molecular Formula: $C_{18}H_{21}N_3O_3$) [Compound 5; Z854502162];

along with the enantiomers, diastereomers, tautomers, salts, solvates, hydrates, primary metabolites and prodrugs thereof.

The compounds and compositions disclosed herein may be formulated for administration to patients as a solid, powder, tablet, capsule, suspension, emulsion, and/or sterile solution. They may also be formulated for introduction via the parenteral route, for example by means of injection, suppository, topical delivery, or inhalation. The methods of treatment disclosed herein may likewise involve similar modes of administration.

In yet a further aspect the invention provides a compound for use as a medicament, whenever said compound has been identified by implementation of a process as described herein for designing, screening and/or identifying inhibitors of an enzyme selected from the group consisting of CYP17A1 and CYP19A1.

BRIEF DESCRIPTION OF DRAWINGS

The patent or application file contains at least one drawing executed in color. Copies of this patent or patent application publication with color drawing(s) will be provided by the Office upon request and payment of the necessary fee.

For a better understanding of the present invention, and to show how the same may be carried into effect, embodiments of the invention will now be described by way of non-limiting example with reference to the accompanying diagrammatic drawings, wherein:

FIG. 1 illustrates, schematically, a preferred pharmacophore hypothesis or model AADDRR.860, showing distances and angles thereof. The AADDRR part of the name refers to the variants and 860 refers to the maximum number of hypotheses, which is unique for highly active molecules in the data set;

FIG. 2 illustrates, schematically, distances for the preferred pharmacophore model (hypothesis AADDRR.860) overlaid onto a preferred reference ligand, i.e. N-{4'-[1-Hydroxy-1-(1H-imidazol-4-yl)-2-methylpropyl][1,1'-biphenyl]-3-yl}acetamide (Compound 7 in Table 4; 17[12] in Table 4A);

FIG. 3 illustrates, schematically, bond angles for the preferred pharmacophore model (hypothesis AADDRR.860) overlaid onto the preferred reference ligand;

FIG. 4 illustrates, schematically, a "clean" representation of the preferred reference ligand mapped onto the pharmacophore hypothesis AADDRR.860, with distances and bond angles removed for clarity;

FIGS. 5.1, 5.2 and 5.3 illustrate, schematically, docking screens and ligand interaction diagrams (LIDs) for potential CYP17A1 inhibitors that were identified (corresponding to selected compounds tabulated in Table 2);

FIGS. 6.1, 6.2 and 6.3 illustrate, schematically, docking screens and ligand interaction diagrams (LIDs) for potential CYP19A1 inhibitors that were identified (corresponding to selected compounds tabulated in Table 2);

FIG. 7 illustrates, schematically, native docking poses for a separate reference ligand TOK-001 (Galeterone), for model validation;

FIG. 8 illustrates, schematically, validation plots of $pIC_{50}$ (estimated vs. experimental) for pharmacophore hypothesis AADDRR.860. The QSAR model corresponds to a 3 latent variables-PLS model. The left hand plot is for a training set ($R^2$ 0.9228) and the right hand plot is for a test set ($Q^2$ 0.9400);

FIG. 9.1 shows an LC-MS/MS spectrum for the parent and the corresponding fragments of Compounds 1 to 6; and FIG. 9.2 shows an LC-MS/MS spectrum for the parent and corresponding fragments of Compounds 7 to 12.

DETAILED DESCRIPTION

Compounds identified according to the present invention inhibit the activity of the CYP17A1 and CYP19A1 enzymes in the following pathways for steroidogenesis of androgens and estrogens:

CYP17A1

Inhibitors of CYP17A1 block 17α-hydroxylase activity i.e. the hydroxylation of progesterone to form 17α-hydroxy-progesterone:

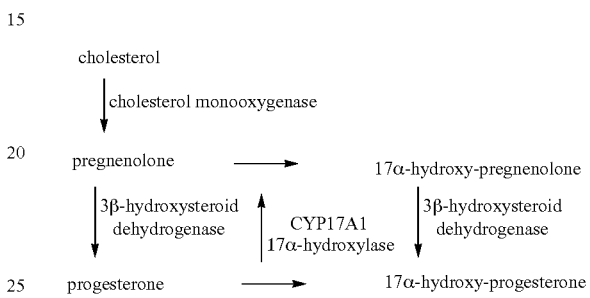

CYP19A1

Inhibitors of CYP19A1 block the aromatization of androstenedione and testosterone to form estrone and estradiol, respectively:

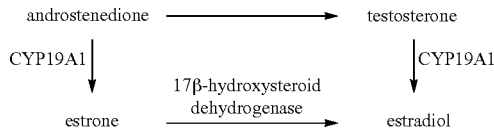

Qualitative 3D pharmacophore hypotheses or models were developed using 3D-QSAR techniques.

Chemical structures of known CYP17A1 inhibitors with varying degrees of inhibition were used to generate pharmacophore models. Preferred pharmacophore models were then used to perform chemometric analysis using partial least squares regression (PLS).

Pharmacophore model AADDRR.860 (FIGS. 1 to 3 of the accompanying drawings) was selected as a most preferred fit to the known compounds. It was then used to search for similarity in terms of pharmacophore features of new chemical entities (NCEs) and to virtually screen a database of candidate compounds to be used for CYP17A1 and CYP19A1 inhibition.

Flexible docking techniques were used to mine suitable candidate compounds. Docking is frequently used to predict the binding orientation of small molecular drug candidates to their protein targets in order to predict the affinity and activity of the small molecule.

The various inhibitory potencies to their target enzymes and various CYP450 isoforms responsible for the metabolism of known drugs are shown in Table 2 above.

Equipment & Software Used

The following equipment and software were used in the development of this invention:

Maestro (v10.2), a graphical user interface (GUI) in Schrödinger Suite 2015, was used to perform all simulation tasks. The GUI has built-in workflows for all Schrödinger modules in the suite. (See citation NPL8 for the Maestro panel).

Conformational searches were performed by using MacroModel (v10.8). (See citation NPL9.)

Pharmacophore modelling was performed by using PHASE (v4.3), a module of the Schrödinger 2015 product suite. (See citations NPL10 and NPL11.)

Quantum Mechanical/Molecular Mechanics (QM/MM) calculations were performed by using Jaguar (v8.8). (See citation NPL12.)

Induced Fit Docking (IFD) Protocol 2015-2 was used for all flexible molecular docking calculations of database hits that survived the virtual screening protocol. (See citations NPL13 to NPL15.)

Process in Detail 1.1 Development of Pharmacophore Hypotheses

The design of a pharmacophore hypothesis was performed by using a training and test dataset of known and previously synthesized steroidal and non-steroidal organic compounds that have shown varying degrees of inhibition to the CYP17A1 enzyme. The compounds of the dataset were collected from the literature and included 17-indazole androstene derivatives, isopropylene substituted to biphenylmethylene 4-pyridine, steroidal imidazoyl, triazoyl substituted biphenyl, biphenyl methylene, methylene imidazole substituted biaryls, naphthyl methyl imidazole derivatives, biphenyl-yl-methyl imidazole derivatives and abiraterone analogues.

Also included in the initial dataset were FDA approved inhibitors of CYP17A1 such as Ketoconazole, Abiraterone as well as Phase II and Phase III drug candidates such as Orteronel and Galeterone with known $IC_{50}$ inhibition to CYP17A1.

The initial dataset comprised of 105 molecules with diverse core structures and broad inhibition activity to the CYP17A1 enzyme (in vitro experimental $IC_{50}$ scores from 13 to 20000 nM). Tables 4 and 4A tabulate a selection of molecules from the initial training and test dataset.

In vitro experimental $IC_{50}$ values, in molar (M) units, were converted into $pIC_{50}$ (i.e. $-\log IC_{50}$) data. The $IC_{50}$ values were obtained from the literature. A $pIC_{50}$ threshold was set for the selection of active and inactive ligands. Ligands with a $pIC_{50}<7.01$ ($IC_{50}$ 97 nM) were considered as inactives (i.e. weak binders) while moderately active values ($7.54<pIC_{50}<7.01$) were considered as medium inhibitors. Lastly, inhibitors with a $pIC_{50}>7.54$ ($IC_{50}$ 29 nM) were considered as most active ligands (i.e. strong binders). This activity threshold was set in the software module used for the investigations, so that sampling of the pharmacophore features of functional groups was restricted to those of highly active molecules in the data set only.

1.1 Ligand Preparation

The structures in the dataset were added in Phase as 2D and were converted into 3D in the ligprep panel. Tautomers were generated for low-energy structures at pH 7.4 and all combinations of stereoisomers in the dataset were generated using ligprep. The adjusted 3D structures were then subjected to a conformational search using MacroModel (v9.9) and a ConfGen instead of Mixed Monte Carlo Multiple Minimum Low Mode (MCMM/LMOD) conformational search method.

OPLS-2005 force-field with a distant-depended dielectric constant was used to generate low-energy multiple conformers with a constant dielectric constant of 1.0. The number of minimization steps was set to 100. A maximum relative energy difference of 10 Kcal/mol was set for saving multiple conformers. A Root-Mean-Square-Deviation (RMSD) cut-off of 1.0 Å was set to eliminate redundant conformers.

1.2 Create Sites Step

In the create sites step, the resulting conformers of stereoisomers were mapped against a set of chemical structural patterns to identify pharmacophore features in each ligand. Once a feature has been mapped onto a specific location in a conformation, it is referred to as a pharmacophore site. These pharmacophore features include hydrogen bond acceptors (A), hydrogen bond donors (D), negatively charged groups (N), positively charged groups (P), hydrophobic groups (H) and aromatic rings (R) as built in features. A user has a choice to add other features characteristic of the dataset. We opted to use the default features in order to account for structural features present in our dataset (i.e. types of functional groups exhibited by most active structures).

1.3 Find Common Pharmacophore Step

In this step we performed a search for common pharmacophores among the set of high-affinity (active) ligands that were chosen in the first step. The search spanned one or more families of pharmacophores, known as variants (resulting from the pharmacophore sites created in the previous step for all structures in the data set). The number of site points was chosen to be 6 and at least 4 of the active groups of the most active structures in the dataset were required to be matched. A filtering-out of variants that had too many or too few of a particular kind of feature was performed, and a set of variants was selected from the filtered list. A choice can be made in which a user decreases the number of ligands that must match a pharmacophore before it can be considered to be a hypothesis. The search proceeds by enumerating all pharmacophores of a given variant and partitioning them into successively smaller high-dimensional boxes according to their intersite distances. Each n-point pharmacophore contains $n(n-1)/2$ unique intersite distances, so each box contains $n(n-1)/2$ dimensions. Pharmacophores that are clustered into the same box are considered to be equivalent and therefore common to the ligands from which they arise. The size of the box defines the tolerance on each intersite distance, and therefore how similar common pharmacophores must be. Initially, the available parameters for pharmacophore features were as follows A=2, D=2, H=3, and R=3. Then we opted to decrease the hydrophobic features (H) from 3 to 2, resulting in the following frequency of features: A=2, D=2, H=2 and R=3. The variant list decreased from 34 to 17 with each box containing pharmacophores from the minimum required number of ligands which are said to survive the partitioning process. Each surviving box contains a set of common pharmacophores, one of which is ultimately singled out as a hypothesis. This is the crucial stage of pharmacophore hypothesis development because the resulting hypothesis depends on the choices made here on the number of point sites to be considered as more reactive and common in the data set. Non-model ligands were aligned in this step.

1.4 Score Hypotheses Step

In this step we applied a scoring function that identified the best candidate hypothesis from each surviving box and provided an overall ranking of all the hypotheses. The scoring algorithm includes contributions from the alignment of site points and vectors, volume overlap, selectivity, number of ligands matched, relative conformational energy, and activity. The choice of the best hypothesis was made based on the relative conformational energy of the conformer that fit the hypothesis snugly with a highest fitness score of 3. This conformer is referred to as a reference ligand in the data set. For present purposes this was established as N-{4'-[1-Hydroxy-1-(1H-imidazol-4-yl)-2-methylpropyl][1,1'-biphenyl]-3-yl}acetamide (Compound 7 in Table 4; 17[12] in Table 4A), with a relative conformational energy of 0.00 kcal/mol. The conformer with the lowest relative potential energy has fewer steric clashes and would potentially induce conformational changes when bound to flexible enzymes or receptors. There were other hypotheses that exhibited similar results but we focused on this hypothesis because it had good correlation coefficients for training and test sets in the 3D-QSAR model step.

1.5 Build QSAR Model Step

In this step we built QSAR models for the selected hypotheses using the activity data for molecules that matched at least three points in the hypothesis. It is possible to use molecules with varying levels of activity, including those which may be inactive due to steric clashes with the target receptor. The QSAR model partitions space into a grid of uniformly sized cubes, and characterizes each molecule by a set of binary-valued independent variables that encode the occupancy of these cubes by six atom classes or a set of pharmacophore feature types. Partial least squares (PLS) regression was applied to these variables to build a series of models with successively greater numbers of factors. It is possible to view a QSAR model in the Workspace, and to analyse it by atom or feature class and ligand. This can be used to identify ligand features that contribute positively or negatively to the predicted activity.

We did not separate the dataset randomly as training and test sets, respectively, at first. We opted to build the QSAR model with all molecules as training sets. The 'Atom-based pharmacophore model' option in PHASE was preferred over pharmacophore-based alignment, since it has been described as adequate for structures that contain a small number of rotatable bonds with a common structural framework. The number of PLS factors was set to 3 to prevent overfitting of the QSAR model. The results gave predicted activities for all ligands in the data set which were correlated with experimental activities. We manually removed six molecules in the data set with predicted $pIC_{50}$ values that did not correspond with experimental $pIC_{50}$ values. These outliers are due largely to heterogeneous response variables from in vitro experiments, since available experimental activities were measured with different assay methods from the rest of the molecules in the dataset. We then randomly selected 85 structures as part of the training set and 15 structures in the test set.

The result was 204 models with a combination of good and bad $R^2$ and $Q^2$ statistical results. The best 3D-QSAR pharmacophore model was AADDRR.860 with $R^2=0.9228$ and $Q^2=0.940$ after another outlier removal of 22 structures using leave-n-out-cross validation method.

FIG. 8 of the accompanying drawings shows validation plots of $pIC_{50}$ (estimated vs. experimental) for pharmacophore hypothesis AADDRR.860. The QSAR model corresponds to a 3 latent variables-PLS model. The left had plot is for the training set ($R^2$ 0.9228) and the right hand plot is for the test set ($Q^2$ 0.8953).

The following Table 3 tabulates the various 3D-QSAR pharmacophore hypotheses which were identified, and sets out their statistical data:

TABLE 3

Statistical Data for Shortlisted 3D-QSAR Pharmacophore Models:

| No. | Hypothesis ID | # PLS Factors | SD | R-squared | F | P | Stability | RMSE | Q. squared | Pearson-R |
|---|---|---|---|---|---|---|---|---|---|---|
| 1 | AHHRRR.100 | 1 | 0.5724 | 0.4155 | 61.1 | 1.224e−011 | 0.8997 | 0.5093 | 0.6634 | 0.9043 |
|   |   | 2 | 0.4080 | 0.7064 | 102.3 | 2.395e−023 | 0.6915 | 0.3870 | 0.8057 | 0.9391 |
|   |   | 3 | 0.3496 | 0.7870 | 103.5 | 4.032e−028 | 0.6147 | 0.4511 | 0.7359 | 0.8741 |
| 2 | AHHRRR.99 | 1 | 0.5724 | 0.4155 | 61.1 | 1.224e−011 | 0.8997 | 0.5093 | 0.6634 | 0.9043 |
|   |   | 2 | 0.4080 | 0.7064 | 102.3 | 2.395e−023 | 0.6915 | 0.3870 | 0.8057 | 0.9391 |
|   |   | 3 | 0.3496 | 0.7870 | 103.5 | 4.032e−028 | 0.6147 | 0.4511 | 0.7359 | 0.8741 |
| 3 | AADRRR.325 | 1 | 0.5208 | 0.5487 | 91.2 | 1.353e−014 | 0.9356 | 0.5366 | 0.6264 | 0.8224 |
|   |   | 2 | 0.3542 | 0.7940 | 142.6 | 4.076e−026 | 0.6998 | 0.4723 | 0.7105 | 0.8598 |
|   |   | 3 | 0.2788 | 0.8741 | 168.9 | 9.138e−033 | 0.5757 | 0.4370 | 0.7522 | 0.9057 |
| 4 | AADRRR.178 | 1 | 0.5490 | 0.4979 | 75.4 | 5.465e−013 | 0.9272 | 0.5940 | 0.5422 | 0.7731 |
|   |   | 2 | 0.3955 | 0.7428 | 108.3 | 7.661e−023 | 0.7961 | 0.5450 | 0.6145 | 0.8616 |
|   |   | 3 | 0.2847 | 0.8685 | 162.9 | 1.637e−032 | 0.6995 | 0.4207 | 0.7704 | 0.9347 |
| 5 | ADDRRR.1374 | 1 | 0.5656 | 0.4670 | 66.6 | 5.423e−012 | 0.9141 | 0.5893 | 0.5494 | 0.7912 |
|   |   | 2 | 0.3828 | 0.7590 | 118.1 | 6.681e−024 | 0.7643 | 0.5421 | 0.6187 | 0.8329 |
|   |   | 3 | 0.2886 | 0.8649 | 157.9 | 4.415e−032 | 0.7136 | 0.3882 | 0.8045 | 0.9464 |
| 6 | AADRRR.176 | 1 | 0.5311 | 0.5307 | 84.8 | 5.963e−014 | 0.9436 | 0.5650 | 0.5858 | 0.7872 |
|   |   | 2 | 0.3887 | 0.7520 | 112.2 | 3.943e−023 | 0.8355 | 0.5082 | 0.6649 | 0.8569 |
|   |   | 3 | 0.2702 | 0.8817 | 181.4 | 9.392e−034 | 0.6911 | 0.4585 | 0.7272 | 0.8849 |
| 7 | AADRRR.182 | 1 | 0.5379 | 0.5147 | 81.7 | 1.016e−013 | 0.9359 | 0.5661 | 0.5842 | 0.7808 |
|   |   | 2 | 0.3791 | 0.7621 | 121.7 | 2.014e−024 | 0.7723 | 0.5503 | 0.6071 | 0.8063 |
|   |   | 3 | 0.2759 | 0.8756 | 176.0 | 7.372e−034 | 0.6443 | 0.4054 | 0.7867 | 0.9032 |
| 8 | ADDRRR.954 | 1 | 0.5318 | 0.5295 | 84.4 | 6.573e−014 | 0.9358 | 0.6053 | 0.5245 | 0.7862 |
|   |   | 2 | 0.3896 | 0.7508 | 111.5 | 4.722e−023 | 0.8547 | 0.5501 | 0.6073 | 0.8478 |
|   |   | 3 | 0.2636 | 0.8874 | 191.8 | 1.545e−034 | 0.7472 | 0.4348 | 0.7547 | 0.8777 |
| 9 | AADDRR.301 | 1 | 0.4465 | 0.6322 | 104.9 | 7.136e−015 | 0.8981 | 0.5100 | 0.6624 | 0.8427 |
|   |   | 2 | 0.3108 | 0.8247 | 141.1 | 2.057e−023 | 0.6586 | 0.4917 | 0.6863 | 0.8495 |
|   |   | 3 | 0.2332 | 0.9029 | 182.9 | 7.775e−030 | 0.5206 | 0.4062 | 0.7859 | 0.9127 |
| 10 | AADRRR.170 | 1 | 0.5313 | 0.5303 | 84.7 | 6.153e−014 | 0.9448 | 0.5546 | 0.6009 | 0.8051 |
|   |   | 2 | 0.3994 | 0.7381 | 104.3 | 2.952e−022 | 0.8279 | 0.4719 | 0.7111 | 0.8773 |
|   |   | 3 | 0.3114 | 0.8429 | 130.6 | 2.89e−029 | 0.7095 | 0.4624 | 0.7225 | 0.8967 |
| 11 | ADDRRR.523 | 1 | 0.5362 | 0.5209 | 82.6 | 8.957e−014 | 0.8845 | 0.5154 | 0.6553 | 0.8409 |
|   |   | 2 | 0.4122 | 0.7207 | 96.7 | 1.696e−021 | 0.7766 | 0.4942 | 0.6830 | 0.8439 |
|   |   | 3 | 0.2595 | 0.8907 | 201.1 | 1.742e−035 | 0.5909 | 0.4469 | 0.7408 | 0.8663 |
| 12 | AADDRR.860 | 1 | 0.4551 | 0.6178 | 98.6 | 2.328e−014 | 0.9263 | 0.4356 | 0.7538 | 0.9104 |
|   |   | 2 | 0.2955 | 0.8415 | 159.3 | 1.002e−024 | 0.6890 | 0.4034 | 0.7888 | 0.9189 |
|   |   | 3 | 0.2080 | 0.9228 | 234.9 | 9.29e−033 | 0.6389 | 0.2841 | 0.9400 | 0.9720 |

TABLE 3-continued

Statistical Data for Shortlisted 3D-QSAR Pharmacophore Models:

| No. | Hypothesis ID | # PLS Factors | SD | R-squared | F | P | Stability | RMSE | Q. squared | Pearson-R |
|---|---|---|---|---|---|---|---|---|---|---|
| 13 | ADDRRR.1370 | 1 | 0.5447 | 0.5063 | 76.9 | 4.067e−013 | 0.9353 | 0.5972 | 0.5373 | 0.7616 |
| | | 2 | 0.3931 | 0.7463 | 108.8 | 9.099e−023 | 0.7721 | 0.5856 | 0.5550 | 0.7775 |
| | | 3 | 0.2935 | 0.8605 | 150.1 | 3.805e−031 | 0.6117 | 0.4746 | 0.7077 | 0.8689 |
| 14 | AADDRR.1934 | 1 | 0.5768 | 0.3852 | 42.0 | 1.282e−008 | 0.9724 | 0.7847 | 0.2479 | 0.5389 |
| | | 2 | 0.3868 | 0.7277 | 88.2 | 2.287e−019 | 0.8114 | 0.5937 | 0.5695 | 0.8545 |
| | | 3 | 0.2683 | 0.8709 | 146.2 | 7.769e−029 | 0.6228 | 0.4255 | 0.7789 | 0.8884 |
| 15 | AADDRR.1902 | 1 | 0.5807 | 0.4381 | 59.3 | 4.154e−011 | 0.9537 | 0.6298 | 0.4853 | 0.7254 |
| | | 2 | 0.3718 | 0.7727 | 127.5 | 7.487e−025 | 0.6791 | 0.4571 | 0.7288 | 0.9427 |
| | | 3 | 0.2823 | 0.8707 | 166.2 | 8.627e−033 | 0.6387 | 0.4095 | 0.7824 | 0.9185 |
| 16 | AADDRR.1592 | 1 | 0.4843 | 0.5673 | 80.0 | 1.073e−012 | 0.9108 | 0.5682 | 0.5810 | 0.7778 |
| | | 2 | 0.3789 | 0.7395 | 85.2 | 2.975e−018 | 0.7124 | 0.5764 | 0.5688 | 0.7595 |
| | | 3 | 0.2750 | 0.8650 | 126.1 | 1.269e−025 | 0.4487 | 0.4339 | 0.7557 | 0.8753 |
| 17 | AADDRR.1564 | 1 | 0.4267 | 0.6640 | 120.5 | 4.43e−016 | 0.9143 | 0.4077 | 0.7844 | 0.9160 |
| | | 2 | 0.3103 | 0.8252 | 141.7 | 1.88e−023 | 0.7392 | 0.4196 | 0.7715 | 0.8956 |
| | | 3 | 0.1935 | 0.9332 | 274.7 | 1.297e−034 | 0.5070 | 0.3927 | 0.7999 | 0.9066 |
| 18 | ADDRRR.669 | 1 | 0.5118 | 0.5642 | 97.1 | 3.601e−015 | 0.9336 | 0.5477 | 0.6108 | 0.8263 |
| | | 2 | 0.3623 | 0.7844 | 134.6 | 2.196e−025 | 0.7945 | 0.5883 | 0.5509 | 0.7653 |
| | | 3 | 0.2956 | 0.8584 | 147.6 | 6.538e−031 | 0.7349 | 0.4717 | 0.7112 | 0.8546 |
| 19 | AADDRR.1568 | 1 | 0.4189 | 0.6744 | 128.4 | 9.575e−017 | 0.8471 | 0.4562 | 0.7300 | 0.8616 |
| | | 2 | 0.3257 | 0.8063 | 126.9 | 1.815e−022 | 0.7562 | 0.5376 | 0.6250 | 0.7938 |
| | | 3 | 0.2267 | 0.9077 | 196.8 | 5.316e−031 | 0.5740 | 0.4644 | 0.7202 | 0.8552 |
| 20 | AADDRR.808 | 1 | 0.4213 | 0.6706 | 126.2 | 1.367e−016 | 0.838 | 0.4890 | 0.6897 | 0.8522 |
| | | 2 | 0.2445 | 0.8909 | 249.0 | 4.542e−030 | 0.5377 | 0.4454 | 0.7426 | 0.8713 |
| | | 3 | 0.1848 | 0.9387 | 306.1 | 2.6e−036 | 0.4016 | 0.4430 | 0.7453 | 0.8783 |
| 21 | AADDRR.1907 | 1 | 0.5747 | 0.4461 | 62.0 | 1.771e−011 | 0.9712 | 0.5419 | 0.6189 | 0.8213 |
| | | 2 | 0.4187 | 0.7099 | 93.0 | 3.796e−021 | 0.7983 | 0.4806 | 0.7003 | 0.8672 |
| | | 3 | 0.2467 | 0.9006 | 226.4 | 1.699e−037 | 0.5036 | 0.3399 | 0.8501 | 0.9522 |
| 22 | AADHHR.20 | 1 | 0.5003 | 0.5261 | 75.5 | 1.239e−012 | 0.9102 | 0.4229 | 0.7984 | 0.9394 |
| | | 2 | 0.3560 | 0.7635 | 108.2 | 1.051e−021 | 0.7513 | 0.4642 | 0.7571 | 0.9204 |
| | | 3 | 0.2805 | 0.8555 | 130.2 | 1.159e−027 | 0.6428 | 0.5073 | 0.7099 | 0.8963 |
| 23 | AADHHR.64 | 1 | 0.5003 | 0.5261 | 75.5 | 1.239e−012 | 0.9102 | 0.4229 | 0.7984 | 0.9394 |
| | | 2 | 0.3560 | 0.7635 | 108.2 | 1.051e−021 | 0.7513 | 0.4642 | 0.7571 | 0.9204 |
| | | 3 | 0.2805 | 0.8555 | 130.2 | 1.159e−027 | 0.6428 | 0.5073 | 0.7099 | 0.8963 |
| 24 | AADHHR.28 | 1 | 0.5003 | 0.5261 | 75.5 | 1.239e−012 | 0.9102 | 0.4229 | 0.7984 | 0.9394 |
| | | 2 | 0.3560 | 0.7635 | 108.2 | 1.051e−021 | 0.7513 | 0.4642 | 0.7571 | 0.9204 |
| | | 3 | 0.2805 | 0.8555 | 130.2 | 1.159e−027 | 0.6428 | 0.5073 | 0.7099 | 0.8963 |
| 25 | AADRRR.174 | 1 | 0.5130 | 0.5621 | 96.3 | 4.319e−015 | 0.9298 | 0.5448 | 0.6149 | 0.8272 |
| | | 2 | 0.3928 | 0.7466 | 109.4 | 8.694e−023 | 0.8054 | 0.5164 | 0.6540 | 0.9083 |
| | | 3 | 0.2827 | 0.8706 | 163.7 | 2.484e−032 | 0.6194 | 0.4091 | 0.7828 | 0.9728 |
| 26 | ADDHHR.281 | 1 | 0.4572 | 0.5711 | 95.9 | 7.142e−015 | 0.8800 | 0.6092 | 0.5817 | 0.8665 |
| | | 2 | 0.3160 | 0.7979 | 140.2 | 2.218e−025 | 0.6127 | 0.5464 | 0.6636 | 0.9261 |
| | | 3 | 0.2418 | 0.8834 | 176.7 | 1.384e−032 | 0.4834 | 0.4609 | 0.7605 | 0.9587 |
| 27 | ADDRRR.674 | 1 | 0.4805 | 0.6158 | 120.2 | 3.057e−017 | 0.9226 | 0.5464 | 0.6126 | 0.8047 |
| | | 2 | 0.3365 | 0.8142 | 162.1 | 9.099e−028 | 0.8085 | 0.5593 | 0.5941 | 0.8111 |
| | | 3 | 0.2896 | 0.8641 | 154.7 | 1.47e−031 | 0.7888 | 0.4695 | 0.7140 | 0.9053 |
| 28 | ADDHRR.250 | 1 | 0.5436 | 0.4975 | 77.2 | 2.79e−013 | 0.9304 | 0.5480 | 0.6103 | 0.833 |
| | | 2 | 0.3859 | 0.7501 | 115.6 | 6.532e−024 | 0.7474 | 0.4423 | 0.7461 | 0.9268 |
| | | 3 | 0.3242 | 0.8259 | 120.2 | 9.101e−029 | 0.6869 | 0.4423 | 0.7461 | 0.9094 |
| 29 | ADHRRR.637 | 1 | 0.4966 | 0.5728 | 108.6 | 1.271e−016 | 0.8886 | 0.5720 | 0.6032 | 0.8562 |
| | | 2 | 0.3813 | 0.7512 | 120.8 | 6.817e−025 | 0.7584 | 0.4740 | 0.7275 | 0.9253 |
| | | 3 | 0.3233 | 0.8233 | 122.7 | 1.191e−029 | 0.6439 | 0.4206 | 0.7854 | 0.9292 |
| 30 | ADHHRR.643 | 1 | 0.4966 | 0.5728 | 108.6 | 1.271e−016 | 0.8886 | 0.5720 | 0.6032 | 0.8562 |
| | | 2 | 0.3813 | 0.7512 | 120.8 | 6.817e−025 | 0.7584 | 0.4740 | 0.7275 | 0.9253 |
| | | 3 | 0.3233 | 0.8233 | 122.7 | 1.191e−029 | 0.6439 | 0.4206 | 0.7854 | 0.9292 |
| 31 | AADHHR.46 | 1 | 0.5354 | 0.4594 | 56.9 | 1.584e−010 | 0.8086 | 0.4743 | 0.7465 | 0.9562 |
| | | 2 | 0.4001 | 0.7027 | 78.0 | 4.145e−018 | 0.5554 | 0.4134 | 0.8074 | 0.9421 |
| | | 3 | 0.2634 | 0.8731 | 149.1 | 4.452e−029 | 0.2224 | 0.5038 | 0.7139 | 0.8605 |
| 32 | AADHHR.45 | 1 | 0.5354 | 0.4594 | 56.9 | 1.584e−010 | 0.8086 | 0.4743 | 0.7465 | 0.9562 |
| | | 2 | 0.4001 | 0.7027 | 78.0 | 4.145e−018 | 0.5554 | 0.4134 | 0.8074 | 0.9421 |
| | | 3 | 0.2634 | 0.8731 | 149.1 | 4.452e−029 | 0.2224 | 0.5038 | 0.7139 | 0.8605 |
| 33 | AADHHR.1 | 1 | 0.5354 | 0.4594 | 56.9 | 1.584e−010 | 0.8086 | 0.4743 | 0.7465 | 0.9562 |
| | | 2 | 0.4001 | 0.7027 | 78.0 | 4.145e−018 | 0.5554 | 0.4134 | 0.8074 | 0.9421 |
| | | 3 | 0.2634 | 0.8731 | 149.1 | 4.452e−029 | 0.2224 | 0.5038 | 0.7139 | 0.8605 |
| 34 | AADHHR.2 | 1 | 0.5354 | 0.4594 | 56.9 | 1.584e−010 | 0.8086 | 0.4743 | 0.7465 | 0.9562 |
| | | 2 | 0.4001 | 0.7027 | 78.0 | 4.145e−018 | 0.5554 | 0.4134 | 0.8074 | 0.9421 |
| | | 3 | 0.2634 | 0.8731 | 149.1 | 4.452e−029 | 0.2224 | 0.5038 | 0.7139 | 0.8605 |
| 35 | AADDHR.533 | 1 | 0.4846 | 0.5534 | 89.2 | 3.097e−014 | 0.8162 | 0.6214 | 0.4989 | 0.8316 |
| | | 2 | 0.2936 | 0.8384 | 184.2 | 7.968e−029 | 0.5684 | 0.5626 | 0.5893 | 0.8074 |
| | | 3 | 0.2183 | 0.9119 | 241.6 | 7.577e−037 | 0.5202 | 0.4792 | 0.7021 | 0.8676 |
| 36 | ADHRRR.79 | 1 | 0.5006 | 0.5745 | 105.3 | 3.958e−016 | 0.9350 | 0.5631 | 0.5885 | 0.8499 |
| | | 2 | 0.3749 | 0.7645 | 125.0 | 6.642e−025 | 0.8668 | 0.5608 | 0.5919 | 0.9119 |
| | | 3 | 0.3030 | 0.8482 | 141.5 | 5.069e−031 | 0.7856 | 0.4587 | 0.7269 | 0.9415 |

Compounds from the training and test sets, as used for the generation of the pharmacophores, are listed in Tables 4 & 4A below. Table 4A also provides actual and predicted activities of a subset of the training and test set, as applied to the preferred pharmacophore model AADDRR.860.

TABLE 4

IUPAC Systematic Names for known CYP 17A1 inhibitors used to generate Pharmacophore Models:

| ID | Code [Ref] | Systematic Name |
|---|---|---|
| 1 | 3d (Kaku, 2011a) | 6-(6,7-Dihydro-5H-pyrrolo[1,2-c]imidazol-7-yl)-N-methyl-2-naphthamide |
| 2 | 1 (Handratta,2005) | 6-[1-Hydroxy-1-isopropyl(1H-imidazol-5-yl)methyl]-Nmethylnaphthalene-2-carboxamide |
| 3 | 5 (Budha, 2008) | 1-[1,1'-biphenyl]-3-yl-1-(1H-imidazol-4-yl)-2-methyl-1-propanol |
| 4 | (+)-3c (Handratta, 2005) | (+)-6-(7-Hydroxy-6,7-dihydro-5H-pyrrolo[1,2-c]imidazol-7-yl)-N-methyl-2-naphthamide |
| 5 | 13 (Budha, 2008) | 1-(4'-Fluoro[1,1'-biphenyl]-3-yl)-1-(1H-imidazol-4-yl)-2-methyl-1-propanol |
| 6 | 24 (Budha, 2008) | N-{4'-[1-Hydroxy-1-(1H-imidazol-4-yl)-2-methylpropyl][1,1'-biphenyl]-3-yl}-N'-methylurea |
| 7 | 17 (Budha, 2008) | N-{4'-[1-Hydroxy-1-(1H-imidazol-4-yl)-2-methylpropyl][1,1'-biphenyl]-3-y}acetamide |
| 8 | L26 (Nnane, 1999) | 4,16-pregnadiene-3,20-dione-20-oxime acetate |
| 9 | 15 (Budha, 2008) | 1-(4'-Fluoro[1,1'-biphenyl]-4-yl)-1-(1H-imidazol-4-yl)-2-methyl-1-propanol |
| 10 | 16 (Budha, 2008) | 1-(4'-Chloro[1,1'-biphenyl]-4-yl)-1-(1H-imidazol-4-yl)-2-methyl-1-propanol |
| 11 | TAK700a (Jagusch, 2008) | [(1S)-1-(6,7-dimethoxy-2-naphthyl)-1-(1H-imidazol-4-yl)-2-methylpropan-1-ol] |
| 12 | 3b (Kaku, 2011a) | 6-(7-Hydroxy-6,7-dihydro-5H-pyrrolo[1,2-c]imidazol-7-yl)-2-naphthamide |
| 13 | 7 (Budha, 2008) | 1-[1,1'-Biphenyl]-4-yl-1-(1H-imidazol-4-yl)-2-methyl-1-propanol |
| 14 | 26 (Budha, 2008) | N-{6-(4-[1-Hydroxy-1-(1H-imidazol-4-yl)-2-methylpropyl]phenyl)-2-pyridyl}acetamide |
| 15 | 16 (Budha, 2008) | [(3'-Hydroxy-4'-Hydroxybiphenyl-4-yl)(pyridin-4-yl)1-isopropylidenemethane] |
| 16 | 32 (Budha, 2008) | N-[4'-[1-Hydroxy-1-(1H-imidazol-4-yl)ethyl][1,1'-biphenyl]-3-yl]acetamide |
| 17 | 33 (Budha, 2008) | N-[4'-[1-Hydroxy-1-(1H-imidazol-4-yl)propyl][1,1'-biphenyl]-3-yl]acetamide |
| 18 | 22 (Budha, 2008) | 4'-[1-Hydroxyl-(1H-imidazol-4-yl)-2-methylpropyl]-Nmethyl[1,1'-biphenyl]-3-carboxamide |
| 19 | 34 (Budha, 2008) | N-[4'-[Cyclopropyl(hydroxy)-1H-imidazol-4-ylmethyl][1,1'-biphenyl]-3-yl]acetamide |
| 20 | 14 (Budha, 2008) | 1-(4'-Chloro[1,1'-biphenyl]-3-yl)-1-(1H-imidazol-4-yl)-2-methyl-1-propanol |
| 21 | L6 (Nnane, 1999) | 17-(4'-imidazolyl)androsta-4,16-dien-3-one |
| 22 | 9 (Hu, 2010a) | 4'-(Pyridin-4-ylmethyl)biphenyl-3,4-diol |
| 23 | 9a (Hu, 2010a) | 4-[(3',4'-Dimethoxybiphenyl-4-yl)methyl]pyridine |
| 24 | 26 (Jagusch, 2008) | [(3'-Hydroxy-4'-Hydroxybiphenyl-4-yl)(pyridin-4-yl)methane] |
| 25 | 8 (Budha, 2008) | 1-(1H-Imidazol-4-yl)-1-(4'-methoxy[1,1'-biphenyl]-4-yl)-2-methyl-1-propanol |
| 26 | 13 (Jagusch, 2008) | [(3'-Hydroxybiphenyl-4-yl)(pyridin-4-yl)1-isopropylidenemethane] |
| 27 | 20 (Kaku, 2011a) | 2-Fluoro-4-(5-(pyridin-4-yl)-5,6,7,8-tetrahydronaphthalen-2-yl)phenol Hydrobromide |
| 28 | 15 (Jagusch, 2008) | [(3'-Fluoro-4'-Hydroxybiphenyl-4-yl)(pyridin-4-yl)1-isopropylidenemethane] |
| 29 | 22 (Jagusch, 2008) | [(3'-Amino-4'-Aminobiphenyl-4-yl)(pyridin-4-yl)1-isopropylidenemethane] |
| 30 | L12 (Nnane, 1999) | N-[4'-[1-Hydroxy(1H-imidazol-4-yl)methyl][1,1'-biphenyl]-3-yl]acetamide |
| 31 | 36 (Budha, 2008) | 6-(7-Hydroxy-6,7-dihydro-6,6-dimethyl-5H-pyrrolo[1,2-c]imidazol-7-yl)-N-ethyl-2-naphthamide |
| 32 | 3i (Kaku, 2011a) | 4-[(3'-Hydroxybiphenyl-4-yl)methyl]pyridine |
| 33 | 8 (Hu, 2010a) | 3β-acetoxy-17-(4'-imidazoly)androsta-5,16-diene |
| 34 | 24 (Jagusch, 2008) | [(3'-Hydroxybiphenyl-4-yl)(pyridin-4-yl)methane] |
| 35 | L38 (Nnane, 1999) | N-{4'-[1-Hydroxy-1-(1H-imidazol-4-yl)-2-methylpropyl][1,1'-biphenyl]-4-yl}acetamide |
| 36 | 18 (Budha, 2008) | 1-(1H-Imidazol-4-yl)-1-(4'-methoxy-[1,1'-biphenyl]-3-yl)-2-methyl-1-propanol |
| 37 | 6 (Budha, 2008) | 4-(5-(Pyridin-4-yl)-5,6,7,8-tetrahydronaphthalen-2-yl)benzene-1,2-diol Hydrobromide |
| 38 | 19 (Kaku, 2011a) | 4'-[1-Hydroxy-1-(1H-imidazol-4-yl)-2-methylpropyl]-Nmethyl[1,1'-biphenyl]-3-sulfonamide |
| 39 | 25 (Budha, 2008) | 17-(5'-isoxazolyl)androsta-5,16-dien-3β-ol |
| 40 | 23 (Budha, 2008) | 4-(6-(4-Fluorophenyl)-1,2,3,4-tetrahydronaphthalen-1-yl)pyridineHydrochloride |
| 41 | 17 (Kaku, 2011a) | 4[1-(1Himidazolyl)ethyl]biphenyl |
| 42 | 5ax (Hu, 2010a) | 3-Fluoro-4'-(pyridin-4-ylmethyl)biphenyl-4-ol |
| 43 | 10 (Hu, 2010a) | 2-Fluoro-4-(5-(pyridin-4-yl)-7,8-dihydronaphthalen-2-yl)phenolHydrobromide |
| 44 | 14 (Kaku, 2011a) | [(3'-Fluoro-4'-Hydroxybiphenyl-4-yl)(pyridin-4-yl)methane] |
| 45 | 25 (Jagusch, 2008) | N-Ethyl-6-(7-hydroxy-6,7-dihydro-5H-pyrrolo[1,2-c]-imidazol-7-yl)-2-naphthamide |
| 46 | 3e (Kaku, 2011a) | [(3'-Hydroxybiphenyl-4-yl)(pyridin-4-yl)1-ethylmethane] |
| 47 | 11 (Jagusch, 2008) | [(3'-Aminobiphenyl-4-yl)(pyridin-4-yl)methane] |
| 48 | 27 (Jagusch, 2008) | 1-(1-(2-Fluoro-4-(4-methylthiophen-3-yl)-phenyl)propyl)-1H-imidazole |
| 49 | 16 (Kaku, 2011a) | 4-fluoro-4-[1-(1H-imidazolyl)ethyl]biphenyl |
| 50 | 30 (Budha, 2008) | 4-[(4'-Hydroxybiphenyl-4-yl)methyl]pyridine |
| 51 | 5ay (Hu, 2010a) | 1-(1H-imidazolyl)-5-phenylindane |
| 52 | 4 (Hu, 2010a) | 1-(1-(4-(2-Chlorothiophen-3-yl)-phenyl)propyl)-1H-imidazole |
| 53 | 5bx (Hu, 2010a) | N-Cyclopropyl-6-(7-hydroxy-6,7-dihydro-5H-pyrrolo[1,2-c]imidazol-7-yl)-2-naphthamide |
| 54 | 31 (Budha, 2008) | 4-(5-(4-Fluorophenyl)-2,3-dihydro-1H-inden-1-yl)pyridine Hydrochloride |
| 55 | 3f (Kaku, 2011a) | (20S)-21-iminopregn-5,14-dien-3β-ol |
| 56 | 5 (Handratta, 2005) | 3β-hydroxy-17-(1H-benzimidazole-1-yl)androsta-5,16-diene |
| 57 | 5 [Kaku, 2011b) | 4-(5-(Pyridin-4-yl)-7,8-dihydronaphthalen-2-yl)benzene-1,2-diol Hydrobromide |
| 58 | 13 (Kaku, 2011a) | 5-(4-Fluorophenyl)-1-(pyridin-4-yl)-2,3-dihydro-1H-inden-1-ol |
| 59 | 2 (Kaku, 2011a) | [(3'-Amino-4'-Aminobiphenyl-4-yl)(pyridin-4-yl)methane] |
| 60 | 28 (Jagusch, 2008) | [(3'-Fluoro-4'-Hydroxybiphenyl-4-yl)(pyridin-4-yl)1-ethylmethane] |
| 61 | 14 (Jagusch, 2008) | 1-(1-(4-Thiophen-3-yl-phenyl)propyl)-1H-imidazole |
| 62 | 27 (Budha, 2008) | 6-(7-Hydroxy-6,7-dihydro-5H-pyrrolo[1,2-c]imidazol-7-yl)-N-isopropyl-2-naphthamide |
| 63 | 14 (Hu, 2010a) | 6-[1-Hydroxy-1-(1-methyl-1H-imidazol-5-yl)ethyl]-N-methylnaphthalene-2-carboxamide |
| 64 | 3g (Kaku, 2011a) | 4-(4-Bromobenzyl)pyridine |
| 65 | 3j ((Kaku, 2011a) | 6-(3,4-Difluorophenyl)-1-(pyridin-4-yl)-1,2,3,4-tetrahydronaphthalen-1-ol |
| 66 | 5a (Hu, 2010a) | 6-[4-(Pyridin-4-ylmethyl)phenyl]naphthalen-2-ol |

TABLE 4-continued

IUPAC Systematic Names for known CYP 17A1 inhibitors used to generate Pharmacophore Models:

| ID | Code [Ref] | Systematic Name |
|---|---|---|
| 67 | 6 (Kaku, 2011a) | [(4'-Methylbiphenyl-4-yl)(pyridin-4-yl)1-isopropylidenemethane] |
| 68 | 25 (Hu, 2010a) | 4-[4-(Thiophen-2-yl)benzyl]pyridine |
| 69 | 18 (Jagusch, 2008) | 4-[(4'-Fluorobiphenyl-4-yl)methyl]-pyridine |
| 70 | 15 [37] | 6-(4-Fluorophenyl)-1-(pyridin-4-yl)-1,2,3,4-tetrahydronaphthalen-1-ol |
| 71 | 21 (Hu, 2010a) | 1-(1-(4-(4-Methylthiophen-3-yl)phenyl)propyl)-1H-imidazole |
| 72 | 5 (Kaku, 2011a) | 4-[(3',4'-Difluorobiphenyl-4-yl)methyl]pyridine |
| 73 | 29 (Budha, 2008) | 4-[4-(Thiophen-3-yl)benzyl]pyridine |
| 74 | 15 (Hu, 2010a) | 1-[4-(4-{[(2R,4S)-2-(2,4-Dichlorophenyl)-2-(1H-imidazol-1-ylmethyl)-1,3-dioxolan-4-yl]methoxy}phenyl)piperazin-1-yl]ethan-1-one |
| 75 | 22 (Hu, 2010a) | 5-[4-(Pyridin-4-ylmethyl)phenyl]-1H-indole |
| 76 | KTZ (Jagusch, 2008) | [(3'-Hydroxybiphenyl-4-yl)(pyridin-4-yl)1-isopropylmethane] |
| 77 | 23 (Hu, 2010a) | 3β-hydroxy-17-(5(1)-pyrimidyl) androsta-5,16-diene |
| 78 | 12 (Jagusch, 2008) | [(3'-Fluoro-4'-Methylbiphenyl-4-yl)(pyridin-4-yl)1-isopropylidenemethane] |
| 79 | 19 (Jagusch, 2008) | N-(4'-Isonicotinoylbiphenyl-3-yl)acetamide |
| 80 | 12 (Hu, 2010a) | 1-(1-(4-Thiophen-3-ylphenyl)ethyl)-1H-imidazole |
| 81 | 28 (Budha, 2008) | 4-(6-(3,4-Difluorophenyl)-1,2,3,4-tetrahydronaphthalen-1-yl)pyridine Hydrochloride |
| 82 | 18 (Kaku, 2011a) | tert-Butyl 4'-(Pyridin-4-ylmethyl)biphenyl-4-ylcarbamate |
| 83 | 17 (Hu, 2010a) | [(3'-Methylbiphenyl-4-yl)(pyridin-4-yl)1-isopropylidenemethane] |
| 84 | 17 (Jagusch, 2008) | 4'-(Pyridin-4-ylmethyl)biphenyl-4-carboxamide |
| 85 | 13 (Hu, 2010a) | 4-[4-(6-Methoxynaphthalen-2-yl)benzyl]pyridine |
| 86 | 24 (Hu, 2010a) | 3-(5-(4-Fluorophenyl)-3H-inden-1-yl)pyridine Hydrochloride |
| 87 | 8 (Kaku, 2011a) | 4-[(3'-Fluoro-4'-methoxybiphenyl-4-yl)methyl]pyridine |
| 88 | 16 (Hu, 2010a) | 6-(3-Fluoro-4-methoxyphenyl)-1-(pyridin-4-yl)-1,2,3,4-tetrahydronaphthalen-1-ol |
| 89 | 7 (Kaku, 2011a) | 4-(5-(4-Methoxyphenyl)-3H-inden-1-yl)pyridine |
| 90 | 10 (Kaku, 2011a) | 4-(6-(4-Fluorophenyl)-3,4-dihydronaphthalen-1-yl)pyridine |
| 91 | 11 (Kaku, 2011a) | 1-(1H-Imidazol-4-yl)-2-methyl-1-[4-(2-pyridinyl)phenyl]-1-propanol |
| 92 | 12 (Kaku, 2011a) | 4-(6-(3,4-Difluorophenyl)-3,4-dihydronaphthalendihydronaphthalen-1-yl)pyridine |
| 93 | 4 (Kaku, 2011a) | 5-(3-Fluoro-4-methoxyphenyl)-1-(pyridin-4-yl)-2,3-dihydro-1H-inden-1-ol |
| 94 | 20 (Jagusch, 2008) | [(3'-Methyl-4'-Methylbiphenyl-4-yl)(pyridin-4-yl)1-isopropylidenemethane] |
| 95 | 1 (Kaku, 2011a) | 5-(4-Fluorophenyl)-1-(pyridin-4-yl)-2,3-dihydro-1H-inden-1-ol |
| 96 | 3 (Kaku, 2011a) | 5-(4-Methoxyphenyl)-1-(pyridin-4-yl)-2,3-dihydro-1H-inden-1-ol |
| 97 | 9 (Kaku, 2011a) | 4-(5-(4-Fluorophenyl)-3H-inden-1-yl)pyridine Hydrochloride |
| 98 | 15 (Kaku, 2011a) | 3-(5-(4-Fluorophenyl)-2,3-dihydro-1H-inden-1-yl)pyridine Hydrochloride |

1. [a]KTZ - Ketoconazole

TABLE 4A

Actual activity versus Predicted Activity of Preferred Pharmacophore Model AADDRR.860. (See also FIG. 8 in the accompanying Drawings):

(Part 1):

| Entry ID | Entry Name | phase qsar set | IC50 | pIC50 | Fitness Score | phase predicted activity1 | phase predicted activity2 | phase predicted activity3 |
|---|---|---|---|---|---|---|---|---|
| 1 | (+)-3c [11]. | training | 19.000 | 7.720 | 0.836 | 7.280 | 7.850 | 7.610 |
| 2 | 1 [11]. | training | 16.000 | 7.800 | 0.993 | 7.410 | 7.510 | 7.450 |
| 3 | 1 [13]. | training | 20000.000 | 4.700 | 1.705 | 6.100 | 5.270 | 4.930 |
| 4 | 2 [13]. | training | 333.000 | 6.480 | 1.051 | 6.330 | 6.310 | 6.270 |
| 5 | 3 [13]. | test | 20000.000 | 4.700 | 1.153 | 5.440 | 5.370 | 5.090 |
| 6 | 3b [11]. | training | 29.000 | 7.540 | 1.078 | 7.160 | 7.130 | 6.980 |
| 7 | 3d [11]. | training | 13.000 | 7.890 | 0.887 | 7.120 | 7.550 | 7.460 |
| 8 | 3e [11]. | training | 190.000 | 6.720 | 0.695 | 7.060 | 7.020 | 6.610 |
| 9 | 3f [11]. | test | 290.000 | 6.540 | 0.465 | 6.940 | 6.950 | 6.620 |
| 10 | 3g [11]. | training | 400.000 | 6.400 | 0.653 | 7.010 | 6.990 | 6.560 |
| 11 | 3i [11]. | test | 88.000 | 7.060 | 0.699 | 7.140 | 7.460 | 7.130 |
| 12 | 3j [11]. | training | 410.000 | 6.390 | 0.878 | 7.080 | 6.870 | 6.500 |
| 13 | 4 [9]. | test | 248.000 | 6.610 | 1.444 | 6.620 | 6.670 | 6.710 |
| 14 | 4 [13]. | training | 10000.000 | 5.000 | 1.145 | 5.410 | 5.320 | 5.020 |
| 15 | 5 [12]. | test | 18.000 | 7.740 | 1.651 | 7.070 | 7.690 | 7.550 |
| 16 | 5 [13]. | training | 587.000 | 6.230 | 1.596 | 6.110 | 5.910 | 6.210 |
| 17 | 5ax [7]. | training | 170.000 | 6.770 | 1.376 | 6.170 | 6.450 | 6.770 |
| 18 | 5ay [7]. | training | 240.000 | 6.620 | 1.616 | 6.280 | 6.240 | 6.520 |
| 19 | 5bx [7]. | training | 250.000 | 6.600 | 1.370 | 6.200 | 6.160 | 6.410 |
| 20 | 6 [12]. | training | 130.000 | 6.890 | 1.282 | 7.170 | 7.060 | 7.010 |
| 21 | 6 [13]. | training | 423.000 | 6.370 | 1.622 | 6.150 | 5.960 | 6.250 |
| 22 | 7 [12]. | training | 33.000 | 7.480 | 2.009 | 7.060 | 7.080 | 7.480 |
| 23 | 7 [13]. | test | 5000.000 | 5.300 | 1.245 | 6.000 | 6.080 | 6.020 |
| 24 | 8 [9]. | training | 97.000 | 7.010 | 1.830 | 6.700 | 6.770 | 7.020 |
| 25 | 8 [12]. | training | 54.000 | 7.270 | 1.111 | 7.390 | 7.270 | 7.130 |
| 26 | 8 [13]. | training | 2346.000 | 5.630 | 1.149 | 5.940 | 5.750 | 5.650 |

TABLE 4A-continued

Actual activity versus Predicted Activity of Preferred Pharmacophore Model
AADDRR.860. (See also FIG. 8 in the accompanying Drawings):

| | | | | | | | | |
|---|---|---|---|---|---|---|---|---|
| 27 | 9 [9]. | training | 52.000 | 7.280 | 1.504 | 7.090 | 7.300 | 7.160 |
| 28 | 9a [9]. | training | 52.000 | 7.280 | 1.384 | 6.810 | 7.150 | 7.170 |
| 29 | 10 [9]. | training | 186.000 | 6.730 | 1.450 | 6.590 | 6.610 | 6.660 |
| 30 | 10 [13]. | training | 5000.000 | 5.300 | 1.190 | 5.480 | 5.370 | 5.190 |
| 31 | 11 [2]. | training | 189.000 | 6.720 | 2.064 | 6.860 | 6.490 | 6.600 |
| 32 | 12 [2]. | training | 783.000 | 6.110 | 1.884 | 6.670 | 6.400 | 6.440 |
| 33 | 12 [9]. | training | 876.000 | 6.050 | 2.073 | 6.680 | 6.360 | 6.130 |
| 34 | 13 [2]. | training | 56.000 | 7.250 | 1.984 | 6.960 | 6.850 | 7.150 |
| 35 | 13 [9]. | test | 1790.000 | 5.750 | 1.636 | 6.060 | 6.160 | 6.160 |
| 36 | 13 [12]. | test | 19.000 | 7.720 | 1.694 | 7.070 | 7.650 | 7.500 |
| 37 | 13 [13]. | training | 307.000 | 6.510 | 1.518 | 6.840 | 6.920 | 6.650 |
| 38 | 14 [2]. | training | 343.000 | 6.460 | 1.443 | 6.670 | 6.640 | 6.600 |
| 39 | 14 [12]. | training | 49.000 | 7.310 | 1.697 | 7.070 | 7.590 | 7.440 |
| 40 | 14 [13]. | training | 188.000 | 6.730 | 1.480 | 6.600 | 6.570 | 6.620 |
| 41 | 15 [2]. | training | 75.000 | 7.120 | 1.232 | 6.110 | 7.350 | 7.430 |
| 42 | 15 [12]. | test | 27.000 | 7.570 | 2.001 | 7.000 | 7.000 | 7.380 |
| 43 | 15 [13]. | training | 20000.000 | 4.700 | 1.287 | 5.800 | 5.180 | 4.980 |
| 44 | 16 [2]. | training | 37.000 | 7.430 | 1.476 | 7.000 | 7.180 | 7.120 |
| 45 | 16 [9]. | training | 3340.000 | 5.480 | 1.137 | 5.330 | 5.280 | 5.260 |
| 46 | 16 [12]. | training | 28.000 | 7.550 | 1.999 | 6.980 | 6.990 | 7.370 |
| 47 | 17 [9]. | training | 1370.000 | 5.860 | 1.351 | 5.610 | 5.930 | 5.940 |
| 48 | 17 [12]. | training | 24.000 | 7.620 | 3.000 | 7.670 | 7.520 | 7.700 |
| 49 | 18 [12]. | training | 120.000 | 6.920 | 1.808 | 7.450 | 7.250 | 7.060 |
| 50 | 19 [13]. | training | 144.000 | 6.840 | 1.522 | 6.880 | 6.890 | 6.650 |
| 51 | 20 [13]. | training | 64.000 | 7.190 | 1.231 | 6.100 | 7.350 | 7.430 |
| 52 | 22 [2]. | training | 75.000 | 7.120 | 1.998 | 7.010 | 6.820 | 7.070 |
| 53 | 22 [12]. | training | 44.000 | 7.360 | 2.456 | 7.660 | 7.440 | 7.450 |
| 54 | 23 [9]. | training | 760.000 | 6.120 | 1.482 | 6.420 | 6.390 | 6.330 |
| 55 | 23 [12]. | training | 160.000 | 6.800 | 2.347 | 7.330 | 7.010 | 7.020 |
| 56 | 24 [2]. | training | 97.000 | 7.010 | 1.829 | 6.700 | 6.770 | 7.020 |
| 57 | 24 [9]. | training | 2000.000 | 5.700 | 1.165 | 5.580 | 5.610 | 5.500 |
| 58 | 24 [12]. | test | 21.000 | 7.680 | 2.978 | 7.660 | 7.500 | 7.670 |
| 59 | 25 [2]. | training | 186.000 | 6.730 | 1.517 | 6.840 | 6.870 | 6.800 |
| 60 | 25 [9]. | training | 438.000 | 6.360 | 1.259 | 6.580 | 6.780 | 6.590 |
| 61 | 25 [12]. | training | 150.000 | 6.820 | 2.028 | 7.090 | 7.030 | 7.370 |
| 62 | 26 [2]. | training | 52.000 | 7.280 | 1.504 | 7.090 | 7.300 | 7.160 |
| 63 | 26 [12]. | training | 36.000 | 7.440 | 2.642 | 7.520 | 7.440 | 7.570 |
| 64 | 27 [2]. | test | 226.000 | 6.650 | 2.008 | 6.840 | 6.680 | 6.710 |
| 65 | 27 [10]. | test | 373.000 | 6.430 | 1.500 | 6.480 | 6.180 | 6.340 |
| 66 | 28 [2]. | training | 337.000 | 6.470 | 2.021 | 6.900 | 6.690 | 6.670 |
| 67 | 28 [10]. | training | 953.000 | 6.020 | 1.454 | 6.460 | 6.200 | 6.300 |
| 68 | 29 [10]. | training | 584.000 | 6.230 | 1.648 | 6.470 | 6.120 | 6.350 |
| 69 | 30 [10]. | training | 236.000 | 6.630 | 1.634 | 6.510 | 6.240 | 6.480 |
| 70 | 31 [10]. | training | 263.000 | 6.580 | 1.680 | 6.530 | 6.200 | 6.450 |
| 71 | 32 [12]. | training | 38.000 | 7.420 | 2.616 | 7.490 | 7.380 | 7.400 |
| 72 | 33 [12]. | training | 40.000 | 7.400 | 2.915 | 7.590 | 7.440 | 7.540 |
| 73 | 34 [12]. | test | 45.000 | 7.350 | 2.584 | 7.470 | 7.310 | 7.360 |
| 74 | 36 [12]. | training | 77.000 | 7.110 | 1.647 | 6.730 | 6.770 | 6.740 |
| 75 | Ketoconazole. | training | 740.000 | 6.130 | 1.125 | 6.300 | 6.180 | 5.990 |
| 76 | TAK700. | training | 28.000 | 7.550 | 0.948 | 7.090 | 7.920 | 7.810 |
| 77 | 2c [20]. | test | 180.000 | 6.740 | 1.264 | 7.110 | 7.400 | 7.170 |
| 78 | 6 [20]. | test | 69.000 | 7.160 | 0.991 | 6.770 | 7.040 | 6.950 |

(Part 2):

| Entry ID | Entry Name | phase qsar set | Num Sites Matched | Matched Ligand Sites | Align Score | Vector Score | Volume Score |
|---|---|---|---|---|---|---|---|
| 1 | (+)-3c [11]. | training | 6 | A(1) A(3) D(4) D(5) R(9) R(8) | 1.288 | 0.462 | 0.447 |
| 2 | 1 [11]. | training | 6 | A(1) A(3) D(4) D(6) R(10) R(11) | 1.321 | 0.534 | 0.560 |
| 3 | 1 [13]. | training | 4 | A(1) A(—) D(3) D(—) R(6) R(8) | 0.839 | 0.766 | 0.638 |
| 4 | 2 [13]. | training | 4 | A(1) A(—) D(3) D(—) R(6) R(8) | 0.969 | 0.327 | 0.532 |
| 5 | 3 [13]. | test | 4 | A(3) A(—) D(—) D(4) R(9) R(7) | 1.077 | 0.689 | 0.362 |
| 6 | 3b [11]. | training | 6 | A(1) A(3) D(4) D(5) R(10) R(9) | 1.444 | 0.710 | 0.571 |
| 7 | 3d [11]. | training | 5 | A(1) A(2) D(—) D(3) R(7) R(6) | 1.382 | 0.531 | 0.507 |
| 8 | 3e [11]. | training | 6 | A(1) A(3) D(4) D(5) R(10) R(9) | 1.599 | 0.508 | 0.519 |
| 9 | 3f [11]. | test | 6 | A(1) A(3) D(4) D(5) R(9) R(10) | 1.553 | 0.285 | 0.474 |
| 10 | 3g [11]. | training | 6 | A(1) A(3) D(4) D(5) R(10) R(9) | 1.634 | 0.509 | 0.505 |
| 11 | 3i [11]. | test | 6 | A(1) A(3) D(4) D(5) R(12) R(11) | 1.271 | 0.351 | 0.407 |
| 12 | 3j [11]. | training | 6 | A(1) A(3) D(4) D(5) R(8) R(9) | 1.317 | 0.437 | 0.539 |
| 13 | 4 [9]. | test | 3 | A(—) A(—) D(—) D(3) R(5) R(6) | 0.908 | 0.702 | 0.499 |
| 14 | 4 [13]. | training | 4 | A(3) A(—) D(—) D(4) R(10) R(8) | 1.078 | 0.688 | 0.355 |
| 15 | 5 [12]. | test | 4 | A(—) A(1) D(—) D(3) R(9) R(8) | 0.790 | 0.801 | 0.508 |
| 16 | 5 [13]. | training | 3 | A(2) A(—) D(—) D(—) R(6) R(8) | 0.877 | 0.813 | 0.515 |
| 17 | 5ax [7]. | training | 4 | A(1) A(—) D(2) D(—) R(6) R(5) | 1.023 | 0.694 | 0.534 |
| 18 | 5ay [7]. | training | 3 | A(1) A(—) D(2) D(—) R(—) R(7) | 0.969 | 0.855 | 0.568 |
| 19 | 5bx [7]. | training | 4 | A(1) A(—) D(2) D(—) R(6) R(5) | 1.105 | 0.750 | 0.541 |

TABLE 4A-continued

Actual activity versus Predicted Activity of Preferred Pharmacophore Model
AADDRR.860. (See also FIG. 8 in the accompanying Drawings):

| | | | | | | | |
|---|---|---|---|---|---|---|---|
| 20 | 6 [12]. | training | 5 | A(1) A(3) D(4) D(—) R(11) R(10) | 1.258 | 0.739 | 0.591 |
| 21 | 6 [13]. | training | 3 | A(2) A(—) D(—) D(—) R(7) R(9) | 0.877 | 0.813 | 0.541 |
| 22 | 7 [12]. | training | 4 | A(1) A(—) D(3) D(—) R(8) R(9) | 0.693 | 0.807 | 0.780 |
| 23 | 7 [13]. | test | 4 | A(3) A(—) D(—) D(4) R(10) R(8) | 1.063 | 0.775 | 0.356 |
| 24 | 8 [9]. | training | 3 | A(—) A(—) D(—) D(3) R(5) R(6) | 0.849 | 0.973 | 0.564 |
| 25 | 8 [12]. | training | 5 | A(1) A(3) D(4) D(—) R(11) R(10) | 1.413 | 0.725 | 0.564 |
| 26 | 8 [13]. | training | 3 | A(1) A(—) D(—) D(—) R(5) R(6) | 1.030 | 0.485 | 0.523 |
| 27 | 9 [9]. | training | 4 | A(—) A(2) D(—) D(5) R(7) R(6) | 0.937 | 0.726 | 0.558 |
| 28 | 9a [9]. | training | 3 | A(—) A(3) D(—) D(—) R(7) R(8) | 0.971 | 0.680 | 0.513 |
| 29 | 10 [9]. | training | 3 | A(—) A(—) D(3) D(—) R(6) R(5) | 0.907 | 0.701 | 0.505 |
| 30 | 10 [13]. | training | 3 | A(2) A(—) D(—) D(—) R(7) R(6) | 1.005 | 0.664 | 0.364 |
| 31 | 11 [2]. | training | 3 | A(—) A(—) D(—) D(3) R(6) R(5) | 0.849 | 0.973 | 0.798 |
| 32 | 12 [2]. | training | 3 | A(—) A(—) D(—) D(3) R(6) R(5) | 0.849 | 0.973 | 0.619 |
| 33 | 12 [9]. | training | 5 | A(3) A(2) D(—) D(4) R(6) R(5) | 0.589 | 0.918 | 0.645 |
| 34 | 13 [2]. | training | 3 | A(—) A(—) D(—) D(3) R(7) R(6) | 0.849 | 0.973 | 0.719 |
| 35 | 13 [9]. | test | 4 | A(2) A(—) D(4) D(—) R(5) R(6) | 0.807 | 0.846 | 0.463 |
| 36 | 13 [12]. | test | 4 | A(—) A(1) D(—) D(3) R(10) R(9) | 0.790 | 0.802 | 0.551 |
| 37 | 13 [13]. | training | 4 | A(—) A(3) D(—) D(4) R(8) R(7) | 0.937 | 0.784 | 0.515 |
| 38 | 14 [2]. | training | 3 | A(—) A(—) D(—) D(3) R(7) R(6) | 0.907 | 0.701 | 0.498 |
| 39 | 14 [12]. | training | 4 | A(—) A(1) D(—) D(3) R(10) R(9) | 0.790 | 0.801 | 0.554 |
| 40 | 14 [13]. | training | 3 | A(—) A(—) D(—) D(3) R(7) R(6) | 0.907 | 0.701 | 0.535 |
| 41 | 15 [2]. | training | 3 | A(—) A(—) D(3) D(—) R(7) R(8) | 0.876 | 0.623 | 0.339 |
| 42 | 15 [12]. | test | 4 | A(1) A(—) D(3) D(—) R(9) R(10) | 0.693 | 0.807 | 0.771 |
| 43 | 15 [13]. | training | 3 | A(1) A(—) D(—) D(—) R(5) R(6) | 0.934 | 0.515 | 0.550 |
| 44 | 16 [2]. | training | 4 | A(—) A(2) D(—) D(5) R(9) R(8) | 0.937 | 0.727 | 0.530 |
| 45 | 16 [9]. | training | 3 | A(2) A(—) D(—) D(—) R(7) R(6) | 1.005 | 0.638 | 0.336 |
| 46 | 16 [12]. | training | 4 | A(1) A(—) D(3) D(—) R(9) R(10) | 0.693 | 0.807 | 0.769 |
| 47 | 17 [9]. | training | 4 | A(3) A(—) D(4) D(—) R(6) R(7) | 0.798 | 0.608 | 0.408 |
| 48 | 17 [12]. | training | 6 | A(1) A(3) D(4) D(5) R(10) R(11) | 0.000 | 1.000 | 1.000 |
| 49 | 18 [12]. | training | 5 | A(1) A(—) D(4) D(5) R(10) R(11) | 0.960 | 0.934 | 0.674 |
| 50 | 19 [13]. | training | 4 | A(—) A(3) D(—) D(4) R(8) R(7) | 0.937 | 0.783 | 0.519 |
| 51 | 20 [13]. | training | 3 | A(—) A(—) D(3) D(—) R(6) R(7) | 0.876 | 0.623 | 0.338 |
| 52 | 22 [2]. | training | 3 | A(—) A(—) D(—) D(5) R(9) R(8) | 0.849 | 0.996 | 0.709 |
| 53 | 22 [12]. | training | 6 | A(1) A(3) D(4) D(5) R(10) R(11) | 0.350 | 0.895 | 0.853 |
| 54 | 23 [9]. | training | 3 | A(—) A(—) D(—) D(2) R(5) R(4) | 0.961 | 0.811 | 0.471 |
| 55 | 23 [12]. | training | 6 | A(1) A(2) D(5) D(6) R(11) R(12) | 0.454 | 0.927 | 0.797 |
| 56 | 24 [2]. | training | 3 | A(—) A(—) D(—) D(3) R(5) R(4) | 0.849 | 0.973 | 0.564 |
| 57 | 24 [9]. | training | 3 | A(2) A(—) D(—) D(—) R(6) R(5) | 0.993 | 0.635 | 0.357 |
| 58 | 24 [12]. | test | 6 | A(1) A(3) D(4) D(5) R(11) R(12) | 0.004 | 1.000 | 0.982 |
| 59 | 25 [2]. | training | 3 | A(—) A(—) D(—) D(3) R(6) R(5) | 0.907 | 0.697 | 0.575 |
| 60 | 25 [9]. | training | 3 | A(—) A(—) D(—) D(3) R(5) R(4) | 1.061 | 0.851 | 0.292 |
| 61 | 25 [12]. | training | 4 | A(2) A(—) D(4) D(—) R(10) R(9) | 0.693 | 0.828 | 0.778 |
| 62 | 26 [2]. | training | 4 | A(—) A(2) D(—) D(5) R(7) R(6) | 0.937 | 0.726 | 0.558 |
| 63 | 26 [12]. | training | 6 | A(2) A(4) D(5) D(6) R(11) R(12) | 0.317 | 0.989 | 0.917 |
| 64 | 27 [2]. | test | 3 | A(—) A(—) D(—) D(2) R(5) R(4) | 0.849 | 0.980 | 0.735 |
| 65 | 27 [10]. | test | 3 | A(D A(—) D(—) D(—) R(5) R(4) | 0.931 | 0.635 | 0.642 |
| 66 | 28 [2]. | training | 3 | A(—) A(—) D(—) D(3) R(7) R(6) | 0.849 | 0.996 | 0.733 |
| 67 | 28 [10]. | training | 3 | A(1) A(—) D(—) D(—) R(5) R(4) | 0.936 | 0.613 | 0.621 |
| 68 | 29 [10]. | training | 3 | A(1) A(—) D(—) D(—) R(6) R(5) | 0.931 | 0.761 | 0.663 |
| 69 | 30 [10]. | training | 3 | A(1) A(—) D(—) D(—) R(7) R(6) | 0.930 | 0.752 | 0.657 |
| 70 | 31 [10]. | training | 3 | A(1) A(—) D(—) D(—) R(6) R(5) | 0.933 | 0.780 | 0.677 |
| 71 | 32 [12]. | training | 6 | A(1) A(3) D(4) D(5) R(8) R(9) | 0.286 | 0.990 | 0.864 |
| 72 | 33 [12]. | training | 6 | A(1) A(3) D(4) D(5) R(9) R(10) | 0.056 | 0.999 | 0.962 |
| 73 | 34 [12]. | test | 6 | A(1) A(3) D(4) D(5) R(10) R(9) | 0.307 | 0.984 | 0.856 |
| 74 | 36 [12]. | training | 6 | A(1) A(3) D(4) D(5) R(8) R(9) | 0.634 | 0.527 | 0.649 |
| 75 | Ketoconazole. | training | 4 | A(3) A(5) D(—) D(—) R(10) R(11) | 1.237 | 0.764 | 0.392 |
| 76 | TAK700. | training | 5 | A(1) A(3) D(5) D(—) R(12) R(13) | 1.250 | 0.552 | 0.438 |
| 77 | 2c [20]. | test | 4 | A(3) A(2) D(—) D(5) R(12) R(—) | 1.017 | 0.761 | 0.350 |
| 78 | 6 [20]. | test | 5 | A(1) A(3) D(6) D(—) R(15) R(16) | 1.223 | 0.621 | 0.389 |

(Note:
This table is presented in two separate parts. Entry Names refer to compounds described in the references or journal articles which are listed at the foot of this specification under the heading NPL16 in the "Non-Patent Literature" section of the Citation List.
As an example of the nomenclature, Entry Name 3j[11] refers to compound 3j as described in the the article numbered as "11" under the heading NPL16.)

1.6 Prepare 3D Database for Advanced Pharmacophore Screening

The Manage 3D Database panel provides tools for preparing a structural database that can be searched for matches to a pharmacophore hypothesis. The database must contain all-atom 3D structures that are reasonable representations of the experimental structures. A total of 2.5 million drug-like structures downloaded from the Enamine database (www.e-namine.net) as an .sdf file, were added into the Manage 3D Database panel in the Maestro Graphical User Interface (GUI). The 3D database was prepared by generating ionization states for structures using Epik at pH 7.4. Default parameters were used to sample stereoisomers and perform conformational analysis. The tab for removing high energy ionization and/or tautomerization states was selected. Structures that did not satisfy Lipinski's rule of five in respect of physicochemical properties were removed. Conformers for structures that passed this filtering stage were generated and pharmacophore sites from selected features were created. Subsets of molecules for database searching as desired were also created.

1.7 Find Matches of Pharmacophore Hypothesis by Screening 3D Database

The Find Matches to Hypothesis panel is a single panel, with four sections. In the top two sections we specified the database as prepared in the previous section for searching. We also selected the hypothesis AADDRR.860 from the best 3D-QSAR model, to use in the search. We used default parameters for the search and for the subsequent display of hits. The search was performed in two steps: finding matches to the hypothesis, and fetching hits. In finding matches for the hypothesis in the database we opted to set a constraint that the hits had to match all six site points in the hypothesis. The second step can be repeated with different processing options without repeating the first step. The hits-processing options include adjusting the fitness score by which hits are sorted, applying numerical cut-offs in respect of the number of hits, and calculating activities using the QSAR model. The activities for the hits were predicted from the 3D-QSAR model and all hits were ranked according to the increase in predicted activities.

2. Molecular Docking Calculations 2.1 Search for Low Energy Conformers of Hits Using Macro Model Module The hits obtained from the database search were obtained as single conformers. Therefore, it was important to perform an extensive geometry optimization and conformational search of low-energy conformers prior to docking. We used OPLS_2005 as the force-field of choice using water as the solvent. We used PRCG as the method of minimization. The conformational search method was a mixed torsional/large-scale low-mode sampling for multiple ligands. We used default parameters for this conformational search. We enforced a filtering criterion for selecting low energy conformers, which was that all conformers with a relative potential energy lower than 0.5 kcal/mol would be further used in the next step.

2.2 Geometry Optimization of Hits Conformers Using Jaguar

The input structures for geometry optimization using Jaguar were obtained from output structures that survived the filtering step from the previous conformational search job. A Density Functional Theory (DFT) calculation was used as the optimal level of theory using a B3LYP 6-31G* basis set. During geometry optimization, Jaguar adjusts the convergence criteria for the SCF calculations at each geometry step for efficiency. The geometry is considered to have converged when the energy of successive geometries and the elements of the analytic gradient of the energy and the displacement have met the convergence criteria. In this case we selected a fully analytic convergence criterion with an initial guess looking for atomic overlaps. At the end of a geometry optimization Jaguar performs a simple analysis of the geometry optimization convergence. The number of steps for geometry optimization was set to 1000 because our structures are heterocyclic. We also used Poisson-Boltzmann (PBF) solvent model with water as an implicit water model. The electronic properties of interest calculated included molecular electrostatic potential (MESP) as well as highest occupied and lower unoccupied molecular orbital (HOMO and LUMO), respectively to explain the reactivity of the pharmacophore sites in our hits.

2.3 Enzyme Preparation

The x-ray crystal structures for CYP17A1 co-crystallized with CYP17A1 inhibitors TOK-001 or Galeterone (3SWZ) and Abiraterone (3RUK), respectively were downloaded from the protein databank PDB. These crystal structures have been crystalized and deposited into the Protein Data Bank (PDB) at a resolution of 2.6 Å and 2.4 Å, respectively. (For CYP19A1, the relevant PDB crystal structures are 3S7S, 3S79 & 4KQ8.)

PDB structures are protein-ligand complexes co-crystalized by x-ray crystallography, in some cases with XRD. However, typically a structure file from the PDB is not suitable for immediate use in molecular modelling calculations since a typical PDB structure file consists only of heavy atoms and may include a co-crystallized ligand, water molecules, metal ions, and cofactors. Some structures are multimers, and may need to be reduced to a single unit. Because of the limited resolution of X-ray experiments, it can be difficult to distinguish between NH and O groups, and the placement of these groups must be checked. PDB structures may also be missing information on connectivity, which must be assigned, along with bond orders and formal charges. After the x-ray crystal structure was imported from the PDB into the workspace, the structure was pre-processed to assign bond orders, hydrogen atoms were added, zero bond orders were added to metals, disulphide bonds were created, and missing side-chains and loops were filled in use the Prime module. Furthermore, waters beyond 5 Å from the hetero groups in the active site were deleted. Multiple structural units in the PDB structures existing as multimers were deleted so as to leave one structural unit. The ionization states for the amino acid residues of the enzyme and the ferric heme were generated at pH 7.4 using Epik. The resulting oxidation states were the +2 state for Fe of porphyrin and the +3 state. We opted for the (+3) state because ferric porphyrin in the resting state exists in this oxidation state in the catalytic cycle for the metabolism of substrates by the Cytochrome P450 enzymes. The enzyme was further optimized using Propka in order to assign the pKa values for amino acid residues.

2.4 High Throughput Virtual Screening Workflow (HTVSW) and Induced-Fit Docking (IFD)

The output files of hits from the geometry optimization were the source of ligands as inputs. The ligands were then docked against grid files for enzymes 3SWZ and 3RUK using a flexible ligand docking approach.

FIG. 7 shows native docking poses for a separate reference ligand TOK-001 (Galeterone) used for model validation.

Table 5 shows root-mean-square-deviations (RMSDs) in cross-docking and native docking approaches performed on different types of PDB x-ray crystal structures to validate and measure the selectivity of the docking methodology:

TABLE 5

Comparison of RMSDs

| PDB ID | Resolution Å | Docking Score (CD)[a] kcal/mol | RMSD (CD) Å | Docking Score (IFD)[b] kcal/mol | RMSD (IFD) Å | Enzyme/ Protein | Native ligand | Active Site | Type of Protein Enzyme |
|---|---|---|---|---|---|---|---|---|---|
| 2bxa | 2.35 | −9.03 | 0.63 | −10.61 | 0.18 | HSA | CMPF[c] | I | Carrier protein |
| 1HA2 | 2.50 | −6.67 | 0.40 | −7.31 | 1.12 | HSA | S-WRF[d] | I | Carrier protein |
| 2bxf | 2.95 | −8.50 | 0.20 | −9.05 | 0.20 | HSA | DZP[e] | II | Carrier protein |
| 2bxg | 2.70 | −7.68 | 0.79 | −7.75 | 0.24 | HSA | IBPF[f] | II | Carrier protein |
| 1EFH | 2.40 | −14.62 | 0.14 | −16.28 | 0.16 | Sult2A1 | ADP[g] | I | Metabolic enzyme |
| 1OV4 | 2.70 | −9.13 | 0.82 | −9.99 | 0.31 | Sult2A1 | AET-SO$_4$[h] | I | Metabolic enzyme |
| 2qp3 | 2.60 | −9.07 | 0.27 | −9.68 | 0.18 | Sult2A1 | AET[i] | I | Metabolic enzyme |
| 3ruk | 2.60 | −8.86 | 1.31 | −9.65 | 0.29 | CYP17A1 | ABT[j] | I | Target protein |
| 3swz | 2.40 | −10.22 | 0.17 | −10.02 | 0.17 | CYP17A1 | GLT[k] | I | Target protein |

[a]Cross-docking,
[b]Induced-Fit docking (native docking).

The resulting docking poses for hits with high docking scores were further docked using an Induced Fit docking workflow. In this docking protocol the conformational change of the enzyme and the ligand during binding are accounted for. Since CYP17A1 is a flexible enzyme it was important to yield conformers close to the real conformation in vivo. The hits that showed good docking scores were considered as potential CYP17A1 inhibitors.

After performing Induced Fit Docking, certain functional groups from the hit compound Z1567948782 (Compound 7) were altered to create derivatives thereof. The aim was to improve the inhibition potency of the hits. The derivatives of the hit for CYP17A1 binding Z1567948782 are as follows: Z2234084128 (Compound 9); Z2234175518 (Compound 10); Z2234175520 (Compound 11); Z2234185123 (Compound 12); and Z518027752, previously named 980171513 (Compound 13).

Computational docking calculations on further derivatives of Z2234185123 (Compound 12) revealed that they are also androgen receptor antagonists and inhibit various mutants of the androgen receptors.

The following hits, already available off the shelf in the database, but not previously tested for CYP17A1 and CYP19A1 inhibition, were also established: Z44426883 (Compound 1); Z92489215 (Compound 2); Z220306370 (Compound 3); and Z51102986 (Compound 6).

CYP17A1 hits Z220306370 (Compound 3) and Z51102986 (Compound 6) are typically found as racemic mixtures instead of single enantiomers.

Characteristics of Exemplary CYP17A1 Inhibition Hits

The hit Z2234175518 exhibits a similar binding mechanism as known CYP17A1 inhibitors Abiraterone and TOK-001 (Galeterone). However, our hit Z2234175518 shows a hydrogen bond between the N—H group of the 3-{[(3-oxo-3,4-dihydro-2H-1,4-benzoxazin-7-yl moiety and the carbonyl group of ASN202, with a bond radius of 2.06 Å. Furthermore, the carbonyl group of the 3-{[(3-oxo-3,4-dihydro-2H-1,4-benzoxazin-7-yl moiety shows a hydrogen bond with an OH group of TYR201, with a bond radius of 2.30 Å. The pyridine ring faces the Fe (+3) moiety of the active site and thus blocks access of the substrate to the Fe (+3) moiety for metabolism of steroids hormones. The hit is also accommodated by a few hydrophobic interactions with hydrophobic amino acids residues in the active site of CYP17A1 such as: ALA367, VAL482, ALA113, ALA105, ILE206, ILE205, LEU243, PHE300, TYR201, ILE198, ILE209, and ALA302.

The hit Z2234175520 shows a different binding mechanism different than that of Z2234175518 even though they share the same core structure and the only difference is that Z2234175520 does not have a pyridine ring. The hit Z2234175520 shows a strong hydrogen bond between the OH group of N-(2-hydroxyphenyl) as the hydrogen bond donor and the carbonyl group of VAL482 as the hydrogen bond acceptor, with a bond radius of 1.61 Å. A further strong hydrogen bond is shown between the oxygen atom of the 3-{[(3-oxo-3,4-dihydro-2H-1,4-benzoxazin-7-yl)amino] group as a hydrogen bond acceptor and the N—H group of ARG239 as a hydrogen bond donor, with a bond radius of 1.86 Å. The carbonyl group of 3-{[(3-oxo-3,4-dihydro-2H-1,4-benzoxazin-7-yl)amino] shows a hydrogen bond with the OH group of TYR201, with a bond radius of 2.15 Å. The N—H group of 3-{[(3-oxo-3,4-dihydro-2H-1,4-benzoxazin-7-yl)amino] group shows a hydrogen bond as a hydrogen bond donor with the carbonyl group of ASN202 as a hydrogen bond acceptor, with a bond radius of 2.33 Å. The hit is accommodated by hydrophobic interactions with the hydrophobic amino acid residues in the binding pocket of CYP17A1. The hydrophobic amino acids groups include the following: LEU209, ILE205, ILE206, TYR201, PHE300, ILE198, PHE114, ALA113, and ALA302.

The hit Z2234185123 shows a hydrogen bond between an N—H group of acetamide as a backbone hydrogen bond donor to the carbonyl group of LEU370 as a hydrogen bond acceptor, with a bond radius of 1.85 Å. The carbonyl group of the hit shows a side-chain hydrogen bond as a hydrogen bond acceptor with the N—H group of LEU214 as a hydrogen bond donor, with a bond radius of 1.97 Å. The carbonyl group of (3-oxo-3,4-dihydro-2H-1,4-benzoxazin-7-yl) as a hydrogen bond acceptor binds with the N—H group of ARG239 as a hydrogen bond donor, with a bond radius of 2.09 Å. The N—H group of N-{4-chloro-3-[(3- oxo-3,4-dihydro-2H-1,4-benzoxazin-7-yl)carbamoyl]phenyl} as a hydrogen bond donor shows a hydrogen bond with a carbonyl group of VAL482 as a hydrogen bond acceptor, with a bond radius of 2.42 Å. The binding mode for this ligand is quite different from the other derivatives of Z1567948782 in the sense that it has shown three backbone hydrogen bonds between the hit itself and the amino acid residues of the enzyme. The enzyme accommodates the hit molecules in its active site through hydrophobic interactions. The amino acid residues involved in hydrophobic interactions include the following: VAL215, MET369, LEU370, PRO368, PRO372, PHE114, TYR201, ILE206, VAL482, VAL366, ILE371, ALA367, and LEU214.

The hit Z518027752 (previously named 980171513) shows a strong hydrogen bond between the oxygen of the 3-{[(6-chloro-3-oxo-3,4-dihydro-2H-1,4-benzoxazin-7-yl) amino] group, as a hydrogen bond acceptor, with the N—H group of ARG239 as a hydrogen bond donor, with a bond radius of 1.80 Å. The aromatic ring of ARG239 also shows a π-π bond with an aromatic ring of 3-{[(6-chloro-3-oxo-3, 4-dihydro-2H-1,4-benzoxazin-7-yl)amino] group. The carbonyl group of 3-{[(6-chloro-3-oxo-3,4-dihydro-2H-1,4-benzoxazin-7-yl)amino] as a hydrogen bond acceptor shows a hydrogen bond with the OH group of TYR201 as a hydrogen bond donor, with a bond radius of 1.88 Å. The N—H group of 3-{[(6-chloro-3-oxo-3,4-dihydro-2H-1,4-benzoxazin-7-yl)amino] as a hydrogen bond donor shows a hydrogen bond with the carbonyl group ASN202 as a hydrogen bond acceptor, with a bond radius of 1.97 Å. The amino acid residues that are responsible for hydrophobic interactions include the following: TYR201, ILE198, ILE205, ILE206, LEU209, VAL482, VAL483, and VAL366.

The hit Z44426883 shows a strong hydrogen bond interaction between an OH group of 2-hydroxy-5-methoxybenzoyl as a hydrogen bond donor with the carbonyl group of ASP298 as a hydrogen bond acceptor, with a bond radius of 1.47 Å. The carbonyl group of 3-((4-ethylphenyl) carbamoyl) as a hydrogen bond acceptor shows a hydrogen bond with the N—H group of ARG239 as a hydrogen bond donor, with a bond radius of 1.96 Å. The NH2+ group of 2H-pyran-2-iminium group shows a salt-bridge interaction with the carboxylate group of GLU305. Amino acid side-chains such as PHE114, ALA105, LEU209, LEU102, LEU214, ALA367, VAL366, ILE371, LEU370, VAL482, and VAL483 are involved in hydrophobic interactions.

The hit Z220306370 is an R-enantiomer and shows a hydrogen bond network between the carbonyl group of acetamide and active site water, which also binds with the N—H group of ARG239. There is a π-π interaction between the phenyl group of the hit with the phenyl group of PHE114. The ferric-porphyrin moiety shows a π-π stacking interaction with the indole ring of the hit. Hydrophobic amino acid groups involved in hydrophobic interactions include the following: ALA113, PHE114, ALA302, LEU102, LEU209, ILE371, LEU214, TYR201, and VAL482. The binding mechanism shows similarities to the type of mechanism observed for TOK001 (Galeterone) and Abiraterone.

The hit Z51102986 shows a strong hydrogen bond between the N—H group of 4-butyramidophenyl as a hydrogen bond donor with the carbonyl group of ASN202 as a hydrogen bond acceptor, with a bond radius of 1.91 Å. The N—H group of the indazole moiety in the hit also shows a hydrogen bond with the carbonyl group of VAL482, with a bond radius of 2.17 Å. The hydrophobic groups involved in hydrophobic interactions in the binding pocket of the enzyme are as follows: VAL366, ALA367, VAL483, VAL482, ILE371, TYR201, ILE198, PHE300, LEU242, PHE114, LEU209, and ALA302.

The hit Z92489215 shows a hydrogen bond between the N—H group of the indole ring as a hydrogen bond acceptor with the OH group of THR306 as a hydrogen bond donor, with a bond radius of 1.75 Å. The indole ring of the hit exhibits a π-cation interaction with the Fe (+3) group of ferric-porphyrin. The carbonyl group of acetamide is involved in a hydrogen bond network with water and exhibits a bond radius of 1.96 Å. The hydrogen bond network between water and the acetamide group extends to the N—H group of ARG239 and the carbonyl group of GLY297. The hydrophobic groups of the hit are involved in hydrophobic interaction with the following amino acids: VAL366, ALA367, LEU370, VAL482, LEU102, PHE114, VAL483, ILE206, LEU209, and ILE205.

The hit Z1567948782 exhibits a strong hydrogen bond between the N—H group of the 6-chloro-3-oxo-3,4-dihydro-2H-benzo[b][1,4]oxazin-7-yl group as a hydrogen bond donor, which is directed at the carbonyl group of VAL482 as a hydrogen bond acceptor, with a bond radius of 1.79 Å. The N—H group of the phenyl methyl group as a hydrogen bond donor shows a hydrogen bond with the Fe (+3) in the porphyrin moiety, with a bond radius of 2.45 Å. There is also a hydrogen bond network in the active site between a water molecule and the carbonyl group of GLY297, with a bond radius of 1.83 Å, which does not involve the hit molecule.

The hit Z2234084128 shows a side-chain hydrogen bond between the OH group of N-(2-Hydroxyphenyl) and the carbonyl group ASN202 with a radius of 2.03 Å, and another side-chain hydrogen bond between the N—H group serving as hydrogen bond donor, and the carbonyl group of ASN202 serving as the hydrogen bond acceptor, with a bond radius of 2.29 Å. The carbonyl group of the carbamoylphenoxy group of Z2234084128 as a hydrogen bond acceptor shows a strong hydrogen bond with the N—H group of ARG239 as a hydrogen bond donor, with a bond radius of 1.98 Å. The phenyl group of N-(2-hydroxyphenyl) shows a π-π interaction with the phenyl group of PHE300.

As can be seen, many of the hits are accommodated by hydrophobic interactions with amino acid residues in the binding pockets of the active sites. The amino acids involved in such hydrophobic interactions include ALA105, ALA367, LEU370, VAL366, ALA302, LEU214, VAL482, VAL483, PHE114, ILE206, ILE205, LEU209, LEU242, PHE184, ILE246, PHE300, and ILE198.

Characteristics of Exemplary CYP19A1 Inhibition Hits

Docking of hits molecules to CYP19A1 enzyme was also carried out in order to establish whether dual inhibition of the CYP17A1 and CYP19A1 enzymes is possible.

The (R, R) enantiomer of the hit Z56773451 shows a backbone hydrogen bond between the oxygen of the OH group as a hydrogen bond acceptor and the N—H group of MET374 as a hydrogen bond donor, with a bond radius of 1.94 Å. The hydrogen of the OH group of the hit as a hydrogen bond donor shows a backbone hydrogen bond with the carbonyl group of LEU372, with a bond radius of 2.01 Å. The aromatic ring of the hit shows a π-π stacking with the phenyl group of ARG115. The bond between the hit and the active site amino acid residues is further strengthened by hydrophobic interactions with the following: ILE133, ILE305, ALA306, PHE221, TRP224, LEU477, VAL370, VAL372, VAL373, and MET374.

The (S, S) enantiomer of the hit Z56773451 shows a backbone hydrogen bond between the ortho OH group of the hit as a hydrogen bond donor with the carbonyl group of ASP309, with a bond radius of 1.86 Å. The ortho OH group of the aromatic ring of the hit as a hydrogen bond acceptor shows another side-chain hydrogen bond with the OH group of THR310, with a bond radius of 1.88 Å. The meta OH group of the aromatic ring of the hit shows a backbone hydrogen bond with the carbonyl group of ASP309, with a bond radius of 1.92 Å. The meta O⁻ group of the aromatic ring bonded to the cyclopentyl group in the hit shows a strong backbone hydrogen bond as a hydrogen bond acceptor with the N—H group of MET374, with a bond radius of 1.84 Å. The same O⁻ group of the aromatic ring of the hit shows another side-chain hydrogen bond with the N—H group of ARG115, with a bond radius of 2.06 Å. The para OH group of the aromatic ring of the hit shows a backbone hydrogen bond as a hydrogen bond donor with the carbonyl group of LEU372 as a hydrogen bond acceptor, with a bond radius of 2.07 Å. The same para OH group as a hydrogen bond acceptor shows a hydrogen bond with the N—H group of MET373, with a bond radius of 2.20 Å. The hydrophobic interactions between the hydrophobic groups of the hit and amino acid residues of the active site are as follows: VAL373, MET374, LEU372, LEU477, VAL370, VAL369, and LEU479.

The hit Z518027752 (previously named 980171513) shows a strong backbone hydrogen bond between the carbonyl group of the benzo oxazin ring as hydrogen bond acceptor and the N—H group of MET374 as hydrogen bond donor, with a bond radius of 1.96 Å. The N—H group of the ring as a hydrogen bond donor also shows a backbone hydrogen bond with the carbonyl group of LEU372 as a hydrogen bond acceptor, with a bond radius of 2.14 Å. The benzo oxazin ring shows a π-π bond with the $NH_2$ group of ARG115. There is also a hydrogen bond framework between active site water and the N—H group of VAL369 and 370, respectively. The hydrophobic interactions between the hydrophobic groups of the hit and amino acid residues of the active site are as follows: VAL373, MET374, LEU372, LEU477, TRP224, PHE221, ALA306, ILE132, and ILE305.

The hit Z2230799627 shows a strong backbone hydrogen bond between the carbonyl group of the benzoxazin ring as a hydrogen bond acceptor with the N—H group of MET374 as a hydrogen bond donor, with a bond radius of 1.80 Å. This binding mode is facilitated by hydrophobic interactions between the hit and amino acids of the active site which are as follows: MET374, VAL373, PHE134, LEU372, LEU477, PHE221, TYR220, TRP224, ILE305, MET127, ILE133, LEU152, PHE148, ILE132, & VAL370.

The hit Z2234175518 shows a strong hydrogen bond between the N—H group of amino methylene group of the hit as a hydrogen bond donor when it bonds with the oxygen of the OH group in SER478 as a hydrogen bond acceptor, with a bond radius of 1.87 Å. The carbonyl group of the benzoxazin ring as a hydrogen bond donor shows a hydrogen bond with the N—H group of MET374 as a hydrogen bond donor, with a bond radius of 1.98 Å. The N—H group of the benzoxazin ring as a hydrogen bond donor shows a hydrogen bond with the carbonyl group of LEU372, with a bond radius of 2.07 Å. The benzoxazin ring shows a π-π interaction with the $NH_2$ group of ARG115. There is a hydrogen bond framework between active site waters and the N—H groups of both VAL369 and VAL370, respectively. Hydrophobic interactions are facilitated by the following amino acid residues: MET374, VAL373, PHE134, TRP224, PHE221, ILE305, ALA306, VAL369, LEU477, VAL370, & LEU372.

The hit Z2234175520 shows a hydrogen bond between the carbonyl group of the benzoxazin ring as hydrogen bond acceptor and the OH group of THR310 as a hydrogen bond donor, with a bond radius of 1.84 Å. The N—H group of the benzoxazin ring as a hydrogen bond donor shows a hydrogen bond with the carbonyl group of VAL369, with a bond radius of 2.09 Å. The OH group of 2-hydroxyphenyl group as a hydrogen bond donor shows a hydrogen bond with oxygen of the OH group of THR310 as a hydrogen bond acceptor, with a bond radius of 2.40 Å. There is a hydrogen bond network between the carbonyl group of VAL370 and the active site waters as well as the N—H group with VAL369. There is a 7-cation interaction between the 2-hydroxy phenyl ring of the hit with the Fe (3+) group. The hydrophobic interactions are facilitated by the following amino acid residues in the active site of the enzyme: VAL373, ILE133, LEU477, MET374, LEU372, PHE134, TRP224, PHE221, VAL370, VAL369, & ALA306.

For the hit Z2234185123, the $NH_2$ group of carboxamide as a hydrogen bond donor shows a strong hydrogen bond with the carbonyl group of ASP309 as a hydrogen bond acceptor, with a bond radius of 1.94 Å. The carbonyl group of the benzoxazin ring as a hydrogen bond acceptor shows a hydrogen bond with the N—H group of MET374 as a hydrogen bond donor, with a bond radius of 2.03 Å. The nitrogen of pyrazole ring as a hydrogen bond acceptor shows a hydrogen bond with the OH group of SER478 as a hydrogen bond acceptor, with a bond radius of 2.38 Å. The pyrazole ring of HID480 shows a π-π interaction with the pyrazole ring of the hit. The pyrazole ring of the hit also shows another π-π interaction with the aromatic ring of PHE221. Hydrophobic interactions are facilitated by the following amino acid residues of the enzyme in its active site: ILE133, VAL373, MET374, LEU372, LEU477, PHE134, and VAL369.

The hit Z1567948782 shows a strong hydrogen bond between the carbonyl group of benzoxazin ring as a hydrogen bond acceptor and the N—H group of MET374 as a hydrogen bond acceptor, with a bond radius of 1.62 Å. The N—H group of the benzoxazin ring as a hydrogen bond donor is involved in a hydrogen bond with the carbonyl group of LEU372 as a hydrogen bond acceptor, with a bond radius of 2.08 Å. The benzamide ring of the hit shows three π-π interactions with the porphyrin ring. There is a hydrogen bond network exhibited by VAL369 as a hydrogen bond donor with its N—H group with active site waters as hydrogen bond acceptor, and VAL370 as the hydrogen bond donor with its carbonyl group and active site waters as the hydrogen bond donor. The hydrophobic amino acid residues of the enzyme involved in the hydrophobic interactions with the ligand are as follows: PHE221, TRP224, LEU477, PHE134, VAL373, MET374, LEU372, VAL370, ILE132, ILE133, LEU152, & ALA306.

The hit Z854502162 shows a hydrogen bond between the carbonyl group of carboxamide group as a hydrogen bond acceptor with the N—H group of MET374 as a hydrogen bond acceptor, with a bond radius of 2.00 Å. The $NH_2$ group of carboxamide as a hydrogen bond donor shows a hydrogen bond with the carbonyl group of LEU477 as a hydrogen bond acceptor, with a bond radius of 2.03 Å. The N—H group bonded to the phenyl group of the hit as a hydrogen bond donor shows a hydrogen bond with the carbonyl group of LEU477 as a hydrogen bond acceptor, with a bond radius of 2.16 Å. The phenyl group of the hit shows a π-π interaction with the benzyl group of PHE134. The hydrophobic amino acid residues of the enzyme involved in the hydrophobic interactions with the ligand are as follows: PHE134, MET374, VAL373, LEU372, LEU477, PHE221, VAL370, ILE305, ALA306, & ILE133.

Synthetic Protocols
General Procedure for Compounds Z225980484, Z51102986

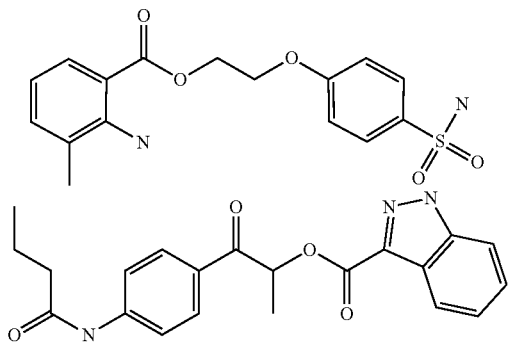

Instrumentation: The reaction was carried out in 8 ml glass vial.

Loading: The reactants were loaded in view that 1.0 equivalent is equal to 1.4 mmol of the compound.

Protocol: A vial was charged with acid (1.2 equiv.), DMF (2 ml), and DIPEA (1.2 equiv.). To the stirred mixture alkyl halide (1.0 equiv.) was added. The vial was capped and heated under the stirring for 1 h. After 30 min reaction mixture became clear and heating was continued for the next 6 h at 100° C. Then the vial was cooled, diluted with water, and extracted with chloroform. The combined organic layers were dried over sodium sulfate concentrated. The crude product was purified with CombiFlash chromatography on silica gel. The average yield was 50%.

General Procedure for Compounds Z220306370, Z92489215

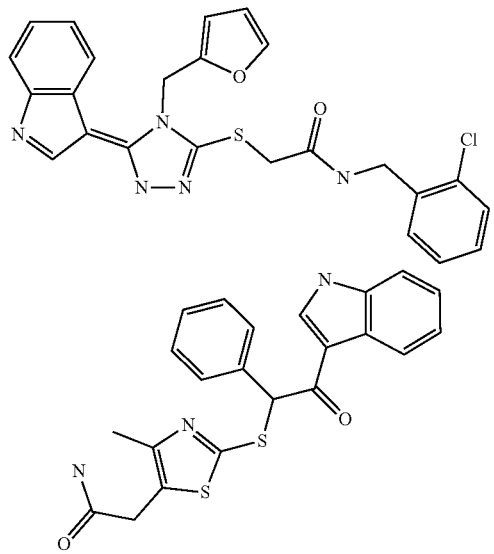

Instrumentation: The reaction was carried out in 8 ml glass vial.

Loading: The reactants were loaded in view that 1.0 equivalent is equal to 1.4 mmol of the compound.

A vial was charged with S-substituted reagent (1.0 equiv.), DMF (2 ml), DIPEA (1.2 equiv.). To the stirred mixture alkyl halide (1.0 equiv.) was added. The vial was capped and heated under the stirring for 1 h. After 30 min reaction mixture became clear and heating was continued for the next 3 h. Then the vial was cooled, diluted with water, and a formed precipitate was filtered off, washed with water and dried. The average yield was 20%.

Procedure for Compound Z854502162

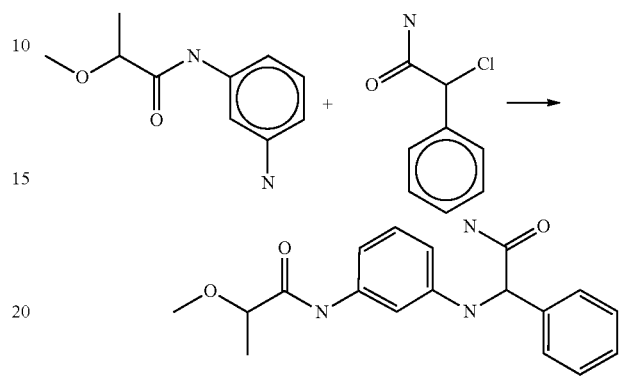

Instrumentation: The reaction was carried out in 8 ml glass vial.

Loading: The reactants were loaded in view that 1.0 equivalent is equal to 1.8 mmol of the compound.

To a stirred solution containing specified amounts of first reagent (1.0 equiv.), DIPEA (1.1 equiv.), and potassium iodide (catalytic) in 1 mL of DMF second reagent (1.0 equiv.) was added. The reaction mixture was allowed to stir on a boiling water bath for ca. 5 min. Upon a complete dissolution of the reagents the stirred reaction mixture was heated on the water bath for the 6 h.

The reaction mixture was triturated with an excess of deionized water and sonicated until a crystalline precipitate was formed. The precipitate was filtered, washed twice with methanol, and dried. The crude product was purified by chromatography (silica gel, $CHCl_3$:iPrOH=4:1). The yield was 30%.

Procedure for Compound Z44426883

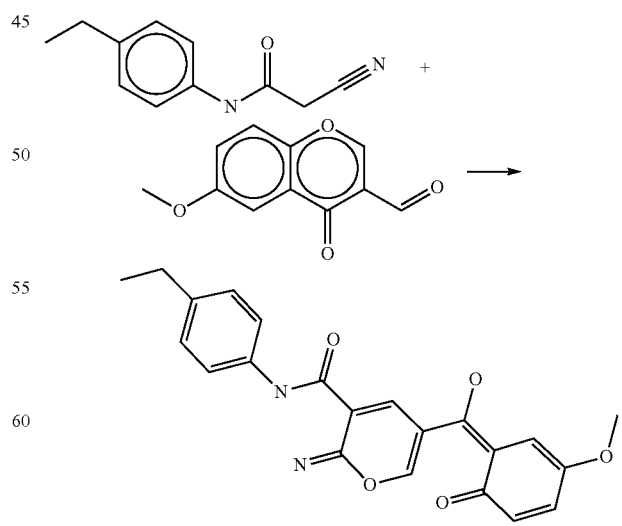

Instrumentation: The reaction was carried out in 8 ml glass vial.

Loading: The reactants were loaded in view that 1.0 equivalent is equal to 0.75 mmol of the compound.

A vial was charged with aldehyde (1.0 equiv.) and corresponding methylene active compound (1.0 equiv.), acetic acid (5 ml), and sodium acetate (1.1 equiv.). The vial was capped and heated at 100° C. for 8 h. Then it was cooled and diluted with water (5 ml). The formed precipitate was filtered, dried, and re-crystallized from acetonitrile. The yield was 48%.

Synthesis of Compounds 7 to 13 in Table 2:

Compound Z1567948782, which is Compound 7 in Table 2, is a parent compound of Compounds 8 to 13 in Table 2. The synthetic protocols for Compound 7 and its derivatives 8 to 13 are as follows:

Procedure for Compound Z1567948782 (Parent Compound 7)

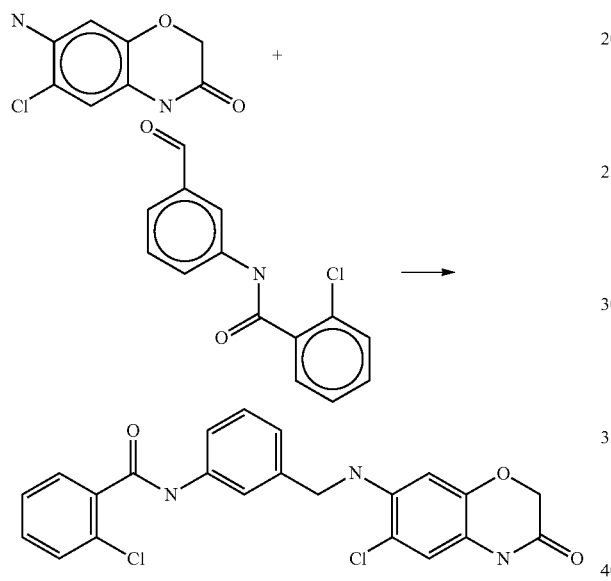

Instrumentation: The reaction was carried out in 8 ml glass vial.

Loading: The reactants were loaded in view that 1.0 equivalent is equal to 0.7 mmol of the compound.

The amine (1.0 equiv.) was dissolved in 3 mL of methanol and the reaction mixture was stirred in a vial at r. t. Then the aldehyde (1.0 equiv.) was added to the stirred solution. The vial with the reaction mixture was sonicated at 58-60° C. for 60-90 min until a complete dissolution of the reagents. Up to 5 mL of acetonitrile could be added to complete the dissolution of the reagents. The reaction vial was cooled to 0° C. and sodium borohydride (150 mg) was added to the reaction mixture in small portions. The reaction mixture was stirred in the open vial until sodium borohydride was dissolved. The reaction vial was sonicated for 2 hrs at r. t., closed, and allowed to stand overnight at r. t. Then the open reaction vial was sonicated at 50° C. until methanol was nearly completely evaporated. The reaction mixture was triturated with 5 mL of methanol and stirred until the large part of it was dissolved. The insoluble part largely consisted of inorganic salts. The product was purified by passing the methanolic suspension through ionic polymer scavengers. The product was eluted with methanol and the solvent removed under reduced pressure to yield the product. The crude product was purified by chromatography (silicagel, CHCl$_3$:iPrOH=4:1). The yield was 25%.

Synthesis of Derivatives of Z1567948782 (Parent Compound 7)

Synthesis was carried out following the schemes given below:

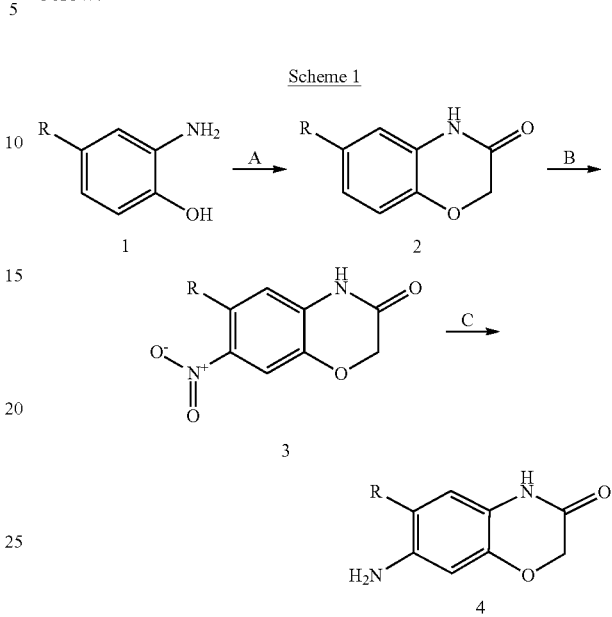

Scheme 3

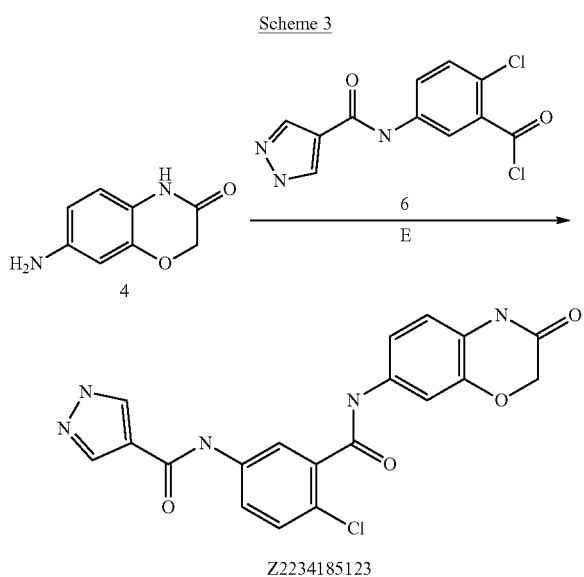

Z2234185123

Step A

To a solution of compound 1 (R=H; 3.0 g, 27.5 mmoles) in chloroform, TEBA (3.1 g, 13.7 mmol) and NaHCO$_3$ was added at 0° C. Then a solution of chloroacetyl chloride (4.6 g, 41.2 mmoles) in chloroform was added over 20 min. at the same temperature and the resulting mixture was allowed to stir at 60° C. for 16 hrs. After completion of the reaction, solvent was evaporated and washed with DCM and water. The organic layer was dried over Na$_2$SO$_4$ and concentrated under vacuum. The resulting solution was washed with pentane and ether as a co-solvent to get compound 2 (3.2 g, 78% yield) as solid which was pure enough to use directly for further reaction. Compounds with R=OH and Cl were obtained by the same procedure.

Step B

To an ice cooled solution of compound 2 (R=H; 0.60 g, 3.35 mmol) in AcOH (1.8 mL) was added drop wise 70% HNO3 (0.6 mL) and stirred at RT for 15 min. After completion of the reaction, the reaction mixture was poured into ice water (100 g), separated solids were filtered, washed with water, and dried under reduced pressure. The crude compound 3 was directly used for the next step without further purification (0.60 g, 80%). Compounds with R=OH and Cl were obtained by the same procedure.

Step C

A 1000 mL round-bottom flask was purged, flushed and maintained with a hydrogen atmosphere, then was added a solution of compound 3 (R=H; 16.5 g, 85.05 mmol, 1.00 equiv) in THF (500 mL). To the mixture was added Pd/C (10 percent, 4 g). The resulting solution was allowed to react, with stirring, overnight while the temperature was maintained at room temperature. The reaction progress was monitored by TLC (PE/EtOAc=1:1). A filtration was performed. The filtrate was concentrated by evaporation under vacuum using a rotary evaporator. This resulted in 13.5 g (97%) of compound 4 a red solid. Compounds with R=OH and Cl were obtained by the same procedure.

Step D

To a solution of 9.37 mmol of compound 4 in 15 ml of anhydrous ethanol 11.44 mmol of corresponding aldehyde 5 was added at room temperature with stirring. TLC was used to control the end point of the reaction. The reaction mixture was filtered. The resulting solid was washed with anhydrous ethanol to give 7.665 mmol of yellow solid product that was dissolved in 20 ml anhydrous ethanol. 0.445 g (11.5 mmol, 96%) sodium borohydride was added in portions and stirred for 30 minutes at room temperature. The reaction mixture was poured into ice water, filtered, dried to give products: compound 8 Z2230799627; compound 10 Z2234175518; compound 11 Z2234175520; & compound 13 Z518027752 (previously named 980171513). The yields were 74-92%.

Step E

To a solution of compound 4 (99 mg; 600 µmol) in anhydrous dichloromethane (2 ml) triethylamine (105 µl, 753 µmol), and acid chloride, 6 (170 mg, 600 µmol) in anhydrous dichloromethane (2 ml) were added and the mixture was agitated at room temperature for 14 hours. Water was added to the reaction solution and an organic phase was extracted with ethyl acetate. The organic phase was washed with water and saturated aqueous solutions of sodium bicarbonate and sodium chloride. The resulting mixture was dried over magnesium sulfate followed by concentration under a reduced pressure. A crude product was purified via silica gel column chromatography using hexane: ethyl acetate (1:1) as an eluting solvent yielding: compound 12 Z2234185123 (160 mg, 99%).

All molecules were synthesized as racemic mixtures instead of as separate enantiomers.

In Vitro Methodology:

1.1. CYP Inhibition Against Major 5 Human Liver CYPs in E. coli CYPEX Membranes 1.1.1. Compound Preparation Test compounds and control inhibitors were prepared as stocks in DMSO from the solid compound. The stocks were diluted in 0.1 M phosphate buffer (pH 7.4) at four times the final concentration prior to addition into the incubation tubes. The final DMSO concentration was 1%.

1.1.2. 5 CYP Incubations

Inhibition of 5 CYPs (CYP1A2, 2C9, 2C19, 2D6 and 3A4) was measured using a bactosome mix (5 CYPs heterologously expressed in E. coli and purchased as a custom made mix of all 5 isoforms from Cypex, Dundee; Catalogue number CYP/XG001, Batch XG001001).

TABLE 6

| CYP Bactosome mix from Cypex Ltd: | |
|---|---|
| Bactosomes | Batch number |
| CYP1A2LR | C1A2LR010 |
| CYP2C9R | C2C9R012 |
| CYP2C19R | C2C19R018 |
| CYP2D6LR | C2D6LR001-3 |
| CYP3A4LR | C3A4LR006 |

Selective and FDA accepted substrates for each isoform were used at a concentration around the $K_m$ for each substrate. Activity of each isoform was assessed by measuring the appearance of an isoform-specific metabolite. The CYP isoforms, substrates, incubation concentrations and measured metabolites are summarised in Table 7 below:

TABLE 7

CYP isoforms, substrates, incubation concentrations and measured metabolites:

| CYP isoform | Substrates | Metabolites |
|---|---|---|
| 1A2 | Tacrine (0.5 µM) (Sigma, Dorset) | 1-Hydroxytacrine |
| 2C9 | Diclofenac (2 µM) (Sigma) | 4'-Hydroxydiclofenac |

TABLE 7-continued

CYP isoforms, substrates, incubation concentrations and measured metabolites:

| CYP isoform | Substrates | Metabolites |
|---|---|---|
| 2C19 | (S)-Mephenytoin (40 µM) (Santa Cruz, Germany) | 4'-Hydroxymephenytoin |
| 2D6 | Bufuralol (10 µM) (Santa Cruz) | Hydroxybufuralol |
| 3A4 | Midazolam (2.5 µM) (Sigma) | 1'-Hydroxymidazolam |

Test compounds were tested at 6 concentrations (half-log dilutions) 50, 15.81, 5, 1.58, 0.5, 0.016 µM final concentration. A cocktail of 5 isoform-specific inhibitors was used as a positive control. The individual isoform-specific inhibitors, the concentration range used and the expected $IC_{50}$-values are summarized in Table 8 below:

TABLE 8

Positive control CYP inhibitors:

| CYP isoform | Control Inhibitors (cassetted) | Concentration range (µM) |
|---|---|---|
| 1A2 | α-Naphtoflavone (Sigma) | 1-0.0032 |
| 2C9 | Sulfaphenazole (Santa Cruz) | 10-0.032 |
| 2C19 | Tranylcypromine (Sigma) | 100-0.32 |
| 2D6 | Quinidine (Sigma) | 1-0.0032 |
| 3A4 | Ketoconazole (Sigma) | 0.3-0.00095 |

Incubation reactions were set up as shown in Table 9 below:

TABLE 9

Incubation mix:

| | Volume | [Final] |
|---|---|---|
| 2x Substrate and CYP mix | 50 µl | CYP concentration 32.5 pmol/ml (protein 0.1 mg/ml) |
| 4x inhibitor(s) (100x DMSO stock diluted 1/25 in buffer) | 25 µl | |
| 4 mM NADPH (Fisher) | 25 µl | 1 mM |

Incubations were performed with shaking at 1500 rpm, for exactly 10 minutes at 37° C. Reactions were stopped by addition of 100 µl MeOH/1 µM Tolbutamide (internal standard). The quenched samples were mixed thoroughly and protein precipitated at −20° C. overnight. Samples were centrifuged at 2,500×g (3,400 rpm) for 20 minutes, 4° C. The supernatants were transferred to a 96 well-plate and analysed by LC-MS/MS.

1.1.3. LC-MS/MS Analysis

The following LC-MS/MS conditions were used to analyse the 5CYP inhibition samples:
Column: Waters ACE Excel C18-AR, 50×2.1 mm, 2 µm
Mobile phase A: MilliQ water+0.1% formic acid
Mobile phase B: Methanol+0.1% formic acid
Flow rate: 0.8 ml/min

TABLE 10

LC gradient:

| Time | % A |
|---|---|
| 0.00 | 5 |
| 0.20 | 5 |
| 1.50 | 85 |
| 1.55 | 99 |
| 2.00 | 99 |
| 2.05 | 5 |
| 2.10 | 5 |

TABLE 11

MRM methods:

| Compound | Parent (m/z) | Daughter (m/z) |
|---|---|---|
| 1'-Hydroxytacrine | 215.03 | 197.00 |
| 4'-Hydroxy S-mephenytoin | 235.10 | 150.00 |
| Hydroxybufuralol | 278.14 | 186.00 |
| 4'-Hydroxydiclofenac | 312.10 | 229.80 |
| 1'-hydroxymidazolam | 341.92 | 202.80 |
| Tolbutamide | 271.03 | 90.89 |

1.2. CYP17A1 Inhibition 1.2.1. Compound Preparation

Test compounds and control inhibitors were prepared as stocks in DMSO from the solid compound. Ammonium acetate, tolbutamide, 17α-Hydroxyprogesterone, and progesterone were purchased from Sigma-Aldrich (Gillingham, UK), and Ketoconazole was purchased from Sequoia Research Products Ltd. (Pangbourne, UK). HPLC-grade methanol and formic acid were from Fisher Scientific (Loughborough, UK). Water for HPLC was purified on a Milli Q system (Millipore, Watford, UK).

1.2.2. CYP17A1 Incubations

CYP17A1 inhibition was measured using 20 pmol/ml CYP17A1 bactosomes (Cypex, Dundee, UK) and 0.1 µM progesterone as a substrate and 1 mM NADPH in 50 mM potassium phosphate buffer pH 7.4 containing 5 mM magnesium chloride. Inhibitors were dissolved in DMSO and serially diluted in seven ½ log steps, final concentrations ranging from 50 µA to 50 nM. Reaction volume was 100 µl and final DMSO concentration was 1% (v/v). Reactions were started by the addition of NADPH and incubated at 37° C. for 20 minutes with shaking at 1800 rpm on a Bioshake IQ (Q-Instruments, Jena, Germany). Reactions were terminated by the addition of 200 µl methanol containing 1 µM tolbutamide as an internal standard.

1.2.3. LC-MS/MS Analysis

The following LC-MS/MS conditions were used to analyse 17α-Progesterone in the CYP17A1 inhibition samples: 17α-Progesterone production was assessed semi-quantitatively by liquid chromatography/tandem mass spectrometry (LC-MS/MS) using electrospray ionisation (ESI) in positive mode. 8 µl of each sample were analysed in MRM mode on a Waters Quattro Ultima Platinum triple-quadrupole mass spectrometer combined with a Waters Acquity UPLC system (Waters Corp., Milford, Mass., USA).
Column: ACE Excel C18-AR, 50×2.1 mm, 2 µm
Mobile phase A: MilliQ water+0.1% formic acid+0.025% (w/v) ammonium acetate
Mobile phase B: Methanol+0.1% formic acid+0.025% (w/v) ammonium acetate
Flow rate: 0.8 ml/min
Column temperature: 65° C.

TABLE 12

LC gradient:

| Time | % A |
|---|---|
| 0.00 | 95 |
| 1.00 | 1 |
| 1.30 | 1 |
| 1.31 | 95 |
| 1.50 | 95 |

TABLE 13

MRM methods:

| Compound | Parent (m/z) | Daughter (m/z) |
|---|---|---|
| 17α-Hydroxyprogesterone* | 331.1 | 96.84 |
| 17α-Hydroxyprogesterone* | 331.1 | 108.86 |
| Tolbutamide | 271.13 | 74.29 |

1.3. CYP19A1 Inhibition.

1.3.1. Compound Preparation

Test compounds and control inhibitors were prepared as stocks in either Acetonitrile or DMSO from the solid compound. Compounds were serially diluted in ½ log steps in the same solvent.

1.3.2. CYP19A1 Incubations

CYP19A1 inhibition experiments were performed using the CYP19/MFC High Throughput Inhibitor Screen Kit (Corning). Test compounds were tested in seven concentrations: Compounds that were soluble in acetonitrile were tested at 50.0, 15.8, 5.0, 1.58, 0.5, 0.158 and 0.05 µM, whilst compounds that had to be dissolved in DMSO, because they were found to be insoluble in acetonitrile, were tested at 25, 7.9, 2.5, 0.79, 0.25, 0.079, and 0.025 µM.

CYP19A1 reactions were performed in black 96 well-plates (Greiner) according to the manufacturer's instructions. Each 200 µl reaction consisted of 7.5 pmol/ml CYP19A1, 25 µM 7-Methoxy-4-trifluoromethylcoumarin (MFC) and a NADPH-regenerating system consisting of 8.2 µM NADP+, 0.42 mM $MgCl_2$, 0.42 mM Glucose-6-phosphate, 0.337 units Glucose-6-phosphate dehydrogenase in 50 mM potassium phosphate buffer pH 7.4. Final organic solvent concentrations were either 4% (v/v) acetonitrile or 0.5% (v/v) Dimethyl sulfoxide. The plates were covered with self-adhesive film lids and incubated for 10 minutes at 37° C. Reactions were terminated by the addition of 75 µl Stop Solution (100 mM Tris base in acetonitrile: MilliQ water (80:20).

1.3.3. Fluorescence Quantification

Fluorescence of 7-Hydroxy-4-trifluoromethylcoumarin (HFC) was measured on a SpectraMax® i3x (Molecular Devices) using 409 nm and 530 nm as excitation and emission wavelengths, respectively.

1.3.4. Data Analysis

The CYP activities for each test compound/positive control inhibitor at each concentration were converted to % of control activity (CA). The LC-MS/MS peak responses (CYP metabolite peak area/internal standard peak area) for each test compound or positive control inhibitor were used and the response for each sample was expressed as a percentage of an uninhibited control (DMSO incubation). The data were then expressed as (log(CA/100-CA) and used to generate a pseudo-Hill plot, the slope and y axis intercept are used to calculate the $IC_{50}$-value according to the following equation.

$$IC_{50} = 10^{\frac{intercept}{slope}}$$

Liquid Chromatography/Mass Spectrometry (LCMS) Results for the various compounds synthesized are shown in FIG. 9.

The specific embodiments, methods and procedures of the invention that are disclosed herein are given for illustrative purposes. Those skilled in the art will appreciate that variations of the invention are possible without departing from the scope thereof.

INDUSTRIAL APPLICABILITY

The invention has industrial applicability in the field of pharmacology, drug design and the treatment of cancer.

The compounds have pharmaceutical and therapeutical application. They selectively occupy specific receptors and find application in the treatment of pathological conditions in the form of prostate and breast cancers.

Advantageous Effects of Invention

The invention may provide advantages over previously known therapeutic strategies and compounds for CYP17A1 and CYP19A1 inhibition.

For example, selected compounds identified in this invention exhibit dual inhibition activity (inhibition of both CYP17A1 and CYP19A1).

In terms of docking results, the heterocyclic hits evidence a fit in the active site of the CYP17A1 enzyme and block access to ferric (+3) which is penta-coordinated to porphyrin and cysteine amino acid.

The results of the in vitro testing indicate that compounds disclosed herein provide an additional arsenal in the fight against cancer.

CITATION LIST

Citation list follows:

Patent Literature

PTL1: U.S. Pat. No. 7,498,331
PTL2: U.S. Pat. No. 7,574,340
PTL3: U.S. Pat. No. 7,960,435
PTL4: U.S. Pat. No. 8,445,677
PTL5: US20110118219A1

Non Patent Literature

NPL1: Highly-selective 4-(1,2,3-triazole)-based P450c17a 17,20-lyase inhibitors; Rafferty, S. W., Eisner, J. R., Moore, W. R., Schotzinger, R. J., Hoekstra, W. J.; 2014; Bioorganic and Medicinal Chemistry Letters.

NPL2: CYP17A1 inhibitors—Abiraterone, C17, 20-lyase inhibitors and multi-targeting agents; Yin, L., Hu, Q.; 2014; Nature Reviews Urology.

NPL3: Highly potent and selective nonsteroidal dual inhibitors of CYP17/CYP11B2 for the treatment of prostate cancer to reduce risks of cardiovascular diseases; Pinto- Bazurco Mendieta, M. A. E., Hu, Q., Engel, M., Hartmann, R. W.; 2013; Journal of Medicinal Chemistry.

NPL4: Recent progress in pharmaceutical therapies for castration-resistant prostate cancer; Yin, L., Hu, Q., Hartmann, R. W.; 2013; International Journal of Molecular Sciences.

NPL5: Steroidal 5α-reductase and 17α-hydroxylase/17,20-lyase (CYP17) inhibitors useful in the treatment of prostatic diseases; Salvador, J. A. R., Pinto, R. M. A., Silvestre, S. M.; 2013; Journal of Steroid Biochemistry and Molecular Biology.

NPL6: Targeting the adrenal gland in castration-resistant prostate cancer: A case for orteronel, a selective CYP-17 17,20-lyase inhibitor; Zhu, H., Garcia, J. A.; 2013; Current Oncology Reports.

NPL7: Agents that target androgen synthesis in castration-resistant prostate cancer; Ferraldeschi, R., De Bono, J.; 2013; Cancer Journal (United States) 19 (1), pp 34-42.

NPL8: Maestro, version 10.2, Schrödinger, LLC, New York, N.Y., 2015.

NPL9: MacroModel, version 10.8, Schrödinger, LLC, New York, N.Y., 2015.

NPL10: Phase, version 4.3, Schrödinger, LLC, New York, N.Y., 2015.

NPL11: Dixon, S. L.; Smondyrev, A. M.; Knoll, E. H.; Rao, S. N.; Shaw, D. E.; Friesner, R. A., "PHASE: A New Engine for Pharmacophore Perception, 3D-QSAR Model Development, and 3D Database Screening. 1. Methodology and Preliminary Results," J. Comput. Aided Mol. Des., 2006, 20, 647-671.

NPL12: Jaguar, version 8.8, Schrödinger, LLC, New York, N.Y., 2015.

NPL13: Induced Fit Docking protocol 2015-2, Glide version 6.4, Prime version 3.7, Schrödinger, LLC, New York, N.Y., 2015.

NPL14: Sherman, W.; Day, T.; Jacobson, M. P.; Friesner, R. A.; Farid, R., "Novel Procedure for Modeling Ligand/Receptor Induced Fit Effects," J. Med. Chem., 2006, 49, 534.

NPL15: Sherman, W.; Beard, H. S.; Farid, R., "Use of an Induced Fit Receptor Structure in Virtual Screening," Chem. Biol. Drug Des., 2006, 67, 83.

NPL16: Training and Test Set Compounds (see Tables 4 & 4A above): References for Table 4:

Kaku, T.; Hitaka, T.; Ojida, A.; Matsunaga, N.; Adachi, M.; Tanaka, T.; Hara, T.; Yamaoka, M.; Kusaka, M.; Okuda, T.; Asahi, S.; Furuya, S.; Tasaka, A., Discovery of orteronel (TAK700), a naphtylmethylimidazole derivative, as a highly selective 17,20-lyase inhibitor with potential utility in the treatment of prostate cancer; Bioorgan. Med. Chem., (2011a), 19: 6383-6399.

Handratta, V. D; Vasaitis, T. S; Njar, V. C; Gediya, L. K; Kataria, R; Chopra, P; Newman, D jr; Farquhar, R; Guo, Z; Qui, Y; Brodie, A. M; Novel C-17-heteroaryl steroidal CYP17 inhibitors/antiandrogens: synthesis, in vitro biological activity, pharmacokinetics, and antitumor activity in the LAPC4 human prostate cancer xenograft model; J. Med. Chem., (2005), 48: 2972-2984.

Budha, N. R.; Mehrotra, N.; Tangallapally, R.; Qi, R. J.; Daniels, A. J.; Lee, R. E.; Meibohm, B.; Pharmacokinetically-guided lead optimization of nitrofuranylamide anti-tuberculosis agents, APPS. J., (2008), 10: 157-165.

18. Nnane, I. P.; Kato, K.; Liu, Y.; Long, B. J.; Lu, Q.; Wang, X.; Ling, Y. Z.; Brodie, A., Inhibition of Androgen Synthesis in Human Testicular and Prostatic Microsomes and in Male Rats by Novel Steroidal Compounds; Endocrinology., (1999), 140: 2891-2897.

Hu, Q.; Jagusch, C.; Hille, U. E.; Haupenthal, J.; Hartmann, R. W., Replacement of imidazolyl by pyridyl in biphenylmethylenes results in selective CYP17 and dual CYP17/CYP11B1 inhibitors for the treatment of prostate cancer; J. Med. Chem., (2010a), 53: 5749-5758.

Kaku, T.; Tsujimoto, S.; Matsunaga, N.; Tanaka, T.; Hara, T.; Yamaoka, M.; Kusaka, M.; Tasaka, A., 17,20-Lyase inhibitors. Part 3: Design, synthesis, and structure-activity relationships of biphenylylmethylimidazole derivatives as novel 17, 20-lyse inhibitors; Bioorgan. Med. Chem., (2011b), 19: 2428-2442.

References for Table 4A

1. Jagusch, C; Negri, M; Hille, U. E; Hu, Q; Bartels, M; Jahn-Hoffmann, K; Pinto-Bazurco Mendieta, M. A. E; Rodenwaldt, B; Müller-Vieira, U; Schmidt, D; Lauterbach, T; Recanatini, M; Cavalli, A; Hartmann, R. W; Synthesis, biological evaluation and molecular modelling studies of methylene imidazole substituted biaryls as inhibitors of human 17α-hydroxylase-17,20-lyase (CYP17). Part I: Heterocyclic modifications of the core structure; Bioorganic and Medicinal Chemistry Journal., 2008, 16: 1992-2010.

2. Haider, S. M; Patel, J. S; Poojari, C. S; Neidle, S; Molecular Modeling on inhibitor complexes and active-site Dynamics of Cytochrome P450 C17, a target for prostate cancer therapy; J. Mol. Biol., 2010, 400: 1078-1098.

3. Yap, T. A; Carden, C. P; Attard, G; de Bono, J. S; Targeting CYP17: established and novel approaches in prostate cancer; Curr. Opinion in Pharmacol., 2008, 8: 449-457.

4. Gianti, E; Zauhar, R. J; Modeling androgen receptor flexibility: A binding mode hypothesis of CYP17 inhibitors/antiandrogens for prostate cancer therapy; J. Chem. Inf. Model. 2012, 52: 2670-2683.

5. Schaefer, G; Mosquera, J. M; Ramoner, R; Park, K; Romanel, A; Steiner, E; Horninger, W; Bektic, J; Ladurner-Rennau, M; Rubin, M. A; Demichelis, F; Klocker, H; Distinct ERG rearrangement prevalence in prostate cancer: higher frequency in young age and in low PSA prostate cancer; Prostate Cancer and Prostatic Disease., 2013, 16: 132-138.

6. Lippolis, G; Edsjö, A; Stenman, U. H; Bjartell, A; A high density tissue micro-array from patients with clinically localized prostate cancer reveals ERG and TATI exclusivity in tumor cells; Cancer and Prostatic Disease, 2013, 16: 145-150.

7. Vasaitis, T. S; Bruno, R. D; Njar, V. C. O; CYP17 inhibitors for prostate cancer therapy; Journal of Steroid Biochemistry and Molecular Biology., 2011, 125: 23-31.

8. Bruno, R. D; Vasaitis, T. S; Gediya, L. K; Purushottamachar, P; Godbole, A. M; Ates-Alagoz, Z; Brodie, A. M. H; Njar, V. C. O; Synthesis and biological evaluations of putative metabolically stable analogs of VN/124-1 (TOK-001): Head to head anti-tumor efficacy evaluation of VN/124-1 (TOK-001) and abiraterone in LAPC-4 human prostate cancer xenograft model; Steroids., 2011, 76: 1268-1279.

9. McConnel, J. D; Carter, H. B; Physiologic basis of endocrine therapy for prostatic cancer; Urol. Clin. North. Am., 1991, 18:1-13.

10. Miller, W. L; Molecular Biology of steroid hormone synthesis; Endocr. Rev, 1990, 9: 295-318.

11. Easton, D. F; Schaid, D. J; Whitemore, A. S; Isaacs, W. J; Where are the prostate cancer genes? A summary of eight genome wide searches; Prostate, 2003, 57: 261-269.
12. Akhtar, M. K; Kelly, S. L; Kaderbhai, M. A; Cytochrome b5 modulation of 17α hydroxylase and 17-20 lyase (CYP17) activities in stereogenesis; Journal of Endocrinology, 2005, 187: 267-274.
13. Haider, S; Ehmer, P. B; Barassin, S; Batzl-Hartmann, C; Hartmann, R. W; Effects of novel 17α-hydroxylase/C17, 20-lyse (P450 17, CYP17) inhibitors on androgen biosynthesis in vitro and in vivo; Journal of Steroid Biochemistry and Molecular Biology., 2003, 85: 555-562.
20. DeVore, N. M; Scott, E. E; Structures of cytochrome P450 17A1 with prostate cancer drugs abiraterone and TOK001; Nature, 2012, 482: 116-120.

What is claimed is:

1. A compound for use as a medicament, said compound having the formula:

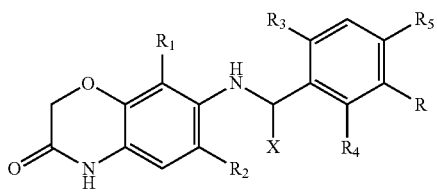

[Chem. 1]

wherein:
Each R1, R2, R3, R4, R5 is independently selected from the group consisting of H; OH; a halogen atom; OCH$_3$; and NH$_2$; and
X is independently selected from the group consisting of H; OH and =O;
and pharmaceutically acceptable enantiomers, diastereomers, tautomers, salts, solvates, and hydrates and where R is selected from the group consisting of

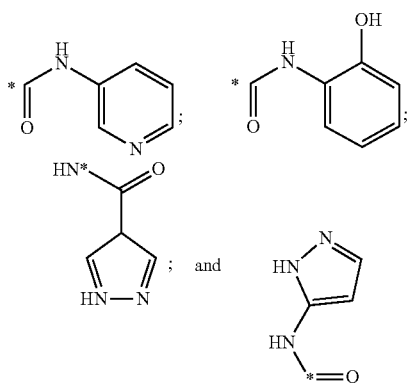

where the point of attachment to Chem. 1 is indicated by an asterisk (*) in each case.

2. The compound for use as a medicament, as claimed in claim 1, said compound being selected from the group consisting of:

N-{4-chloro-3-[(3-oxo-3,4-dihydro-2H-1,4-benzoxazin-7-yl) carbamoyl]phenyl}-1H-pyrazole-4-carboxamide; and pharmaceutically acceptable enantiomers, diastereomers, tautomers, salts, solvates and hydrates thereof.

3. A compound, enantiomer, diastereomer, tautomer, salt, solvate, or hydrate as claimed in claim 1, for use in the treatment of cancer mediated by CYP17A1 enzyme and/or CYP19A1 enzyme.

4. The compound, enantiomer, diastereomer, tautomer, salt, solvate, or hydrate, as claimed in claim 1, for use in the treatment of prostate cancer mediated by CYP17A1 enzyme and/or CYP19A1 enzyme.

5. The compound, enantiomer, diastereomer, tautomer, salt, solvate, or hydrates claimed in claim 1, for use in the treatment of breast cancer mediated by CYP17A1 enzyme and/or CYP19A1 enzyme.

6. A compound for direct inhibition of both the CYP17A1 enzyme and the CYP19A1 enzyme, said compound being selected from the group consisting of:

N-{4-chloro-3-[(3-oxo-3,4-dihydro-2H-1,4-benzoxazin-7-yl) carbamoyl]phenyl}-1H-pyrazole-4-carboxamide (Molecular Formula: C$_{19}$H$_{14}$ClN$_5$O$_4$); and pharmaceutically acceptable enantiomers, diastereomers, tautomers, salts, solvates, or hydrates thereof.

7. A compound for direct inhibition of CYP19A1 enzyme, said compound being selected from the group consisting of:

N-{4-chloro-3-[(3-oxo-3,4-dihydro-2H-1,4-benzoxazin-7-yl) carbamoyl]phenyl}-1H-pyrazole-4-carboxamide; and pharmaceutically acceptable enantiomers, diastereomers, tautomers, salts, solvates, or hydrates thereof.

8. The compound, enantiomer, diastereomer, tautomer, salt, solvate, or hydrate for use as a medicament, as claimed in claim 1, whenever formulated for administration to a patient in a mode selected from the group consisting of: solid form, powder, tablet, capsule, suspension, emulsion, sterile solution, injection, suppository, topical composition, and inhalable composition.

* * * * *